(12) United States Patent
White et al.

(10) Patent No.: US 8,772,330 B2
(45) Date of Patent: Jul. 8, 2014

(54) INHIBITOR(S) OF TRANSPORTERS OR UPTAKE OF MONOAMINERGIC NEUROTRANSMITTERS

(75) Inventors: James David White, Philomath, OR (US); David T. Wong, Indianapolis, IN (US); David B. Chan, Nashua, NH (US); Jongtae Yang, Corvallis, OR (US); Rajan Juniku, Corvallis, OR (US)

(73) Assignee: State of Oregon acting by and through the State Board of Higher Education on behalf of Oregon State University, Corvallis, OR (US)

(*) Notice: Subject to any disclaimer, the term of this patent is extended or adjusted under 35 U.S.C. 154(b) by 190 days.

(21) Appl. No.: 13/355,371

(22) Filed: Jan. 20, 2012

(65) Prior Publication Data

US 2012/0190725 A1 Jul. 26, 2012

Related U.S. Application Data

(63) Continuation-in-part of application No. PCT/US2010/042259, filed on Jul. 16, 2010.

(60) Provisional application No. 61/227,918, filed on Jul. 23, 2009, provisional application No. 61/255,044, filed on Oct. 26, 2009.

(51) Int. Cl.
  *A61K 31/381* (2006.01)
  *C07D 333/16* (2006.01)
(52) U.S. Cl.
  CPC ............ *A61K 31/381* (2013.01); *C07D 333/16* (2013.01)
  USPC ........................................... 514/438; 549/75
(58) Field of Classification Search
  CPC ............................ C07D 333/16; A61K 31/381
  USPC ....................................... 514/438; 549/68, 75
  See application file for complete search history.

(56) References Cited

U.S. PATENT DOCUMENTS

| | | | |
|---|---|---|---|
| 5,023,269 A | 6/1991 | Robertson et al. | |
| 5,120,752 A | 6/1992 | Brooks et al. | |
| 2006/0111353 A1 | 5/2006 | Welchert et al. | |
| 2008/0242653 A1 | 10/2008 | Liu et al. | |

OTHER PUBLICATIONS

International Search Report dated Aug. 30, 2010, from International Application No. PCT/US2010/042259.

*Primary Examiner* — Taofiq A Solola
(74) *Attorney, Agent, or Firm* — Klarquist Sparkman, LLP

(57) ABSTRACT

The present disclosure concerns a compound, or a pharmaceutically acceptable salt thereof, having a formula:

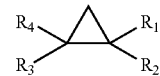

where at least one of $R_1$-$R_4$ is a heterocycle, at least one of $R_1$-$R_4$ is an aryl group coupled to the ring by a linker atom, functional group, or other moiety, or where none of $R_1$-$R_4$ is an amide, and any and all combinations thereof. Remaining $R_1$-$R_4$ substituents independently are aliphatic, substituted aliphatic, amine, substituted amine, aryl, substituted aryl, cyclic, substituted cyclic, halide, heteroaryl, substituted heteroaryl, heterocyclic, substituted heterocyclic, hydrogen or hydroxyl. A method for treating a subject also is provided comprising administering a disclosed compound or compounds, or a prodrug that is converted into the disclosed compound or compounds, or a composition comprising the compound, compounds, or prodrugs thereof, to a subject. A method for making disclosed compounds also is provided.

12 Claims, 5 Drawing Sheets

INHIBITOR(S) OF TRANSPORTERS OR UPTAKE OF MONOAMINERGIC NEUROTRANSMITTERS

CROSS REFERENCE TO RELATED APPLICATION

This is a continuation-in-part under 35 U.S.C. §120 of PCT/US2010/042259, which claims the benefit of the earlier filing dates of U.S. Provisional Application Nos. 61/227,918, filed on Jul. 23, 2009, and 61/255,044, filed on Oct. 26, 2006. Each of these prior applications is incorporated herein by reference.

STATEMENT OF GOVERNMENT SUPPORT

This invention was made with United States government support under Contract No. N02-DK-6-2911 awarded by the National Institute of Diabetes and Digestive and Kidney Disease, the National Institutes of Health. The United States government has certain rights in the invention.

FIELD

The present disclosure concerns inhibitors of transporters or uptake of monoaminergic neurotransmitters, compositions comprising such compounds, and embodiments of a method for making and for administering such compounds or compositions to a subject.

BACKGROUND

Neurotransmitters relay, amplify and/or modulate electrical signals between a neuron and adjacent neurons. Monoamine neurotransmitters include the catecholamines, such as norepinephrine [4-(2-amino-1-hydroxyethyl)benzene-1,2-diol] and dopamine [4-(2-aminoethyl)benzene-1,2-diol]; serotonin (5-hydroxytryptaminne, 5-HT); and histamine [2-(3H-imidazol-4-yl)ethanamine].

It is believed that many clinical conditions arise, at least in part, from a neurotransmitter imbalance. Serotonin regulates many physiological processes via activation of at least one of its 14 distinct receptors that are organized into 7 subfamilies. An imbalance in serotonergic neurotransmission in the central nervous system (CNS) is likely associated with mental illnesses, including depression, anxiety, schizophrenia, eating disorders, obsessive compulsive disorder (OCD) and migraines.

Selective serotonin reuptake inhibitors (SSRIs) increase the synaptic level of serotonin by inhibiting the serotonin-specific transporters to prevent re-entry of serotonin into its nerve terminals or neurons, thus increasing the serotonin available to bind to the postsynaptic receptors. SSRIs show less affinity for other monoamine transporters. SSRIs are first choice therapeutics for treating depression, certain forms of anxiety and social phobias and typically are tolerated better by subjects compared to classic tricyclic antidepressants.

While the serotonergic system modulates mood, the norepinephrinergic system modulates drive and energy. Drugs, including the secondary-amine-containing tricyclic antidepressants, desipramine and nortryptyline that affect mainly the norepinephrinergic system, have been available for some time.

Norepinephrine and serotonin receptors are known to interact anatomically and pharmacologically. Compounds that affect only serotonin exhibit modulatory effects on norepinephrine, pointing toward an important relationship between the two neurotransmitter systems. Duloxetine [(+)-N-methyl-3-(1-naphthalenyloxy)-2-thiophenepropanamine hydrochloride] inhibits both norepinephrine and serotonin reuptake. U.S. Pat. Nos. 4,956,388 and 5,023,269. Duloxetine (Cymbalta®) currently is being approved for the treatment of depression, diabetes peripheral neuropathic pain, general anxiety disorder, and urinary incontinence.

Efficacy and tolerability are important factors that determine the choice of a therapeutic. Older tricyclic antidepressants (TCAs) are associated with significant cognitive impairment and sedation. SSRIs are largely devoid of these effects, but gastrointestinal disturbances such as nausea and dyspepsia are common (Hindmarch I., 1997, Human Psychopharmacology, 12:115 119). For example, for the widely prescribed SSRI sertraline [(1S)-cis-(3,4-dichlorophenyl)-1,2,3,4-tetrahydro-N-methyl-1-napthalenamine] (Zoloft®, Pfizer, Inc.) the top three adverse events associated with discontinuation of treatment were nausea, insomnia and diarrhea (Physician's Desk Reference, 57th Edition, 2003, Thomson Medical).

It is difficult to predict chemical structure that will provide both a desired therapeutic activity and subject tolerance. Therefore a variety of therapeutics is needed to treat the full range of maladies associated with neurotransmitter modulation and/or imbalance. The present disclosure concerns new compounds, primarily embodiments having a cyclopropane ring, that are effective therapeutics. Applicants are aware of only one known dual serotonin and noradrenaline uptake inhibitor having a cyclopropane ring, namely milnacipran, which is shown below.

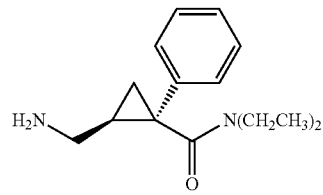

See, Wong et al., "Dual Serotonin and Noradrenaline Uptake Inhibitor Class of Anti-depressants—Potential for Greater Efficacy or Just Hype," *Progress in Drug Research*, 58, 169-222 (2002). Thus, despite these known compounds, there still is a need to develop additional compounds that ameliorate or eliminate the disadvantages of known neurotransmitter therapeutics.

SUMMARY

Certain disclosed embodiments of the present disclosure concern a compound, or a pharmaceutically acceptable salt thereof, other than milnacipran, having a formula:

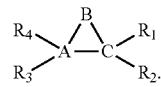

With reference to this general formula, A-C independently are carbon, nitrogen, oxygen or sulfur. $R_1$-$R_4$ substituents independently are aliphatic, substituted aliphatic, amine, substituted amine, aryl, substituted aryl, cyclic, substituted cyclic, halide, heteroaryl, substituted heteroaryl, heterocyclic, substituted heterocyclic, hydrogen or hydroxyl. For general formulas provided herein, where no stereochemistry is indicated, all possible stereoisomers are included in such structures. Chemical formulae that indicate stereochemistry may not be limited solely to the stereoisomers depicted, unless context indicates otherwise. For certain embodiments, at least one of $R_1$-$R_4$ is a heterocycle, such as furan, pyrrole, or thiophene. In other embodiments, at least one of $R_1$-$R_4$ is an aryl group coupled to the 3-membered ring by a linker atom, functional group, or other moiety. In yet other embodiments, the 3-membered ring does not include an amide bonded thereto, but does include at least one amine, as opposed to milnacipran, which has both an amine and an amide bonded to a cyclopropane ring.

For yet other embodiments, disclosed compounds have two or more of these features in combination. For example, certain compounds within the scope of the present disclosure have a formula

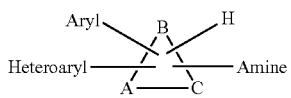

where A-C again independently are carbon, nitrogen, oxygen or sulfur. This general formula does not indicate position of the various groups on the 3-membered ring, nor the stereochemistry, as such groups can be attached to the ring structure at any of the available positions in all possible geometric and spatial combinations. For certain working embodiments, the bond connectivity was as shown below:

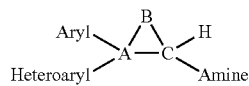

Certain amine substituents have a formula —$NR_1R_2$ where $R_1$ and $R_2$ independently are aliphatic, aryl or hydrogen, particularly lower alkyl or hydrogen. The amine nitrogen may be directly bonded to the three-membered ring, or separated from the ring by a spacer, such as by one or more carbon (e.g. methylene group or groups) and/or heteroatoms. 3-membered rings having heteroatoms bonded directly thereto may not be stable. For example, a cyclopropane ring with an —$NH_2$ group directly bound thereto may undergo ring opening. Compounds having this structure can be obtained by using any suitable method as would be known or discernable to a person of ordinary skill in the art, such as by excising a methylene group attached at position C. Oxidation of an allylic alcohol at position C can provide a carboxylic acid moiety. This carboxylic acid can then be converted to an acyl azide using conditions known to a person of ordinary skill in the art to produce such a moiety. For example, in some embodiments, the carboxylic acid can be converted first to an acyl halide by reaction of the carboxylic acid with reagents, such as acid chlorides; more typically by reaction with reagents, such as $SOCl_2$ and $POCl_3$. Other embodiments can involve forming mixed anhydrides, which can then be converted to an acyl azide. These embodiments employ esterifying reagents known to a person of ordinary skill in the art to form a mixed anhydride, such as ClC(O)OEt. The esterifying reagents can react with the carboxylic acid to form a mixed anhydride. The acyl halide or mixed anhydride can then react with an alkali azide or trimethylsilyl azide to form the acyl azide product. A typical alkali azide reagent is sodium azide. The acyl azide product can also be formed by reacting a carboxylic acid with diphenyl phosphoryl azide (DPPA). Once the acyl azide has been formed, it can be heated at a temperature effective to promote rearrangement of the acyl azide, thus producing an isocyanate intermediate. The isocyanate intermediate can be transformed to an amine by either carrying out the reaction in water or adding water subsequently. A person of ordinary skill in the art will recognize that the conversion of a carboxylic acid to an acyl halide, followed by conversion to an acyl azide (or formation of an acyl azide directly from the carboxylic acid) and subsequent rearrangement to an isocyanate is known as a Curtius rearrangement. Any embodiment of a compound satisfying a chemical formula provided herein that is sufficiently stable for administration, such as by ingestion, or which results in a pharmaceutically acceptable derivative upon ingestion is within the scope of the present disclosure.

Compounds having an aryl group coupled to the 3-membered ring include those having a formula:

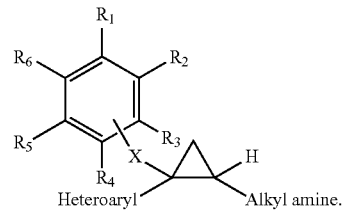

At least one of $R_1$-$R_6$ is replaced by X. Remaining $R_1$-$R_6$ independently are aliphatic, substituted aliphatic, amine, substituted amine, aryl, substituted aryl, cyclic, substituted cyclic, ether, halide, heteroaryl, substituted heteroaryl, heterocyclic, substituted heterocyclic, hydrogen, hydroxyl, or are carbon atoms, oxygen atoms, nitrogen atoms or sulfur atoms in a second aryl, cyclic, heteroaryl or heterocyclic ring. X is an atom, such as a carbon atom (e.g. methylene unit or units), or a heteroatom, such as oxygen or sulfur, a functional group, such as a carbonyl or amine, or combinations thereof. X also is indicated as being position independent with respect to ring position.

Particular examples of such compounds include those having a formula

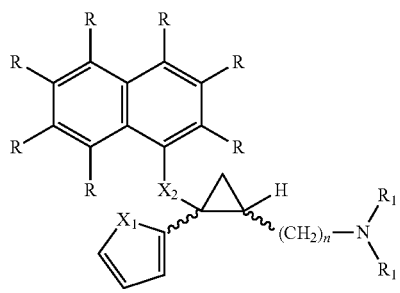

where n is from 1 to 10, R groups are as stated above, $R_1$ substituents independently are aliphatic, substituted aliphatic, aryl, substituted aryl, cyclic, substituted cyclic, heteroaryl, substituted heteroaryl, heterocyclic, substituted heterocyclic, hydrogen, or are atoms in a ring, $X_1$ is carbon, oxygen, nitrogen or sulfur, and $X_2$ is a spacer that links the aryl group to the cyclopropane ring.

Certain compounds where $X_2$ is oxygen have a formula:

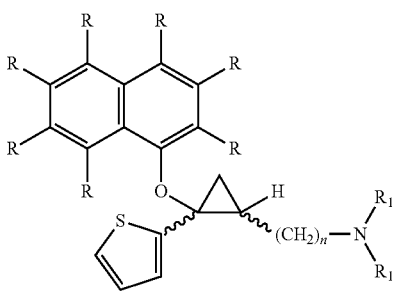

where n, R and $R_1$ substituents are as stated above.

Exemplary working compounds have the following formulas, with the understanding that such compounds often are formulated as pharmaceutically acceptable salts:

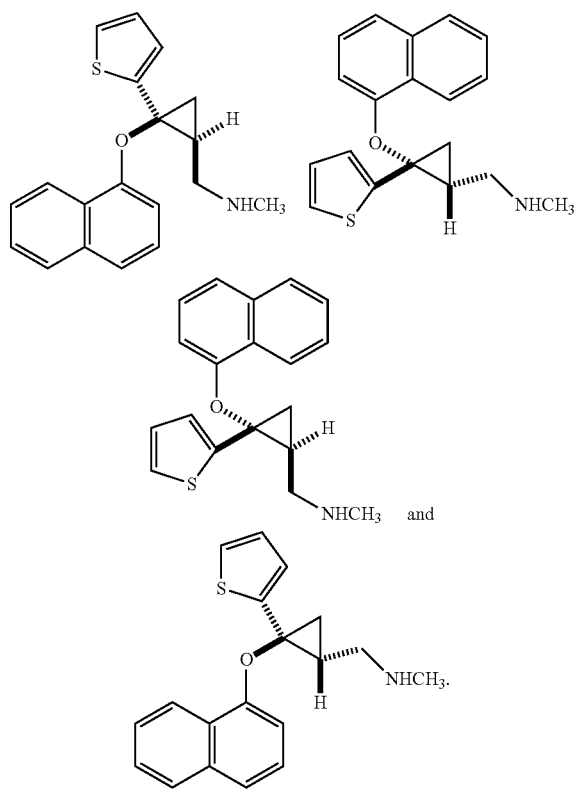

Disclosed embodiments of the present disclosure also concern compositions comprising a compound as disclosed herein, including enantiomerically enriched, or substantially enantiopure compounds, or combinations of compounds, including racemic mixtures of compounds. The composition also may comprise any material, or combinations of materials, now known or hereafter developed that is useful for formulating therapeutic compositions.

Embodiments of a method for treating a subject also are disclosed. Disclosed embodiments comprise administering a disclosed compound, or compounds, or a composition comprising the compound or compounds, to a subject. A person of ordinary skill in the art can determine an effective amount of a compound, or composition comprising a compound, useful for treating maladies. It currently is believed that the method is suitably practiced by administering from greater than 0 up to at least 300 milligrams of the compound to a subject, more typically the compound is administered at a dose of at least as low as about 40 mg/day up to a dose of about 300 mg/day. The compound, or composition comprising the compound, can be administered once daily, or multiple doses of the compound or composition may be administered to a subject per day.

Embodiments of a method for making disclosed compounds also are provided. A first working embodiment involved forming an ester by reacting a heteroaryl carboxylic acid with an aryl alcohol; performing a methylenation reaction on the ester to produce an olefin; and forming a cyclopropane from the olefin. Certain compounds comprise a carboxylic acid, or an activated form of a carboxylic acid, such as an acid chloride, or an ester. The method may further comprise forming an amide from the carboxylic acid or ester, and reducing the carbonyl functionality of the acid or ester to a methylene moiety. Methylenation can be done using a Tebbe reaction or a Wittig reaction. The cyclopropane can be formed by treating the olefin with a diazo compound, such as a diazoalkylacetate.

A second disclosed embodiment is useful for making enantiomerically enriched, or substantially enantiopure, compounds. This embodiment comprises performing an unsymmetric cyclopropanation reaction, such as a Simmons Smith reaction or a Charette asymmetric cyclopropanation. See, for example, Howard Ensign Simmons, Jr.; Smith, R. D. "4-Substituted-2,3,5-pyrrolidinetriones,"*J. Am. Chem. Soc.* 1958, 80:532; Charette, A. B.; Juteau, H. "Design of Amphoteric Bifunctional Ligands: Application to the Enantioselective Simmons-Smith Cyclopropanation of Allylic Alcohols," *J. Am. Chem. Soc.* 1994, 116, 2651; Hideyo Takahashi, Masato Yoshioka, Masaji Ohno and Susumu Kobayashi "A catalytic enantioselective reaction using a C2-symmetric disulfonamide as a chiral ligand: cyclopropanation of allylic alcohols by the $Et_2Zn$—$CH_2I_2$-disulfonamide system," Tetrahedron Letters 1992, 33 (18): 2575-2578; and Hiroaki Shitama and Tsutomu Katsuki "Asymmetric Simmons-Smith Reaction of Allylic Alcohols with Al Lewis Acid/N Lewis Base Bifunctional Al(Salalen) Catalyst,"*Angew. Chem. Int. Ed.*, 2008, 47: 2450. Each of these publications is incorporated herein by reference. For asymmetric synthesis, certain disclosed embodiments concerned making a pharmaceutically acceptable compound having a formula

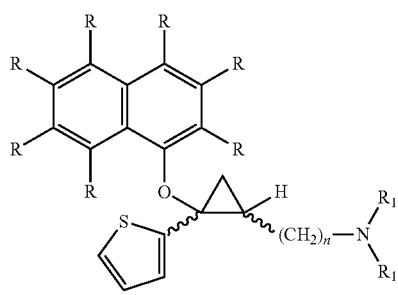

or a pharmaceutically acceptable salt thereof, where n, and the R and $R_1$ groups are as stated above. Disclosed embodiments of the method comprised providing a first compound having a formula

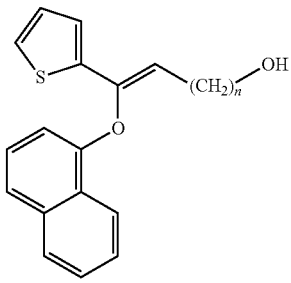

or a second compound having a formula

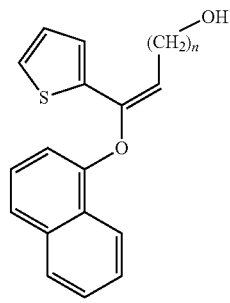

This disclosed embodiment of the method then comprises performing an asymmetric cyclopropanation reaction on the first or second compound to form a cyclopropanated compound. The hydroxyl functional group of the cyclopropanated compound is converted into an amide functional group, such as by first oxidizing the hydroxyl functional group to a carboxylic acid and reacting the carboxylic acid, or an activated version thereof, such as an acid chloride, with an alkyl amine. The carbonyl functional group may then be reduced to a methylene group. The method also may comprise forming a pharmaceutically acceptable salt of the compound.

The foregoing and other objects, features, and advantages of the invention will become more apparent from the following detailed description, which proceeds with reference to the accompanying figures.

DETAILED DESCRIPTION

I. Introduction and Definitions

Figure 1:
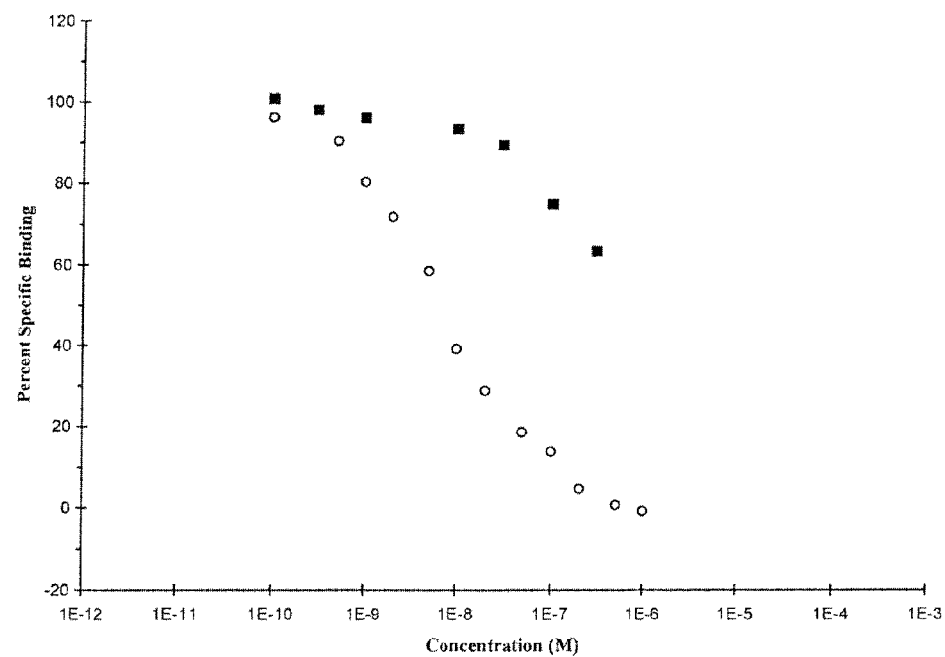
FIG. 1 is a specific binding (%) versus concentration curve (M) for a norepinephrine transporter assay used to determine $IC_{50}/Ki$ comparing an exemplary compound (DWJW002, solid squares) and desipramine (empty circles).
Figure 2:
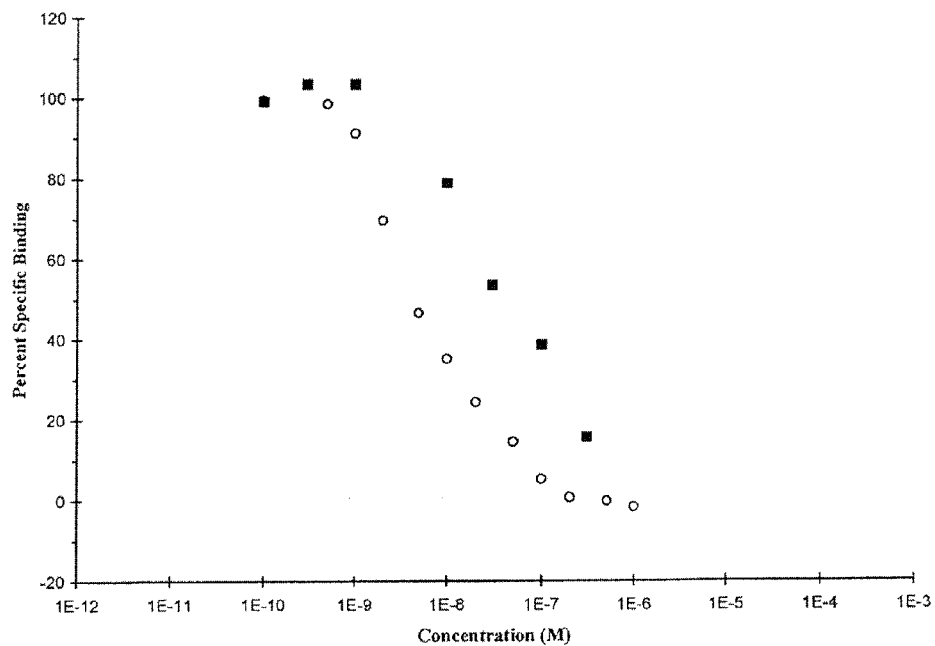
FIG. 2 is a specific binding (%) versus concentration curve (M) for a norepinephrine transporter assay used to determine $IC_{50}/Ki$ comparing an exemplary compound (DWJW003, solid squares) and desipramine (empty circles).
Figure 3:
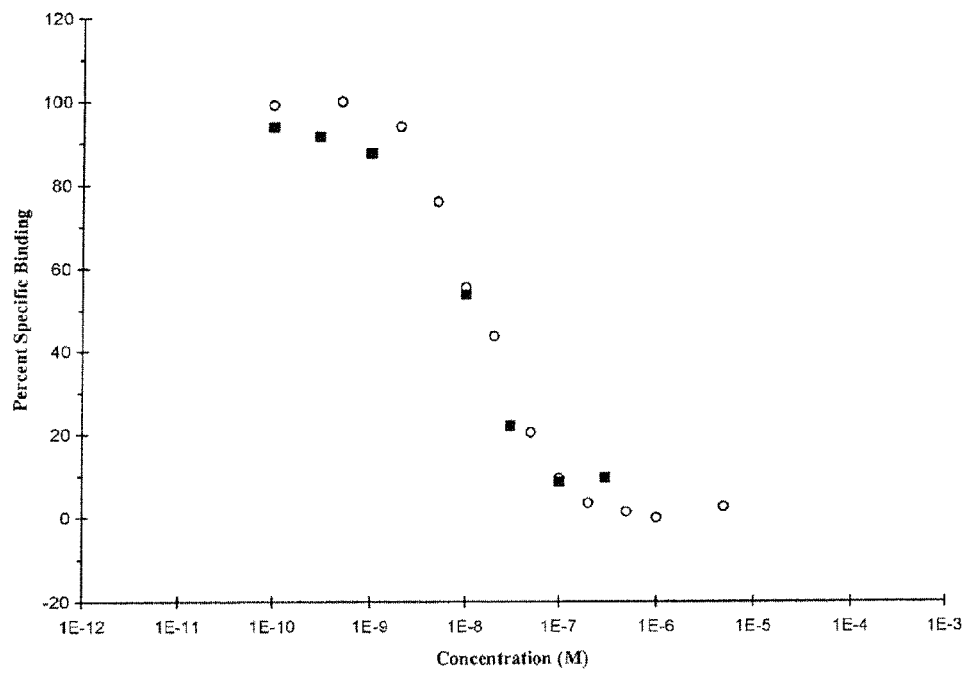
FIG. 3 is a specific binding (%) versus concentration curve (M) for a serotonin transporter assay used to determine $IC_{50}/Ki$ comparing an exemplary compound (DWJW002, solid squares) and imipramine (empty circles).
Figure 4:
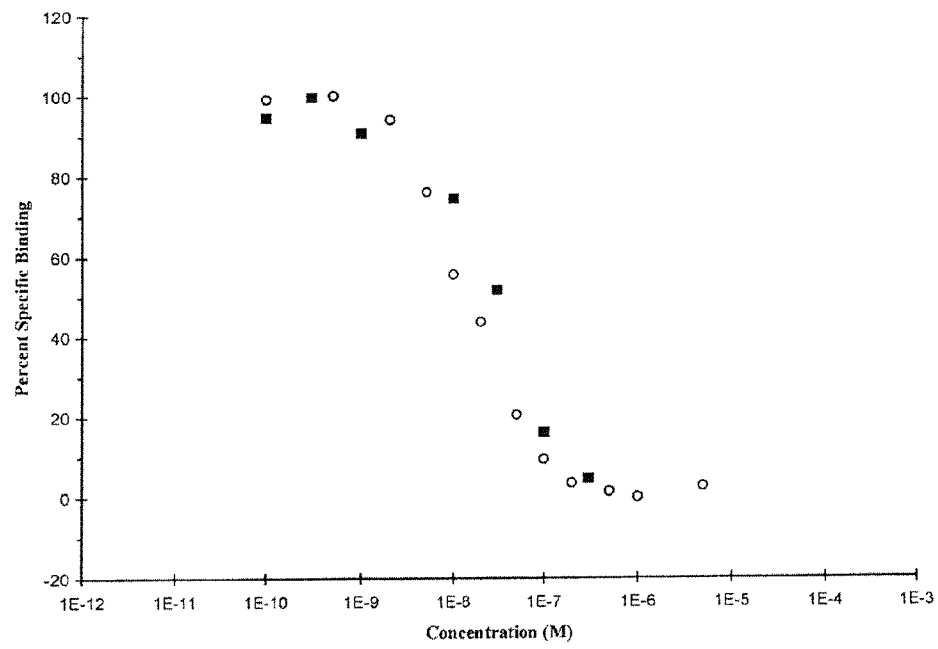
FIG. 4 is a specific binding (%) versus concentration curve (M) for a serotonin transporter assay used to determine $IC_{50}/Ki$ comparing an exemplary compound (DWJW003, solid squares) and imipramine (empty circles).
Figure 5:
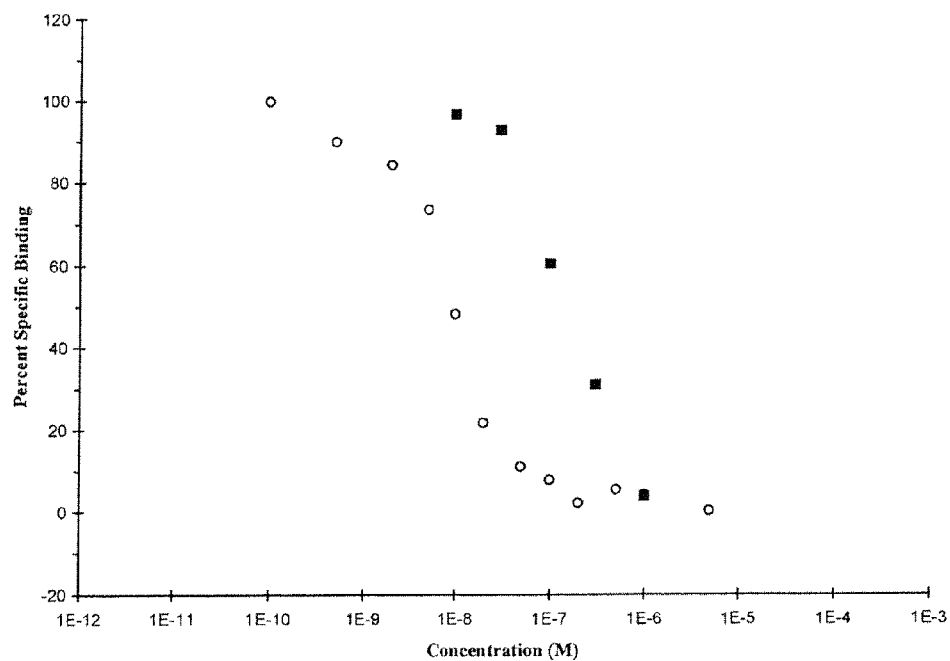
FIG. 5 is a specific binding (%) versus concentration curve (M) for a dopamine transporter assay used to determine $IC_{50}/Ki$ comparing an exemplary compound (DWJW002, solid squares) and GBR12909 (empty circles).
Figure 6:
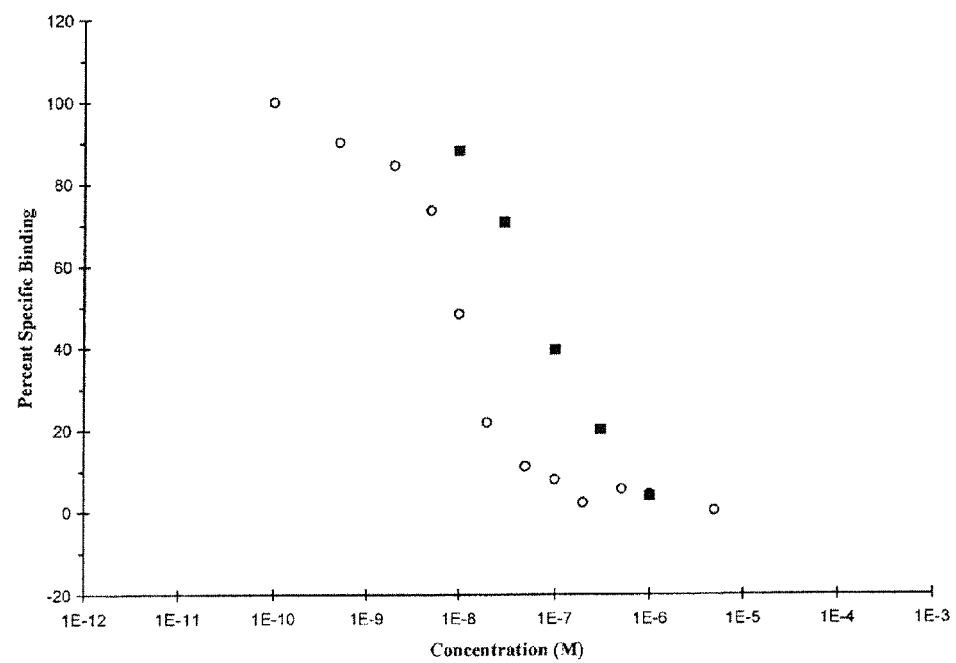
FIG. 6 is a specific binding (%) versus concentration curve (M) for a dopamine transporter assay used to determine $IC_{50}/Ki$ comparing an exemplary compound (DWJW003, solid squares) and GBR12909 (empty circles).

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all molecular weight or molecular mass values, given for compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Active agent: Any therapeutic or diagnostic agent now known or hereinafter discovered that can be formulated as described herein. Active agents also can be used in combinations, such as a known therapeutic, or therapeutics, used in combinations with a therapeutic or therapeutics disclosed herein. Examples of known therapeutics, without limitation, are listed in U.S. Pat. No. 4,649,043, which is incorporated herein by reference. Additional examples are listed in the American Druggist, p. 21-24 (February, 1995).

Acyl: A group of the formula RC(O)— wherein R is an organic group.

Administration: Delivering one or more therapeutics or composition comprising one or more therapeutics to a subject by any known means including, but not limited to, nasally, orally, parenterally (including subcutaneous, intramuscular, intravenous and intradermal), rectally, topically (including buccal and sublingual) and/or vaginally.

Aliphatic: A substantially hydrocarbon-based compound, including alkanes, alkenes and alkynes, and further including straight- and branched-chain arrangements, and all stereo and position isomers as well.

Alkenyl: An alkenyl group is an optionally substituted hydrocarbon group of 2 to 24 carbon atoms and structural formula containing at least one carbon-carbon double bond.

Alkoxy: An alkoxy group is represented by the formula —OR, wherein R can be an alkyl group, optionally substituted with an alkenyl, alkynyl, aryl, aralkyl, cycloalkyl, halogenated alkyl, or heterocycloalkyl group as described herein. A particular example of an alkoxy group includes, without limitation, methoxy (—OMe).

Alkyl: An optionally substituted branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, undecyl, dodecyl, tetradecyl, hexadecyl, eicosyl, tetracosyl and the like. A "lower alkyl" group is a saturated branched or unbranched hydrocarbon having from 1 to 10 carbon atoms. The terms "halogenated alkyl" or "haloalkyl group" refer to an alkyl group as defined above with one or more hydrogen atoms present on these groups substituted with a halogen (F, Cl, Br, I). The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom in the ring such as, but not limited to, nitrogen, oxygen, sulfur, or phosphorous. In contrast with heterocycloalkyl groups, the term "alicyclic" refers to a group that is both aliphatic and cyclic. Such groups contain one or more all-carbon rings which may be either saturated or unsaturated, but do not have aromatic character. Alkyl groups, including cycloalkyl groups and alicyclic groups optionally may be substituted. The nature of the substituents can vary broadly. Typical substituent groups useful for substituting alkyl groups in the presently disclosed compounds include halo, fluoro, chloro, alkyl, alkylthio, alkoxy, alkoxycarbonyl, arylalkyloxycarbonyl, aryloxycarbonyl, cycloheteroalkyl, carbamoyl, haloalkyl, dialkylamino, sulfamoyl groups and substituted versions thereof.

Alkynyl: An optionally substituted hydrocarbon group of 2 to 24 carbon atoms and a structural formula containing at least one carbon-carbon triple bond.

Amide: A group represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

Amine or Amino: An amine is a chemical structure comprising a nitrogen atom with three or four substituents. The nitrogen atom may be neutral or positively charged. Amines also may be represented structurally by the fragment —NR$_2$ or —NR$_3^+$, where R is hydrogen, aliphatic, alkyl, heteroaliphatic or heteroalkyl where the aliphatic or alkyl chains containing one or more heteroatoms, aryl, heteroaryl and combinations thereof. "Amine" also specifically includes amino (i.e. —NH$_2$), ammonium (i.e. —NH$_3^+$) and quaternary amines (i.e. —NR$_3^+$). The designation of amine in the general formula does not necessarily indicate that the nitrogen atom is directly bonded to a structure, nor does it preclude such a direct bond. For example, a general formula showing an amine directly bound to a cyclopropane ring would encompass structures with an aliphatic, alkyl, aryl, heteroaryl or other chemical structure acting as a spacer between the nitrogen atom and another substituent such as a cyclopropane ring. Certain general formulas used herein may specifically show a spacer.

Analog: An analog differs in chemical structure from a reference compound, for example by incrementally differing in chemical structure, such as a difference in alkyl chain length), a molecular fragment, a structure that differs by one or more functional groups, and/or a change in ionization. Structural analogs often are found using quantitative structure activity relationships (QSAR). See, for example, techniques such as those disclosed in Remington, *The Science and Practice of Pharmacology,* 19th Edition (1995), chapter 28.

Animal: Living, multi-cellular vertebrate organisms.

Aryl: Refers to any carbon-based aromatic group including, but not limited to, benzene, naphthalene, etc. The term "aromatic" may also include "heteroaryl," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, aliphatic, including alkyl, alkynyl, alkenyl, substituted aliphatic, aryl, halide, nitro, amino, ester, ketone, aldehyde, hydroxy, carboxylic acid, or alkoxy, or the aryl group can be unsubstituted.

Arylalkyl: A compound, or a radical thereof ($C_7H_7$ for toluene) as a substituent bonded to another group, particularly other organic groups, containing both aliphatic and aromatic structures.

Carbonyl: A group of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

Carboxyl: A —COO— group, which may be either —COOH or —COOR, which also may be referred to as substituted carboxyl, wherein R is aliphatic, heteroaliphatic, alkyl, heteroalkyl, aralkyl, aryl or the like.

Cyclic: Designates a substantially hydrocarbon, closed-ring compound, or a radical thereof. Cyclic compounds or substituents also can include one or more sites of unsaturation, but does not include aromatic compounds. One example of such a cyclic compound is cyclopentadieneone.

Binding affinity: The tendency of one molecule to bind (typically non-covalently) with another molecule, such as the tendency of a member of a specific binding pair for another member of a specific binding pair. A binding affinity can be measured as a binding constant.

Controlled release: Includes timed release, sustained release, pulse release, delayed release and all terms which describe a release pattern other than immediate release.

Derivative: A derivative is a biologically active molecule derived from a base structure.

Diastereomers: Pairs of isomers that have opposite configurations at one or more chiral centers but that are not mirror images of each other.

Effective amount: An amount of a diagnostic or therapeutic agent that is useful for producing a desired effect.

Enantioenriched: Refers to a mixture comprising an excess of one enantiomer but not to the exclusion of the other enantiomer.

Enantiomers: Stereoisomers that are non-superimposable complete mirror images that rotate plane polarized light by equal amounts but in opposite directions.

Enantiopure: Only one of two possible enantiomers is present.

Enantiomeric excess or ee: A measure of how much of one enantiomer is present in a mixture comprising enantiomers compared to the other. For example, in a sample with 40% ee in an R enantiomer, the remaining 60% is racemic with 30% of the R enantiomer and 30% of the S enantiomer. The total amount of the R enantiomer in the mixture therefore is 70%.

Halide or Halo: Refers to a fluoro, chloro, bromo or iodo substituent, and most typically in the present compounds refers to a fluoro or chloro group.

Heteroaryl: Refers to an aromatic, closed-ring compound, or radical thereof as a substituent bonded to another group, particularly other organic groups, where at least one atom in the ring structure is other than carbon, and typically is oxygen, sulfur and/or nitrogen.

Heterocyclic: Refers to a closed-ring compound, or radical thereof as a substituent bonded to another group, particularly other organic groups, where at least one atom in the ring structure is other than carbon, and typically is oxygen, sulfur and/or nitrogen.

Hydroxyl: A moiety represented by the formula —OH.

Hydroxyalkyl: An alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can be substituted with aryl, optionally substituted heteroaryl, aralkyl, halogen, hydroxy, alkoxy, carboxyalkyl, optionally substituted cycloalkyl, optionally substituted cycloalkenyl and/or optionally substituted heterocyclyl moieties.

Inhibit: Inhibiting the full development of a disease or condition, for example, in a subject who is at risk for a disease, or to decrease, limit or block the action or function of a molecule.

Lower: Refers to compounds having 10 or fewer carbon atoms in a chain, including all geometric, position and stereoisomers.

Mammal: Includes both human and non-human mammals.

Mimetic: A molecule that mimics the biological activity of another molecule.

Pharmaceutically Acceptable Carriers: Pharmaceutically acceptable carriers (vehicles) useful for the presently disclosed compositions may be known carriers, but future developed carriers also may be used with the embodiments of the present disclosure. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules.

The nature carrier selected for a particular composition may depend on the particular mode of administration employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents, for example sodium acetate or sorbitan monolaurate, and the like.

Prodrug: Any molecule that undergoes in vivo metabolic conversion to one or more pharmacologically active compounds.

Purified: The term "purified" does not require absolute purity; rather, it is intended as a relative term. Thus, for example, a purified compound is one that is isolated in whole or in part from proteins or other contaminants. Generally, substantially purified compounds comprise more than 80% of all macromolecular species present in a preparation prior to admixture or formulation with other desired therapeutic formulation components, such as a pharmaceutical carrier, excipient, buffer, absorption enhancing agent, stabilizer, preservative, adjuvant or other co-ingredient in a complete pharmaceutical formulation for therapeutic administration. More typically, the active compound is purified to represent greater than 90%, often greater than 95%, of all macromolecular species present in a purified preparation prior to admixture with other formulation ingredients. In other cases, the purified preparation may be essentially homogeneous, wherein other macromolecular species are not detectable by conventional techniques.

Racemic: A mixture of equal parts of an optically active isomer and its enantiomer and having a net zero rotation of plane-polarized light.

Spacer: A spacer is any atom, or group of atoms, that spaces one moiety from another. For example, certain disclosed embodiments concern compounds having a three-membered ring, such as a cyclopropane, aziridine, epoxide, or episulfide. Such ring systems typically do not include a heteroatom directly bonded to the 3-membered ring, as this may promote ring opening. Thus, heteroatoms typically are spaced from the three membered ring by a spacer, including but not limited to a carbon atom, such as a methylene unit.

Subject: Living multi-cellular vertebrate organisms, a category that includes human and non-human mammals. The methods and compounds disclosed herein have equal applications in medical and veterinary settings. Therefore, the general term "subject" is understood to include all animals, including, but not limited to, humans or veterinary subjects, such as other primates and felines.

Substituted: A base compound, such as an aryl group or compound, aliphatic group or compound, a cyclic group or compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as an aryl group, a cyclic group, a heteroaryl group or a heterocyclic group.

Sulfide: A moiety represented by the formula —SR, wherein R can be an alkyl group, optionally substituted with an alkenyl, alkynyl, aryl, aralkyl, cycloalkyl, halogenated alkyl, or heterocycloalkyl group as described above. The term sulfhydryl is used to refer to the formula —SR wherein R is H.

Sulfonyl: A group of the formula —$SO_2$—. The sulfonyl group can be further substituted with a variety of groups to form, for example, sulfonic acids, sulfonamides, sulfonate esters and sulfones.

Tablet: Includes all compacted, molded, or otherwise formed materials without limitation in terms of sizes or shapes, and all methods of preparation. Thus, as one common example, compressed or molded shapes known as caplets are included.

Therapeutically Effective Amount: A quantity of a specified agent sufficient to achieve a desired effect in a subject being treated with that agent. For example, this may be the amount of a compound or composition thereof useful for increasing resistance to, preventing, ameliorating, and/or treating infection and disease. Ideally, a therapeutically effective amount of an agent is an amount sufficient to increase resistance to, prevent, ameliorate, and/or treat infection and/or disease and without causing a substantial cytotoxic effect in the subject. The effective amount of an agent useful for increasing resistance to, preventing, ameliorating, and/or treating infection and/or disease in a subject will be dependent on the subject being treated, the severity of the affliction, and the manner of administration of the therapeutic composition.

Treatment: A therapeutic intervention that ameliorates a sign or symptom of a disease or pathological condition after it has begun to develop. As used herein, "ameliorating or ameliorates," with reference to a disease, pathological condition or symptom, refers to any observable beneficial effect of the treatment, such as delayed onset of clinical symptoms in a susceptible subject, reduced severity of at least one or all clinical symptoms, slower progression, reduced relapses, improved health or well-being of the subject, or by other parameters well known in the art that are specific to a particular disease.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting. All publications, patent applications, patents, and other references mentioned herein are incorporated by reference in their entirety, unless the context clearly indicates otherwise.

II. Compounds

Compounds of the present disclosure are characterized by having a 3-membered ring, such as a cyclopropane ring or a heteroatom derivative thereof. Thus, certain disclosed embodiments of the present disclosure concern compounds having a formula:

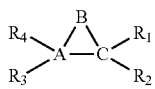

These compounds also can be described by a formula that indicates relative spatial arrangements, such as with the following formula:

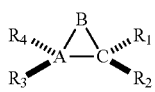

With reference to these first general formulas, A-C independently are selected from carbon, nitrogen, oxygen or sulfur, are most typically carbon and nitrogen, and even more typically carbon. A ring having all carbon atoms is a cyclopropane, as shown below.

A ring having 1 nitrogen atom and 2 carbon atoms is an aziridine; a ring having 1 oxygen atom and 2 carbon atoms is an ethylene oxide or epoxide; and a ring having 1 sulfur atom and 2 carbon atoms is a thiirane or an episulfide. $R_1$-$R_4$ for these general formulas independently are aliphatic (alkyl, alkenyl, and alkynyl substituents), substituted aliphatic, amine, substituted amine, aryl, substituted aryl, cyclic, substituted cyclic, halide, heteroaryl, substituted heteroaryl, heterocyclic, substituted heterocyclic, hydrogen or hydroxyl. Substituted aliphatic includes all functional group substitutions known to a person of ordinary skill in the art, including by way of example and without limitation, alcohols, amines, aldeyhdes, carboxylic acids, esters, ethers, epoxides, halogenated aliphatic compounds, ketones, and heteroatom derivatives thereof, such as sulfur derivatives, including thiols and sulfides.

For certain disclosed embodiments, at least one of $R_1$-$R_4$ is heteroaryl. For other disclosed embodiments, at least one of $R_1$-$R_4$ is an aryl group coupled to the 3-membered ring by a linker. For yet other disclosed embodiment, none of the substituents is an amide. And certain embodiments have combinations of these possible substituents.

$R_1$-$R_4$ may be the same, but most typically are different, and may define stereoisomers, such as enantiomers or diastereomers. Particular examples of aryl substituents include phenyl, naphthyl, anthracenyl, phenanthrenyl, etc. Such aryl groups also can be substituted, such as with aliphatic groups (e.g., toluene), amine, other aryl groups, halides, heteroaliphatic, such as alcohols and substituted amines, hydroxyl, etc. Heteroaryl compounds include one or more heteroatoms in a ring, including heteroatoms such as oxygen, nitrogen or sulfur, particularly nitrogen, e.g. pyridine, quinoline, isoquinoline, etc. Particular examples of heteroaryl substituents include 5- and 6-membered rings, particularly 5-membered rings, such as furan, pyrrole, and thiophene.

Thus, based on the above, another general formula useful for describing embodiments of active compounds of the present disclosure is as follows:

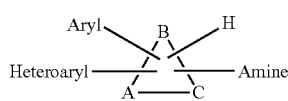

wherein A-C independently are carbon, nitrogen, oxygen or sulfur. This general formula does not indicate specific substituent connectivity to the 3-membered ring to establish that the various groups may be attached at any of the available positions and in all possible spatial arrangements and stereoconfigurations. With reference to certain working embodiments, the bond connectivity was as shown below:

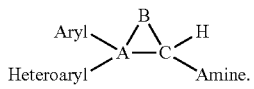

A person of ordinary skill in the art also will appreciate that an additional atom, or groups of atoms, may be interspersed between those substituents indicated in this general formula. For example, a linker atom, or group of atoms, such as one or more carbon atoms, or one or more heteroatoms, such as oxygen, may "link" the designated substituents to the 3-membered ring.

With reference to this and the prior general formulas, exemplary aryl compounds include phenyl, naphthyl, anthracenyl, etc. Substituted aryl compounds also are useful including, by way of example and without limitation:

Halogenated Compounds:

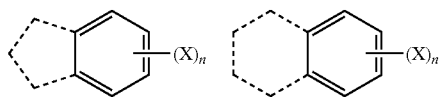

where n is 1 to the number of available ring positions, X independently is halide, particularly fluorine and/or chlorine, and most typically chlorine, and where the dashed lines indicate the potential for additional rings fused to the illustrated phenyl ring, with fused [4.3.0] and [4.4.0] ring systems provided to illustrate the possibility of additional rings. Any additional fused rings may be cyclic or aryl.

Aliphatic Substituted Aryl:

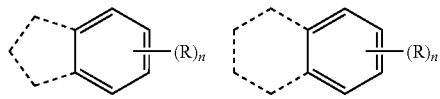

where n is 1 to the number of available ring positions, and R independently is aliphatic, particularly lower alkyl, such as methyl and ethyl.

Halogenated Alkyl Substituted Aryl:

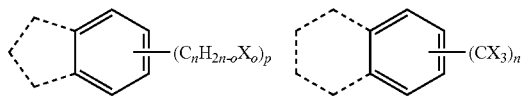

where n is from 1 to about 20, more typically from 1 to about 10, and even more typically from about 1 to about 5, o is from 1 to the number of hydrogen atoms, p is from 1 to the number of available ring positions, and X independently is halide, particularly fluorine and/or chlorine, such as trifluoromethyl.

Alkoxy Substituted Aryl:

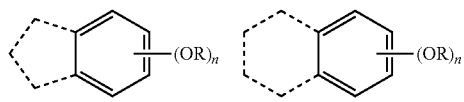

where n is 1 to the number of available ring positions, R independently is aliphatic, particularly lower alkyl, such as methyl and/or ethyl.

A person of ordinary skill in the art also will appreciate that heteroaryl derivatives of the aryl substituents disclosed above also can be used to make compounds according to the present disclosure. Thus, suitable heteroaryl substituents include those where one or more carbon atoms are substituted with a heteroatom, including by way of example, oxygen, nitrogen and sulfur. Exemplary heteroaryl structures include the formulas illustrated below.

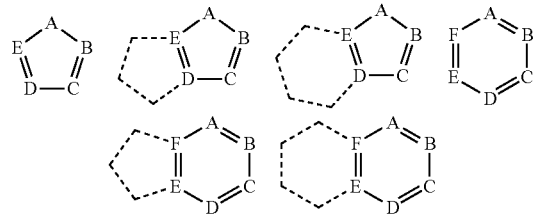

At least one of A-F is nitrogen, oxygen or sulfur, and remaining A-F atoms independently are carbon, nitrogen, oxygen or sulfur. Specific examples of heteroaryl structures include:

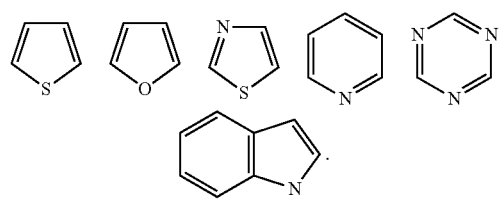

Cyclic structures include, but are not limited to, cyclopropane, cyclobutane, cyclopentane, cyclohexane, cycloheptane, etc. Cyclic moieties also can be substituted, such as with aliphatic, amine, halide and/or hydroxyl substituents.

Heterocyclic compounds also can be suitable moieties for making disclosed compounds. For example, heterocyclic structures include:

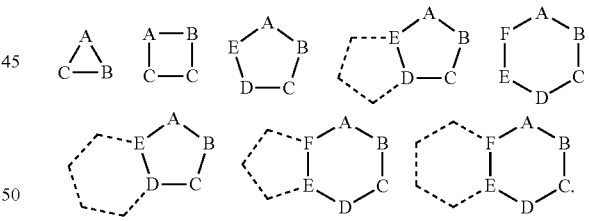

where at least one of A-F is nitrogen, oxygen or sulfur, and remaining A-F atoms independently are carbon, nitrogen, oxygen or sulfur. Fused rings may be cyclic or aryl. Specific examples of heterocyclic structures include:

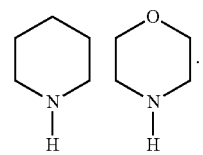

Exemplary amine compounds include —NH$_2$, and substituted amines, including by way of example: aliphatic amines, having a formula —NR$_1$R$_2$, where at least one of R$_1$ and R$_2$ is an aliphatic group, including alkyl, alkenyl and alkynyl groups, particularly aliphatic groups having from about 1 to about 20 carbon atoms, typically from about 1 to about 10 carbon atoms, and more typically from about 1 to about 5 carbon atoms, in either straight or branched chain configurations; cyclic groups; substituted cyclic groups; or hydrogen. Certain embodiments concern alkyl amines, such as methyl amine, dimethyl amine, ethyl amine, diethyl amine, ethyl methyl amine, etc. The amine substituent also may be a heterocyclic amine. Thus, the amine may be an aliphatic amine or substituted aliphatic amine, with disclosed compounds having a formula,

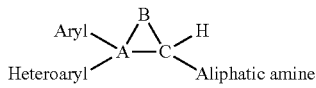

or an aryl amine or heteroaryl amine, having a formula,

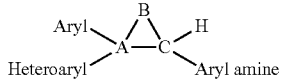

or a cyclic amine, having a formula:

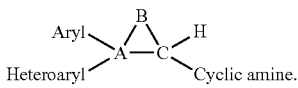

Additionally, the amine may be a salt, such as a tri-substituted ammonium moiety, with the formula —NR$_1$R$_2$R$_3$$^+$, where R$_1$-R$_3$ are as stated above for R$_1$ and R$_2$. The positively charged salt includes an atom or compound (e.g. counter ion) possessing a negative charge sufficient to balance the positive charge. By way of example and without limitation, a counter ion might be a halogen ion, such as chloride, or an organic ion, such as trifluoroacetate.

In some embodiments, the amine is separated from the cyclic structure by a spacer. For example, the amine may be linked to the 3-membered ring by a number of intervening atoms, particularly if useful to maintain a cyclic structure at the time of administration of the compound, typically 1 to 10 atoms, generally 1 to 10 carbon atoms in cyclic, straight or branched chain configurations. Based on these considerations, yet another general formula that describes certain disclosed embodiments is as follows:

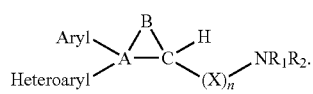

With reference to this formula, n is from 0 to at least 10, typically from 1 to about 5, and X is an optional spacer that spaces the amine nitrogen from the 3-membered ring. In certain embodiments, X is a methylene unit or units that space the amine nitrogen from the 3-membered ring.

Certain compounds within the scope of the present disclosure have a formula:

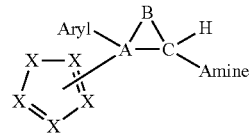

where A-C and X independently are carbon, nitrogen, oxygen or sulfur. The five-membered ring generally includes at least one heteroatom, as indicated below with reference to a cyclopropane derivative, although a person of ordinary skill in the art will appreciate that the ring structure can include 2 or more heteroatoms that are the same or different.

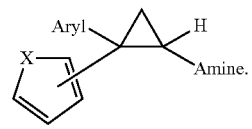

These general formulae include bonds drawn from the 3-membered ring to the center of the heteroaryl compound, and not to a specific atom in the ring structure, to indicate that the 3-membered ring may be bonded to any ring position of the heteroaryl substituent. With reference to thiophene working embodiments, such structures typically have the following formula:

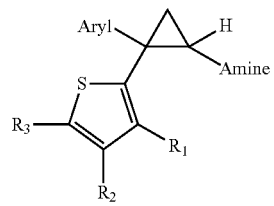

wherein R$_1$-R$_3$ independently are selected from hydrogen and aliphatic groups, and more typically hydrogen and lower alkyl groups.

Another general formula that describes certain disclosed compounds is as follows:

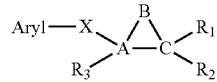

where again, A-C independently are carbon, nitrogen, oxygen or sulfur, most typically carbon and nitrogen, and even more typically carbon, R$_1$-R$_3$ are as stated above, and X is an atom, such as a carbon atom, nitrogen atom, oxygen atom or sulfur atom, a functional group or other spacer moiety that links the aryl group to the three membered ring. Particular exemplary compounds had the following structures

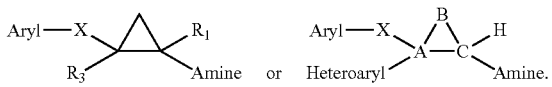

Certain embodiments of disclosed compounds having an X spacer and an aryl substituent are illustrated by the following formula:

19

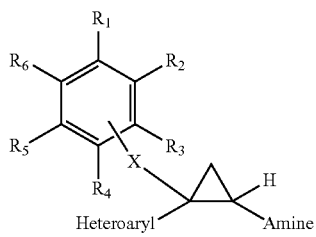

wherein $R_1$-$R_6$ independently are selected from aliphatic, substituted aliphatic, particularly alkyl or substituted alkyl, amine, substituted amine, aryl, substituted aryl, cyclic, substituted cyclic, halide, heteroaryl, substituted heteroaryl, heterocyclic, substituted heterocyclic, hydrogen or hydroxyl. A person of ordinary skill in the art also will appreciate that one of $R_1$-$R_6$ is replaced by X. Two of $R_1$-$R_6$ also may be atoms, including carbon atoms, oxygen atoms, nitrogen atoms or sulfur atoms, or combinations thereof, in a second aryl, cyclic, heteroaryl or heterocyclic substituent, such as fused ring systems, including by way of example and without limitation, naphthyl or anthracenyl. X is an atom, such as a carbon atom (e.g. methylene unit or units), a heteroatom, such as oxygen or sulfur, a functional group, such as a carbonyl or an amine, or combinations thereof. X also is indicated as being position independent with respect to ring position.

Another general formula for disclosed compounds is as follows.

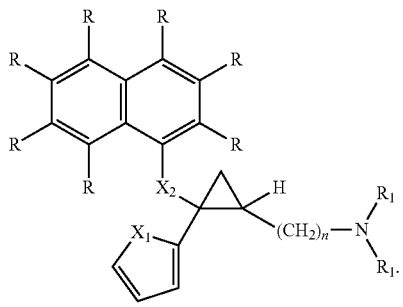

With reference to this general formula, n is from 1 to at least about 10. The R groups independently are aliphatic, substituted aliphatic, aryl, substituted aryl, cyclic, substituted cyclic, halide, heteroaryl, substituted heteroaryl, heterocyclic, substituted heterocyclic, hydrogen or hydroxyl, or two of the R substituents are carbon atoms, oxygen atoms, nitrogen atoms, sulfur atoms, or combinations thereof, in a second aryl, substituted aryl, cyclic, substituted cyclic, heteroaryl, substituted heteroaryl, heterocyclic or substituted heterocyclic substituent. Most typically the R groups are either hydrogen or lower alkyl. The $R_1$ substituents independently are aliphatic, substituted aliphatic, aryl, substituted aryl, cyclic, substituted cyclic, heteroaryl, substituted heteroaryl, heterocyclic, substituted heterocyclic, hydrogen, or are atoms in a ring. Most typically the $R_1$ substituents are hydrogen or lower alkyl. $X_1$ is a carbon, oxygen, nitrogen or sulfur atom. $X_2$ is a spacer that links the aryl group to the cyclopropane ring. A person of ordinary skill in the art will appreciate that these compounds can be formulated as pharmaceutically acceptable salts. A person of ordinary skill in the art also will appreciate that the preceding general formula does not indicate stereochemistry at each of the stereogenic centers. This is to indicate that all possible stereoisomers are included within the general formula.

20

Particular compounds of the present disclosure satisfy the following general formula, where the R and $R_1$ substituents are as stated above.

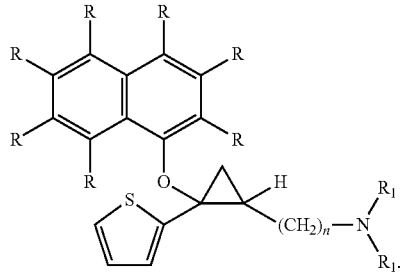

Compounds within this general formula include:

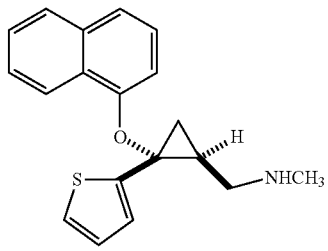

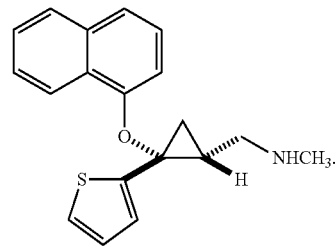

These compounds typically are formulated as salts, as indicated below by reference to the exemplary hydrochloride salt.

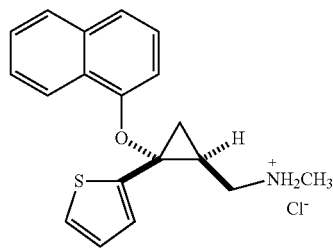

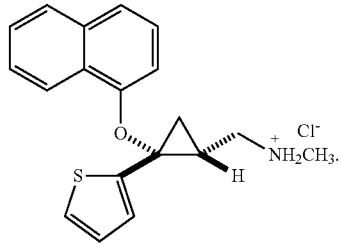

Compounds having these same substituents, but different stereochemistry, and salts thereof, also are within the scope of the present disclosure. These compounds include the following:

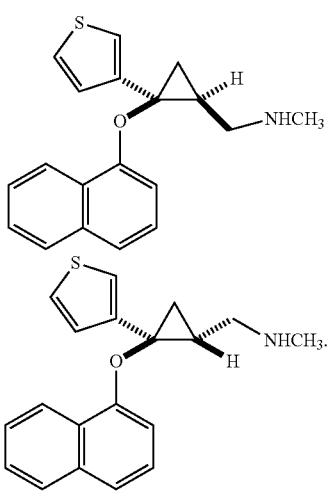

Compounds with the same substituents, but different substituent connectivity, also are within the scope of the present disclosure. Exemplary such compounds include:

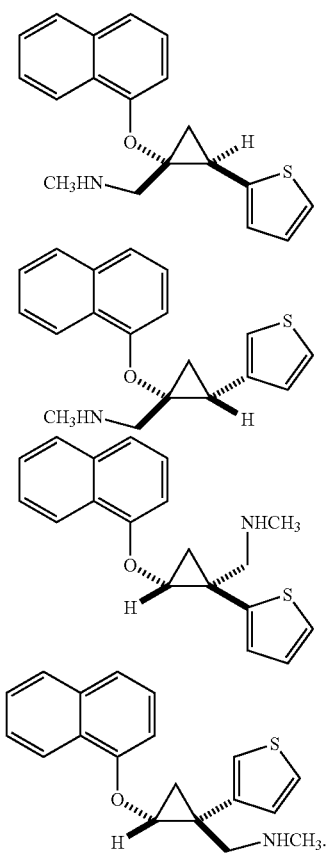

A person of ordinary skill in the art will appreciate that these compounds too can be formulated as salts.

III. Compositions Comprising Disclosed Compounds

Disclosed embodiments of the present disclosure also concern pharmaceutical or veterinary composition(s) that include one or more active compounds disclosed herein in combination or association with a pharmaceutically or veterinarily acceptable therapeutics, carriers, diluents, adjuvants, excipients, etc. Each such composition additive is "pharmaceutically acceptable" in the sense of being compatible with the other ingredients of the composition and substantially non-injurious to the subject.

Solely by way of example, and without limitation, compositions of the present disclosure may include, in addition to one or more of the compounds disclosed herein, carriers, diluents, adjuvants, excipients, at least one additional therapeutic, including known and future developed tricyclic antidepressants, known and future developed selective serotonin reuptake inhibitors, etc., binder, inert diluent, preservative, disintegrant (e.g. sodium starch glycollate, cross-linked sodium carboxymethyl cellulose) surface-active or dispersing agents, pregelatinized starch, dimethicone, gelatin, sodium lauryl sulfate, iron oxide, titanium dioxide, hydroxypropylmethyl cellulose, enteric coatings, thickening and/or gelling agents, aqueous or oily bases, emulsifying agents, stabilizing agents, dispersing agents, suspending agents, thickening agents, coloring agents, propellants such as chlorofluorocarbon (CFC), such as dichlorodifluoromethane, trichlorofluoromethane, or dichlorotetrafluoroethane, carbon dioxide, or other suitable gas, surfactants such as lecithin, lactose, starch, starch derivatives, polyvinylpyrrolidone (also referred to as povidone or PVP), cross-linked povidone, cocoa butter, isotonic solutions, anti-oxidants, buffers, bacteriostats and solutes that render the composition isotonic with the blood of the intended recipient, sweeteners, thickeners, flavoring agents, disintegrating agents, coating agents, preservatives, lubricants and/or time delay agents, lactose, glucose, aspartame, saccharin, corn starch, methylcellulose, xanthan gum, bentonite, alginic acid, agar, peppermint oil, oil of wintergreen, cherry, orange, raspberry, polymers or copolymers of acrylic acid and/or methacrylic acid and/or their esters, waxes, fatty alcohols, zein, shellac, glutan, sodium benzoate, vitamin E, alpha-tocopherol, ascorbic acid, methyl paraben, propyl paraben, sodium bisulphate, magnesium stearate, steric acid, sodium oleate, sodium chloride, talc, glyceryl monostearate, glyceryl distearate, or combinations thereof, suitable for producing pharmaceutical or veterinary compositions.

Disclosed compositions may be administered by any suitable route. Compositions may be particularly formulated for specific modes of administration.

Suitable compositions may be used in unit dosage forms and may be prepared by methods known to a person of ordinary skill in the art of pharmacy. In general, suitable compositions may be prepared by uniformly and intimately bringing into association at least one active agent as disclosed herein with any other material used to form the composition. The final product also may be shaped, such as by forming tablets. Compositions of the present disclosure suitable for oral administration may be formulated as capsules, sachets or tablets each containing a predetermined effective amount of the active agent. Compositions of the present disclosure also may be used as a solution or a suspension in an aqueous or non-aqueous liquid. Similarly, such compositions may be formulated as an oil-in-water liquid emulsion or a water-in-oil liquid emulsion. The active agent also may be formulated as a bolus, electuary or paste.

For compositions formulated as tablets, such tablets may be compression molded, optionally with one or more accessory ingredients. Tablets may be prepared by compressing in a suitable machine using the active ingredient in a free-flowing form such as a powder or granules. Tablet formulations also optionally may be mixed with a binder, inert diluent, preservative, disintegrant (e.g. sodium starch glycollate, crosslinked polyvinylpyrrolidone (also known as crosslinked povidone), cross-linked sodium carboxymethyl cellulose) surface-active or dispersing agents, or combinations thereof.

Additional specific ingredients include pregelatinized starch, dimethicone, gelatin, sodium lauryl sulfate, iron oxide, and titanium dioxide.

Therapeutic formulations, such as tablets, optionally may be coated, scored or delivery apertures may be formed therein. Therapeutic formulations also may be formulated to provide immediate release or controlled release of the active ingredient therein using, for example, hydroxypropylmethyl cellulose in varying proportions to provide the desired release profile. Formulations also optionally may include an enteric coating to provide therapeutic release in parts of the gut other than the stomach.

Disclosed formulations also may be administered topically. For topical administration to the epidermis, disclosed compounds according to the disclosure may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base. Such formulations generally also contain one or more emulsifying agents, stabilizing agents, dispersing agents, suspending agents, thickening agents, and/or coloring agents.

Formulations suitable for topical administration in the oral cavity include lozenges comprising active agent, such as lozenges in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Formulations also may be administered nasally. For such formulations, solutions or suspensions typically are applied directly to the nasal cavity by conventional means, for example with a dropper, pipette or spray. The formulations may be provided in single or multidose form as may be achieved by a patient administering an appropriate, predetermined volume of the solution or suspension, or in the case of a spray, by using a metering atomizing spray pump.

Administration to the respiratory tract also be may achieved using an inhaler device or an aerosol formulation in which the active agent is provided in a pressurized pack with a suitable propellant. Suitable propellants include a chlorofluorocarbon (CFC), such as dichlorodifluoromethane, trichlorofluoromethane, or dichlorotetrafluoroethane, carbon dioxide, or other suitable gas. The aerosol conveniently also may contain a surfactant such as lecithin.

Alternatively, active ingredients may be provided as a dry powder. For example, active agents may be formulated as a powder mix of the compound in a suitable powder base such as lactose, starch, starch derivatives such as hydroxypropylmethyl cellulose, polyvinylpyrrolidone, or combinations thereof.

The particle size of formulations also may be adjusted as desired. For example, in formulations intended for administration to the respiratory tract, including intranasal formulations, active compound(s) generally will have a small particle size of, for example, about 5 microns or less.

Active compound(s) also may be administered rectally. Compositions for rectal administration may be presented as a suppository with a suitable base comprising, for example, cocoa butter.

Compositions suitable for vaginal administration may be presented as pessaries, tampons, creams, gels, pastes, foams or spray formulations. Such formulations typically contain, in addition to the active agent, carriers as are known in the art.

Compositions suitable for parenteral administration include aqueous and non-aqueous sterile injection solutions. Such solutions preferably are isotonic and may contain ingredients, such as anti-oxidants, buffers, bacteriostats and solutes that render the composition isotonic with the blood of the intended recipient. Aqueous and non-aqueous sterile suspensions also may include suspending agents and thickening agents. The compositions may be presented in unit-dose or multi-dose sealed containers, for example, ampoules and vials, and may be stored as a freeze-dried (lyophilized) composition, requiring only the addition of a sterile liquid carrier, such as water, for injections, immediately prior to use. Preferred unit dosage compositions are those containing a daily dose or unit, daily sub-dose, or an appropriate fraction thereof, of an active agent.

Compounds according to the disclosure, and compositions thereof, also may be used for veterinary applications. Examples of veterinary compositions include those adapted for: (a) oral administration, external application, for example drenches (e.g., aqueous or non-aqueous solutions or suspensions); tablets or boluses; powders, granules or pellets for admixture with feed stuffs; pastes for application to the tongue; (b) parenteral administration, such as subcutaneous, intramuscular or intravenous injection, e.g. as a sterile solution or suspension; (c) topical application, e.g. as a cream, ointment or spray applied to the skin; or (d) intravaginally, e.g. as a pessary, cream or foam.

Disclosed compositions of the present disclosure typically include an amount of a disclosed compound, or compounds, ranging from greater than 0% to at least about 99%, such as from about 1% to about 90%, 5% to 80%, 10% to 70%, 20% to 60%, 30% to 50%, or other amount deemed beneficial based on empirical administration results.

IV. Synthesis

Working embodiments of a method for making disclosed compounds is illustrated by Schemes 1-4. Additional details concerning reactions illustrated by Schemes 1-4 are provided in the working examples.

Scheme 1

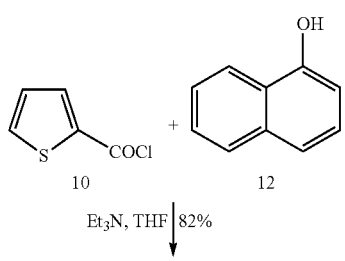

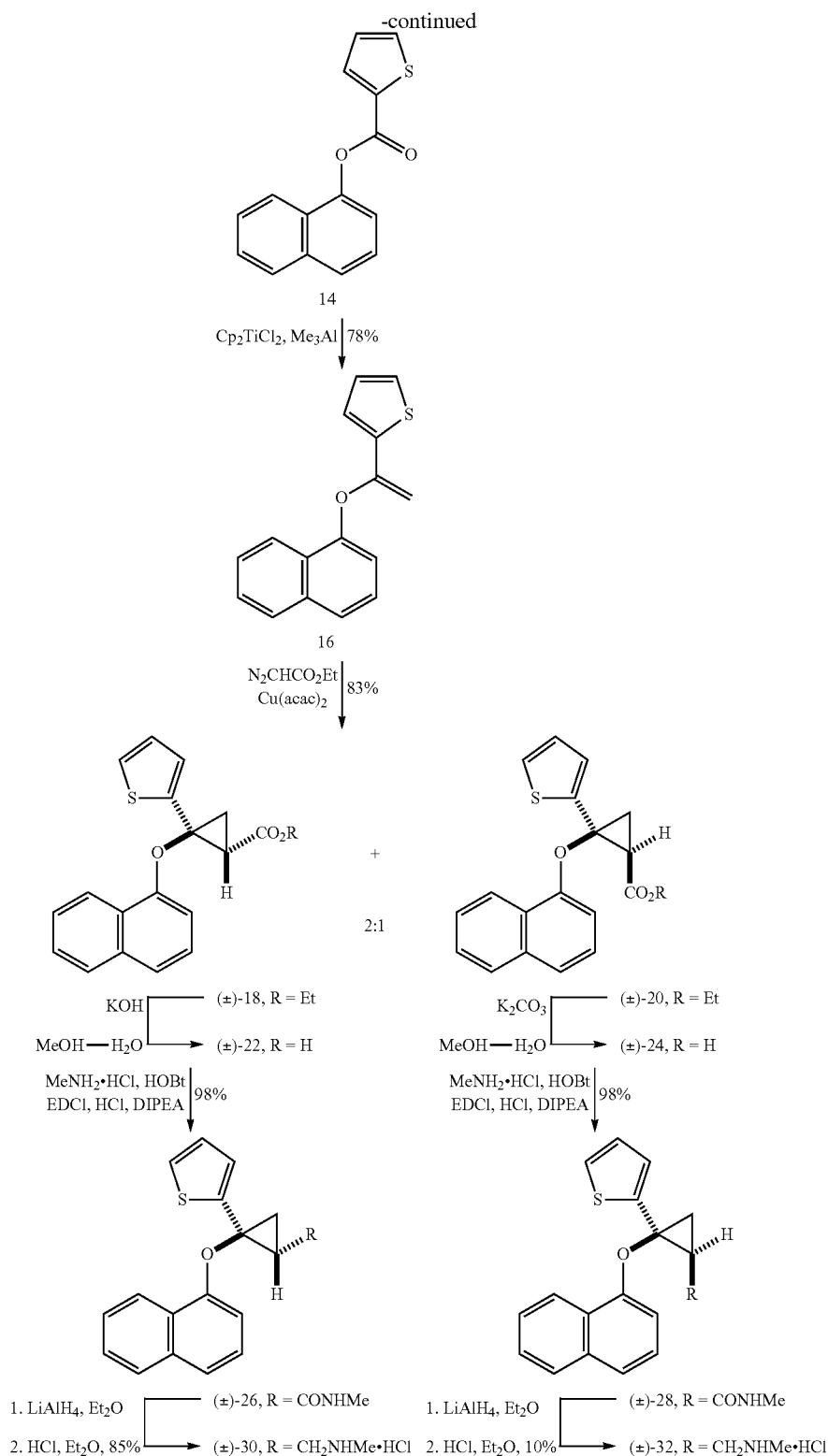

With reference to Scheme 1, the first illustrated step is the formation of compound 14 by reacting compound 10, the acid chloride of 2-thiophene carboxylic acid (2-thiophene carboxylic acid is commercially available from Aldrich), with 1-napthol 12 (1-napthol also is commercially available from Aldrich). See, Urano, T.; Sakuragi, H.; Tokumaru, K. "Intermediacy of Charged Species in Photodecompostion of Diaroyl Peroxides Sensitized with Aromatic Hydrocarbons in Polar Solvents" Chem. Lett. 1985, 6, 735, which is incorporated herein by reference. Compound 10 can be formed from the commercially available acid in the presence of an acid-chloride forming reagent, such as phosgene ($COCl_2$), in situ.

A person of ordinary skill in the art will appreciate that other chlorinating agents could be used, such as oxalyl chloride, thionyl chloride, etc. The acid chloride also may be commercially available, or optionally could be formed first, potentially isolated, and then used in the second step for coupling to a napthol derivative.

Although Scheme 1 illustrates using 2-thiophene carboxylic acid 10 and coupling that with 1-napthol 12 to form ester 14, positional isomers of these compounds also could be used to form derivatives of the illustrated biologically active compounds. For example, 1- and 2-napthol, and 2- and 3-thiophene carboxylic acid are also available from Aldrich. By coupling these commercially available compounds, different derivatives can be formed according to the general synthetic protocol illustrated in Scheme 1.

The second step illustrated in Scheme 1 is the Tebbe reaction, which is a carbonyl methylenation reaction. See, Tebbe, F. N.; Parshall, G. W.; Reddy, G. S. "Olefin Homologation with Titanium Methylene Compounds" *J. Am. Chem. Soc.* 1978, 100, 3611. This conversion also might be done using a Wittig reagent. The Tebbe reaction produces the methylenation product 16 from ester 14.

A cyclopropanation reaction was used to form compounds 18 and 20. For the illustrated method, the cyclopropane ring was introduced by copper-catalyzed, diazocyclopropanation using ethyl diazoacetate [$N_2CHCO_2CH_2CH_3$]. See, Meyer, O. G. F.; Fröhlich, R.; Haufe, G. "Asymmetric Cyclopropanation of Vinyl Fluorides: Access to Enantiopure Monofluorinated Cyclopropane Carboxylates," *Synthesis* 2000, 10, 1479, which is incorporated herein by reference. This reaction typically produced a mixture of stereoisomers.

Compound 18 also may be formed asymmetrically to produce an enantiomerically enriched composition or a substantially enantiomerically pure composition, as discussed in more detail below. For example, the cyclopropane ring may be introduced by an asymmetric Simmons Smith reaction. The Simmons-Smith reaction involves reacting a carbenoid with an alkene to form a cyclopropane. Simmons, H. E.; Smith, R. D. *J. Am. Chem. Soc.,* 1958, 80, 5323. Smith, R. D.; Simmons, H. E. *Organic Syntheses*, Coll. Vol. 5, p. 855 (1973); Vol. 41, p. 72, 1961. The Simmons-Smith reagent is diidomethane, and a zinc-copper couple ($ICH_2ZnI$). Diethylzinc also can be used instead of the zinc-copper couple. The Simmons-Smith reaction is sensitive to steric effects, such that cyclopropanation usually occurs on the less hindered face of the olefin. Hydroxy substituents on chiral carbons can be used to direct cyclopropanation.

For certain embodiments, racemic mixtures of compounds according to the present disclosure can be used as a therapeutic composition. Alternatively, racemic mixtures can be resolved to produce enantiomerically enriched compositions or substantially enantiopure compounds. Alternatively, substantially enantiopure compounds can be produced synthetically. One potential method for resolving enantiomers involves hydrolysis of esters 18 and 20 to form corresponding acids 22 and 24, followed by formation of an optically active salt. The optically active salts are then separated, such as by crystallization.

Amides 26 and 28 are formed by reacting acids 22 and 24 with methyl amine. A person of ordinary skill in the art will appreciate that this reaction also could be accomplished using other amines, particularly lower alkyl amines, to produce derivatives of active compounds. For example, lower alkyl amines differing in chain length, and potentially regioisomers and/or stereoisomers thereof, could be used to form a homologous series of compounds corresponding to the general formulae provided in this application.

If saturated amine compounds are desired, then the carbonyl functional group of amides 26 and 28 may be reduced to a fully saturated methylene unit of compounds 30 and 32. Any suitable reducing agent can be used for this reaction, with the illustrated scheme employing lithium aluminum hydride as the reducing agent.

As with many therapeutics, the presently disclosed therapeutics are advantageously administered as salts. Any salt-forming agent can be used to form salts suitable for administration to a subject. By way of example, and without limitation, suitable salt-forming reagents include acids, particularly mineral acids, such as hydrochloric acid, but organic acids also can be used.

Favorable in vitro assays were obtained with racemate 32. This compound was thus needed in enantiomerically pure form. An initial approach to obtain an enantiomerically enriched or pure form via resolution of carboxylic acid 24 was unsuccessful. The diastereomeric salts of acid 24 obtained with several chiral bases proved inseparable by fractional crystallization.

Therefore, a de novo approach to making enantiomers of 32 was devised which introduced asymmetry using an enantioselective cyclopropanation. This method for making enantiomerically enriched, or substantially pure compounds according to the general formulae provided herein, began from 2-acetylthiophene (34) which was condensed with diethyl carbonate to give β-keto ester 36 (Scheme 2). See, Ferlin, M. G.; Chiarelotto, G.; Gasparotto, V.; Dalla Via, L.; Pezzi, V.; Barson, L.; Palù, G.; Castagliuolo, I. "Synthesis and in vitro and in vivo antitumor activity of 2-phenylpyrroloquinolin-4-ones" *J. Med Chem.* 2005, 48, 3417, which is incorporated herein by reference.

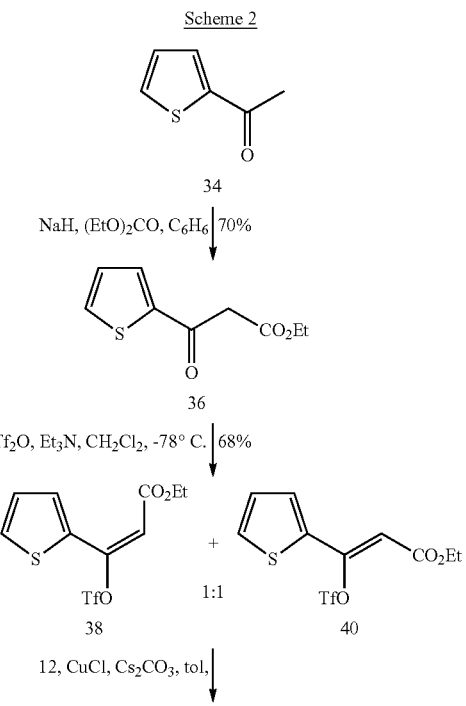

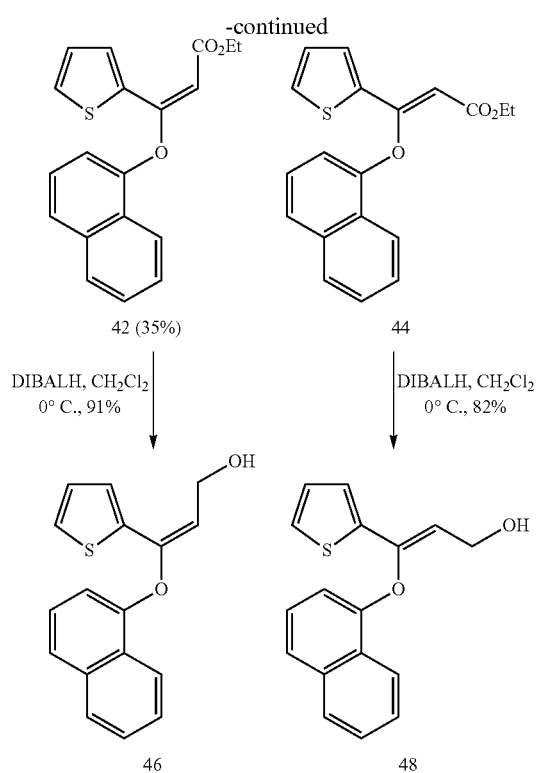

Exposure of 36 to a basic solution of triflic anhydride produced a 1:1 mixture of (E)- and (Z)-enol triflates 38 and 40, respectively. See, Loreto, M. A.; Pompei, F.; Tardella, P. A.; Tofani, D. "β,γ-Unsaturated α-Amino Ester Derivatives by Amination of γ-Silylated α,β-Unsaturated Esters," *Tetrahedron* 1997, 53, 15853, which is incorporate herein by reference. Enol triflates 38 and 40 were reacted with 1-naphthol (12) in the presence of copper(I) chloride and cesium carbonate to afford enol ethers 42 and 44. See, Liu, Z.; Larock, R. C. "Facile N-Arylation of Amines and Sulfonamides and O-Arylation of Phenols and Arenecarboxylic Acids," *J. Org. Chem.* 2006, 71, 3198, which is incorporated herein by reference. Reduction of this mixture of esters gave (E)- and (Z)-allylic alcohols 46 and 48, respectively, which were separated by careful column chromatography.

Separation of allylic alcohols 46 and 48 allowed each to be taken forward as substrates for Charette asymmetric cyclopropanation. This reaction was carried out with diiodomethane and diethylzinc in the presence of a catalytic quantity of the (S,S)-tartrate derived boronate 50 and produced (E)- and (Z)-cyclopropylmethanols (−)-52 and (+)-54, respectively (Scheme 3).

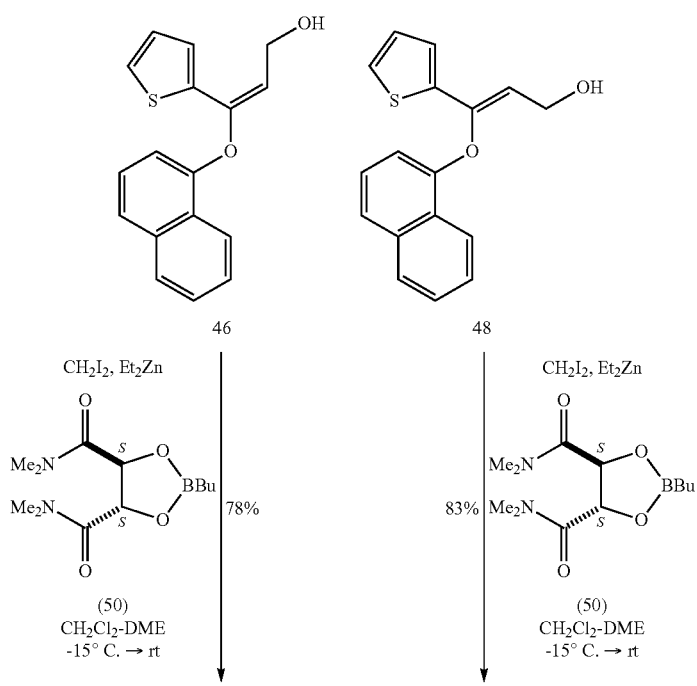

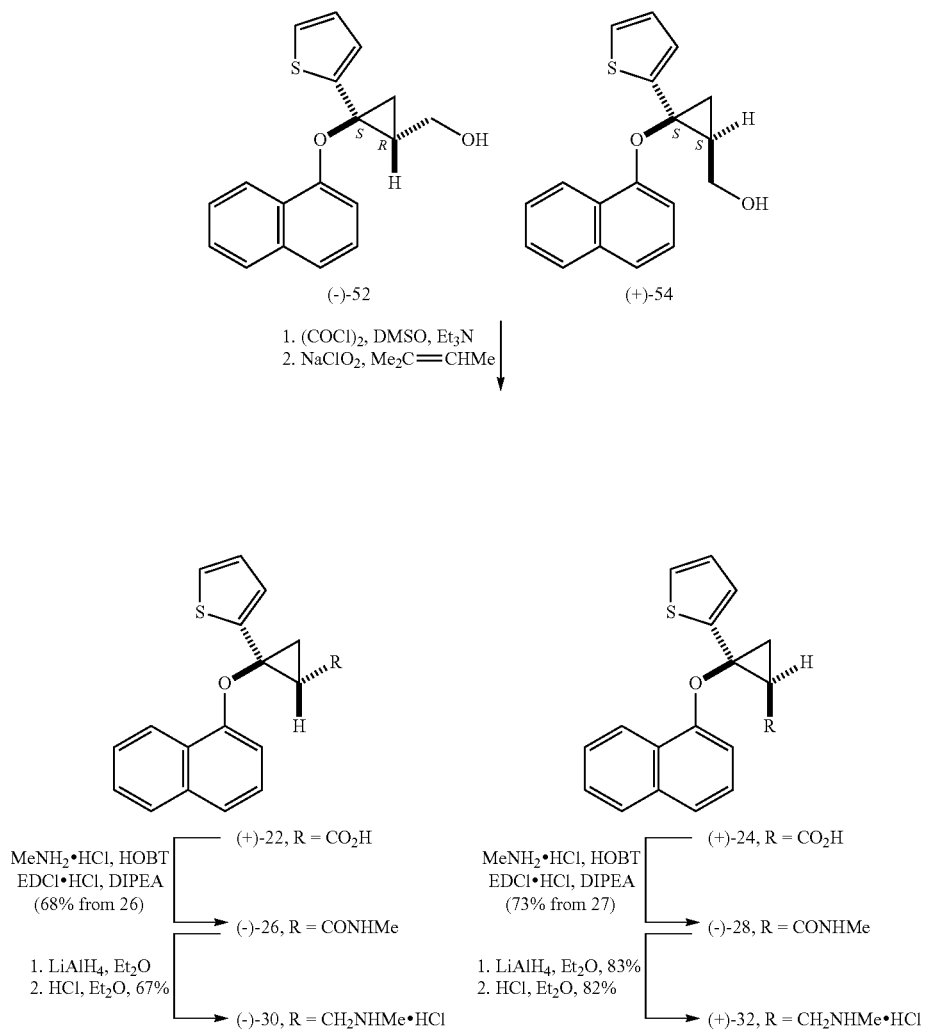

The assumption based on Charette's model (See, Charette, A. B.; Juteau, H. "Design of Amphoteric Bifunctional Ligands: Application to the Enantioselective Simmons-Smith Cyclopropanation of Allylic Alcohols," *J. Am. Chem. Soc.* 1994, 116, 2651, (incorporated herein by reference) that (−)-52 and (+)-54 possessed (R,S) and (S,S) configuration, respectively, was verified by oxidation of the mixture to carboxylic acids (+)-22 and (+)-24. The two-step oxidation sequence first took alcohols (−)-52 and (+)-54 to their corresponding aldehydes under Swern conditions [Mancuso, A. J.; Swern, D. "Activated Dimethyl Sulfoxide: Useful Reagents for Synthesis" *Synthesis* 1981, 165, incorporated herein by reference] and then to the crystalline carboxylic acids (+)-22 and (+)-24 by Pinnick oxidation [see, Miura, T.; Murakai, Y.; Imai, N. "Synthesis of (R)-(+)-cibenzoline and analogues via catalytic enantioselective cyclopropation using (S)-phenylalanine-derived disulfonamide," *Tetrahedron: Asymm*, 2006, 17, 3067, incorporated herein by reference]. These acids were shown to be spectroscopically identical to their racemic counterparts. X-ray crystallographic analysis of (+)-24 confirmed its absolute configuration as (S,S). Condensation of enantiomerically pure acids (+)-22 and (+)-24 with methylamine in the presence of EDCI and HOBT afforded amides (−)-26 and (−)-28, which were reduced to the corresponding amines and acidified with HCl to furnish hydrochlorides (−)-30 and (+)-32. An X-ray crystal structure of (−)-30 confirmed its stereostructure including its absolute configurations as (1R,2S).

A parallel cyclopropanation sequence to that shown in Scheme 3 with 56, the enantiomer of 50, was used to synthesize enantiomeric hydrochlorides (+)-30 and (−)-32 for evaluation of their pharmacological properties. Thus, asymmetric cyclopropanation of 46 and 48 with boronate 56 prepared from (R,R)-tartrate led to (E)- and (Z)-cyclopropanes (+)-58 and (−)-60, respectively (Scheme 4).

Scheme 4

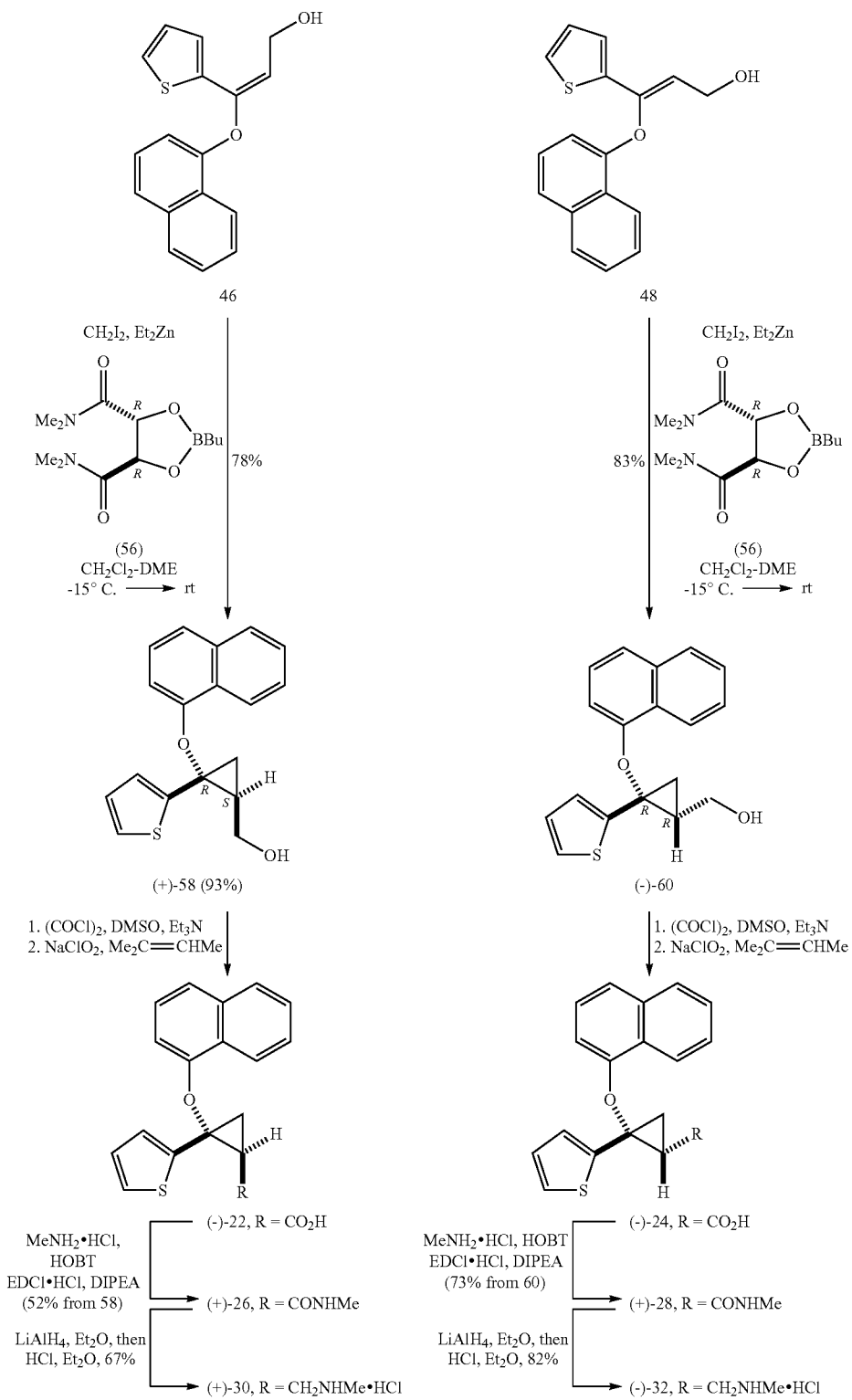

Alcohols 58 and 60 were oxidized to carboxylic acids (−)-22 and (−)-24, respectively, which were converted separately to amides (+)-26 and (+)-28. The amides were reduced to the corresponding amines and acidified to give hydrochlorides (+)-30 and (−)-32, respectively. X-ray crystallographic structure determination of (+)-30 and (−)-32 confirmed that these substances possessed the absolute configuration shown.

V. Biological Results for Working Embodiments

Biological results for two representative compounds initially tested as racemic mixtures are provided by FIGS. 1-6. These data are presented with respect to the following compounds, blind tested as racemic mixtures by a third party independent laboratory, using the blinding test codes indicated.

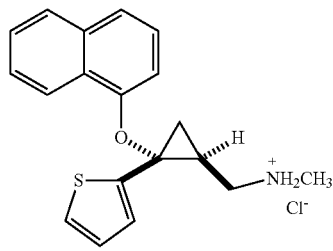

Test Code No. DWJW0002

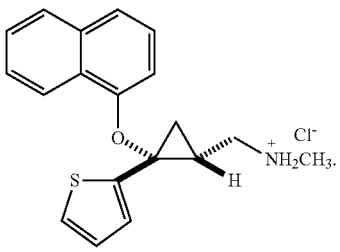

Test Code No. DWJW0003

Information provided by FIGS. 1-6 is summarized below in Table 1. $IC_{50}$, or the half maximal inhibitory concentration, represents the concentration of an inhibitor that is required for 50% inhibition of a target in vitro.

transporter and has comparable activity to the reference standard imipramine. As an inhibitor of norepinephrine transporter, DWJW0003 is about 9 times more potent than DWJW0002. The reference standard desipramine is about 50 times more potent than DWJW0002 and about 5 times more potent than DWJW0003. As an inhibitor of dopamine transporter, DWJW0003 is about 2 times more potent than DWJW0002. The reference standard GBR12909 is 16 times more potent than DWJW0002, and 8 times more potent that DWJW0003. These data suggest that DWJW0002 is a relatively selective inhibitor of serotonin transporter and that DWJW0003 is a relatively equal, comparably potent (or relatively balanced) inhibitor (with comparable potencies) of all 3 transporters tested.

Table 2 below provides additional biological results for representative compounds disclosed herein. DWJW0004, the structure of which is provided below, is the S-enantiomer (known as S, hereafter) of the RS-racemate, DWJW0003 (known as RS, hereafter).

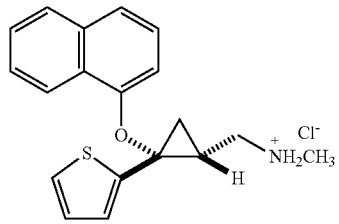

Test Code No. DWJW0004

TABLE 1

| | DWJW0002 | | | DWJW0003 | | | Reference | | |
|---|---|---|---|---|---|---|---|---|---|
| Target | $IC_{50}$ | Ki* | Slope | $IC_{50}$ | Ki | Slope | $IC_{50}$ | Ki | Slope |
| Serotonin (5-HT) transporter | 9.16 | 7.47 ± 0.45 (3) | −0.92 | 27.0 | 2.01 ± 0.16 (2) | −1.19 | 14.2 | 7.57 ± 0.72 (10) (imipramine) | −1.06 |
| Norepinephrine (NE) trans-porter | >300 | 75.7 ± 17.2 (2) | | 44.3 | 4.16 ± 1.27 (2) | −0.84 | 7.94 | 5.11 ± 0.70 (11) (desipramine) | −0.69 |
| Dopamine (DA) transporter | 147 | 586 ± 120 (2) | −1.11 | 71.7 | 283 ± 5.3 (2) | −1 | 8.93 | 5.07 ± 0.56 (11) (GBR12909) | −1.25 |

*Ki is reported as nanomolar concentrations, ± Standard Error in the Measurement (S.E.M.), with the number in parentheses indicating number of determinations.

With reference to Table 1, DWJW0002 is about 3 times more potent than DWJW0003 as an inhibitor of serotonin

TABLE 2

Affinity of DWJW0004 determined by radioligand binding to transporters serotonin (5-hydroxytryptamine, 5-HT), norepinephrine (NE) and dopamine (DA)

| | Neurotransmitter Transporter | | |
|---|---|---|---|
| Inhibitor | 5-Hydroxy Tryptamine (5-HT) | Norepinephrine (NE) | Dopamine (DA) |
| DWJW0004 | 2.10 ± 0.60 (3) | 1.19 ± 0.08 (3) | 223 ± 20.5 (2) |
| DWJW0003 | 2.01 ± 0.16 (2) | 4.16 ± 1.27 (2) | 283 ± 5.3 (2) |

TABLE 2-continued

Affinity of DWJW0004 determined by radioligand binding to transporters serotonin (5-hydroxytryptamine, 5-HT), norepinephrine (NE) and dopamine (DA)

| Inhibitor | Neurotransmitter Transporter | | |
|---|---|---|---|
| | 5-Hydroxy Tryptamine (5-HT) | Norepinephrine (NE) | Dopamine (DA) |
| Imipramine | 7.57 ± 0.72 (10) | — | — |
| Desipramine | — | 5.11 ± 0.70 (11) | — |
| GBR12909 | — | — | 5.07 ± 0.56 (11) |
| Duloxetine (Cymbalta ®) | 0.8 ± 0.04 | 7.5 ± 0.3 | 240 ± 23 |
| Venlafaxine (Effexor ®) | 82 ± 3 | 2480 ± 43 | 7647 ± 793 |
| Fluoxetine (Prozac ®) | 0.81 ± 0.02 | 240 ± 10 | 3600 ± 100 |
| DOV21947 | 190 ± 28 | 380 ± 43 | 190 ± 40 |
| JNJ-7925476 | 0.9 ± 0.1 | 16.6 ± 7.0 | 5.2 ± 1.0 |

*$K_i$ is reported as nanomolar concentrations, ±Standard Error in the Measurement (S.E.M.), with the number in parentheses indicating number of determinations. Assays were conducted in NovaScreen, NJ.
**All other data derived from literature including duloxetine, venlafaxine and fluoxetine from Wong & Bymaster, *Progress in Drug Research*, 58: 170-222 (2002); DOV21947 from Chen & Skolnick, *Investig. Drugs*, 16:1365-1377 (2007); and JNJ-7925476 from Aluisio, et. al, *Eur. J. Pharmacol.*, 4:008 (2008).

The mean $K_i$ values obtained from three separate determinations show that S inhibits NE, 5-HT and DA transporters with relative potencies of 1, ½ and ⅓₀₀, respectively (Table 2). In comparison with RS, the potency of S to inhibit transporter of NE increases 28 fold, and the transporter of 5-HT 10 fold, but decreases that of DA transporter by 6.3 fold. Thus, S is a dual inhibitor of NE and 5-HT transporters. The therapeutic value of S can be examined further by determining its ability to elevate extracellular levels of NE, DA and 5-HT in brain regions, particularly the prefrontal cortex, of conscious, freely moving rats using microdialysis techniques.

The $K_i$ values of two known dual inhibitors, duloxetine (Cymbalta®) and venlafaxine (Effexor®), are included in Table 2 for comparison. S is three times more potent than duloxetine as an inhibitor of NE transporter and about ⅓ as inhibitory of 5-HT transporter. Despite venlafaxine being known as a dual inhibitor of 5-HT and NE transporters, it is not as effective as either duloxetine or S. Moreover, S is more balanced than duloxetine or venlafaxine as an inhibitor of NE and 5-HT transporters. All three compounds are weak inhibitors of DA transporter. Both duloxetine and venlafaxine are indicated for treating depression, while the U.S. Food & Drug Administration also has approved duloxetine for treating diabetes, peripheral neuropathic pain, general anxiety, and fibromyalgia. Approval for duloxetine for treating chronic pain also is pending.

RS exhibits moderate affinity for the DA transporter, while its S-enantiomer has only 0.16 the affinity. The inhibiting potency for the DA transporter should be enriched in the R-enantiomer. Since the inhibiting potencies for the NE and 5-HT transporters are enriched in the S-enantiomer, the respective potencies in the R-enantiomer would be proportionately reduced. Thus, the R-enantiomer potentially would be an inhibitor that inhibits the transporters of NE, 5-HT and DA with moderate potencies or it may be called a "triple uptake inhibitor" with potencies likely to be superior to DOV21947 (Chen & Skolnick, 2007), but either comparable or less potent than JNJ-7925476 (Aluisio, et. al., 2008). A triple uptake inhibitor potentially may be used for treating resistant depression, substance abuse and obesity or weight gain.

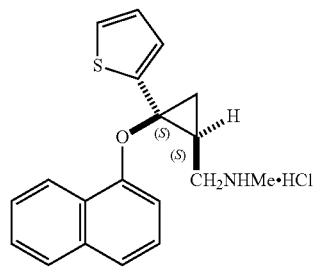

Test Code No. DWJW0004

TABLE 3

Inhibition of Transporters of Norepinephrine (NE), Serotonin (5-HT) and Dopamine (DA) by DWJW0004 and other known inhibitors

| | Transporter | | | |
|---|---|---|---|---|
| Inhibitor | NE | 5-HT $K_i$, nM | DA | NE/5-HT |
| DWJW0004 | 1.19 ± 0.08(3) | 2.10 ± 0.06(3) | 223 ± 20.5(2) | 0.57 |
| Duloxetine [1] | 7.5 ± 0.3 | 0.8 ± 0.01 | 240 ± 23 | 9.4 |
| Desipramine [1] | 3.8 ± 0.3 | 179 ± 10 | >10,000 | 0.21 |
| Fluoxetine [1] | 1021 ± 46 | 6.9 ± 0.6 | 4752 ± 44 | 148 |

[1] Bymaster, et. al. *Curr. Pharmc Design* 2004.

Minor changes in molecular structures of inhibitors alter selectivity toward transporters of serotonin (5-hydroxytryptamine, 5-HT) or norepinephrine (NE). For example, changing the trifluoromethyl-group at the para-phenoxy ring of fluoxetine to the ortho-methyl-substitution, as in atomoxetine, imparts a 2-order magnitude increase in selectivity to inhibit the NE transporter (Wong et al., *Life Sci.* 15: 471-479, 1974; Wong et. al., *Life Sci.* 17: 755-760, 1975). Duloxetine is a dual inhibitor of 5-HT and NE transporters with over 9-fold preference to inhibit the 5-HT transporter (Bymaster et al., *Curr. Pharm. Des.* 11:1475-1493, 2005). The aminopropyl unit of duloxetine can be replaced by an aminomethylcyclopropane moiety resulting in DWJW0004, which imparts a 6-fold enhanced potency for inhibiting the NE transporter (Table 3) (White, *J. Med. Chem.* 52: 5872-5879, 2009). Based on radioligand binding assays, DWJW0004 inhibited the transporters of NE and 5-HT with comparable $K_i$ values, 1.2 nM and 2.1 nM, respectively (Table 3), suggesting a balanced Initial assays to determine the efficacy of cyclopropanes 30 and 32 as inhibitors of serotonin, norepinephrine and dopamine transporters were conducted on the racemates. The data presented below in Table 4 suggested that (±)-30 is a relatively selective inhibitor of serotonin transporter whereas (±)-32 is a more balanced inhibitor of both serotonin and norepinephrine transporters. One enantiomer in particular, (+)-32, is a highly effective dual inhibitor of serotonin and norepinephrine transporters. With $IC_{50}$ and Ki values in the 1-2 nM range, (+)-32 compares favorably with duloxetine (Cymbalta®) [Bymaster, F. P.; Beedle, E. E.; Findlay; Gallagher, P. T.; Krushinski, J. H.; Mitchell, S.; Robertson, D. W.; Thompson, D. C.; Wallace, L.; Wong, D. T. "Duloxetine (Cymbalta®), a dual inhibitor of serotonin and norepinephrine reuptake," *Bioorg. Med. Chem. Lett.* 2003, 13, 4477 as a dual inhibitor of serotonin and norepinephrine transporters.

TABLE 4

Inhibition of Monamine Transporters of Serotonin (5-HT), Norepinephrine (NE) and Dopamine (DA) by Racemic 30 and 32, their Enantiomers and Reference Compounds.[a]

| Compound | Serotonin (5-HT) | | Norepinephrine (NE) | | Dopamine (DA) | |
|---|---|---|---|---|---|---|
| | $IC_{50}$(nM) | $K_i$(nM) | $IC_{50}$(nM) | $K_i$(nM) | $IC_{50}$(nM) | $K_i$(nM) |
| (±)-30 | 10.9 (13.6)[b] | 8.6 (10.7) | 65.4 (7.5) | 51.3 (5.9) | 507 (3.5) | 416 (2.8) |
| (+)-30 | 42.9 (7.1) | 33.2 (5.5) | 200 (10.6) | 153 (8.2) | 1120 (4.7) | 913 (3.8) |
| (−)-30 | 22.4 (13.6) | 17.6 (10.7) | 430 (10.6) | 330 (8.2) | 963 (3.5) | 790 (2.8) |
| (±)-32 | 2.3 (7.5) | 1.8 (5.8) | 3.1 (5.2) | 2.4 (4.0) | 338 (10.2) | 275 (8.3) |
| (+)-32 | 1.5 (12.7) | 1.2 (10.3) | 1.6 (7.2) | 1.2 (5.2) | 309 (3.5) | 252 (2.8) |
| (−)-32 | 37.7 (7.8) | 29.3 (6.1) | 37.4 (5.3) | 28.2 (4.0) | 2070 (7.2) | 1620 (5.6) |

Figure 7:
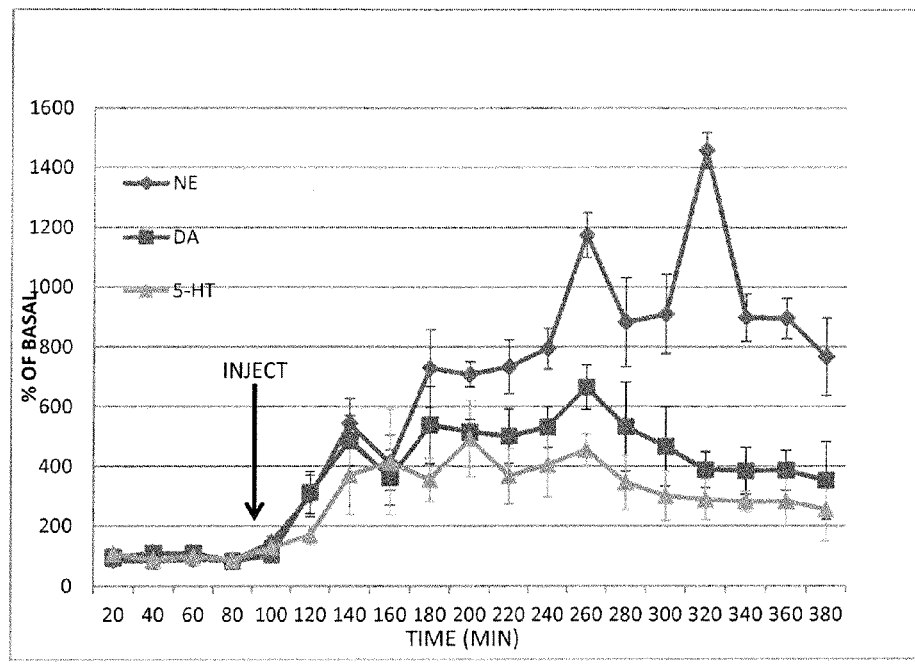
FIG. 7 is a percent of basal versus time (minutes) graph illustrating the in vivo effect of 10 mg/kg, i.p of DWJW0004 on norepinephrine transporter (NE), dopamine transporter (DA), and serotonin transporter (5-HT) levels in rat prefrontal cortex.
Figure 8:
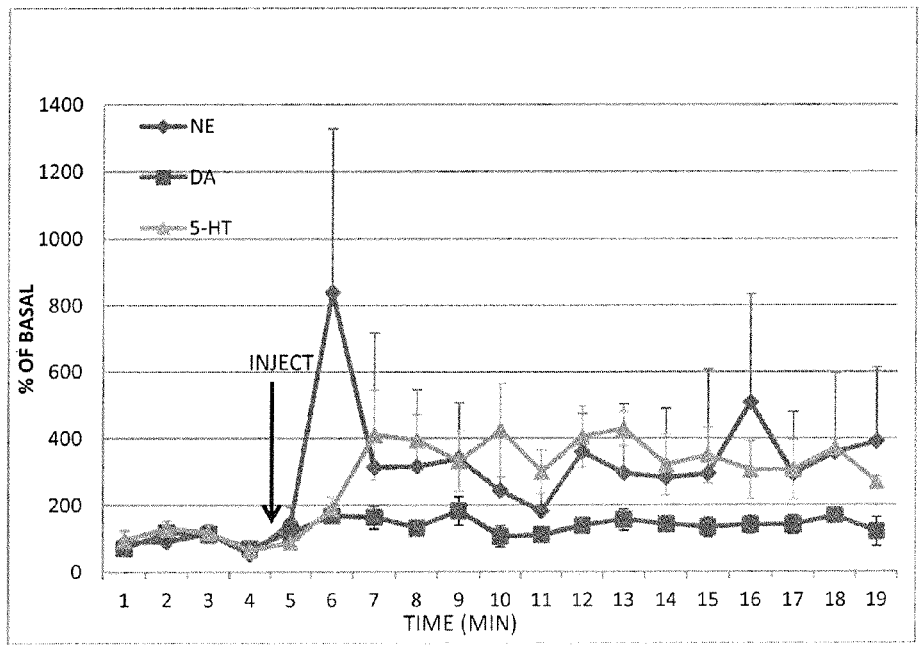
FIG. 8 is a percent of basal versus time (minutes) graph illustrating the in vivo effect of 10 mg/kg, i.p. of DWJW0004 on norepinephrine transporter (NE), dopamine transporter (DA), and serotonin transporter (5-HT) levels in rat nucleus accubmens.
Figure 9:
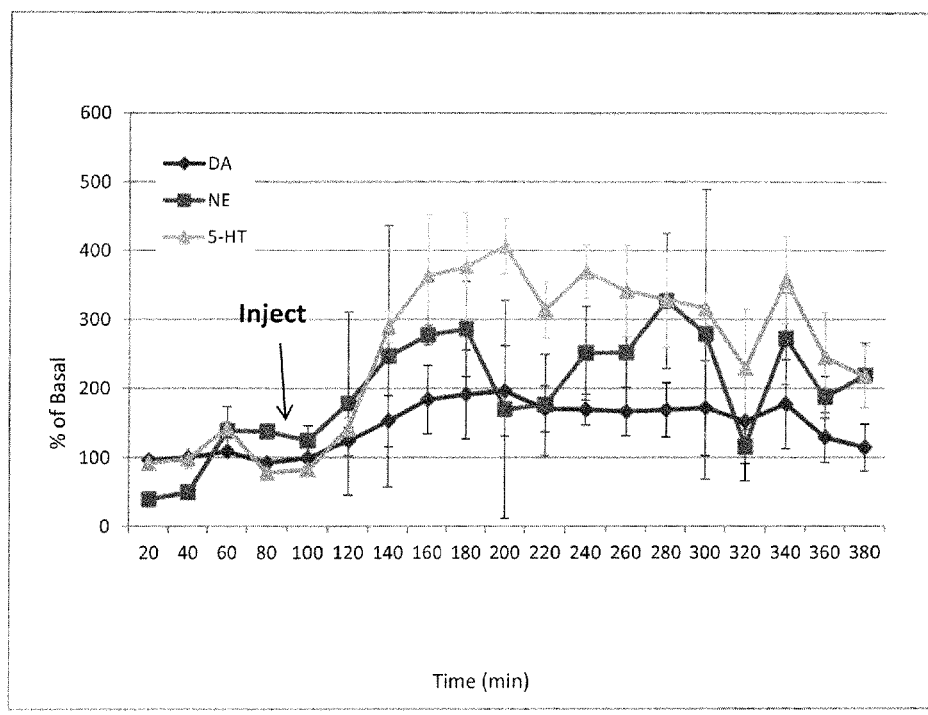
FIG. 9 is a percent of basal versus time (minutes) graph illustrating the in vivo effect of 10 mg/kg, i.p. of DWJW0004 on norepinephrine transporter (NE), dopamine transporter (DA), and serotonin transporter (5-HT) levels in rat striatum.

[a]All tests were conducted by NovaScreen, Caliper Lifesciences, Hopkinton, MA.
[b]Values in parentheses are those for reference compounds: imipramine for serotonin transporter, desipramine for norepinephrine transporter, and GBR12909 for dopamine transporter.

and potent inhibitor. In vivo, DWJW0004 administration to freely moving male rats at 10 mg/kg i.p. significantly elevated extracellular levels of NE, dopamine (DA), and 5-HT in the prefrontal cortex (FIG. 7) by 1000, 600, and 450% of baseline, respectively (p<0.05; RMANOVA). In the nucleus accumbens (FIG. 8), NE and 5-HT were both significantly elevated above 400% of baseline levels (p<0.05; RMANOVA), with no change in DA levels (p>0.05), whereas the increases of monoamines occurred in striatum (FIG. 9) did not reach statistical significance. The magnitude of increased extracellular levels of monoamines was comparable, if not greater than that which resulted from administration of duloxetine (Engleman et al., *Neuropsychopharm.* 12: 287-95, 1995). These findings are consistent with the following conclusions: (1) Introduction of a cyclo-propyl moiety to the propylamino side chain of duloxetine as in DWJW0004 brings a greater potency inhibiting human NE transporter compared to duloxetine; (2) DWJW0004 is a potent and balanced inhibitor of NE and 5-HT transporters in brain; (3) Upon administration, DWJW0004 elevates extracellular levels of NE, 5-HT and DA in prefrontal cortex (p<0.05) and NE and 5-HT in nucleus accumbens (p<0.05) and striatum in brain of conscious freely moving rats; (4) The embodiments disclosed herein, particularly DWJW0004, are proposed to have clinical indications similar to those of duloxetine in treating depression and related CNS disorders. Given these conclusions, DWJW0004 (and, likely, other embodiments) is a balanced and potent inhibitor of the NE and 5-HT transporter in vivo as observed in vitro. Compared with duloxetine, we believe that DWJW0004 would have a comparable profile of clinical indications (Berk et al., *Int. Clin. Psychopharmacol.* 12: 137-140, 1997).

VI. Chemical Structure

Biological Effects of Known Inhibitors for Comparison

Table 5 below provides Ki constants (nM) of other known inhibitors for comparison to the biological activity of compounds of the present disclosure. Also, these known compounds, as well as other known and future developed compounds, may be used in combination with a compound or compounds, or compositions thereof, of the present disclosure.

TABLE 5

| Inhibitor | Serotonin | Norepinephrine | Dopamine |
|---|---|---|---|
| Duloxetine (Cymbalta ®) | 0.8 | 7.5 | 240 |
| Venlafaxine (Effexor ®) | 82 | 2480 | 7647 |
| Milnacipran | 123 | 200 | >10,000 |
| Fluoxetine (Prozac ®) | 0.8 | 240 | 3600 |
| Sertraline (Zoloft ®) | 0.29 | 420 | 25 |
| Atomoxetine (Strattera ®) | 77 | 5 | 1451 |
| Imipramine | 1.4 | 37 | 8500 |
| Desipramine | 17.6 | 0.83 | 3190 |

Duloxetine is a serotonin-norepinephrine reuptake inhibitor (SNRI). It is a less potent inhibitor of dopamine uptake.

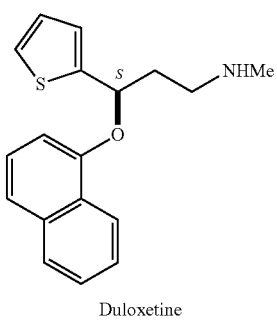

Duloxetine

Venlafaxine is a prescription antidepressant used to treat clinical depression, anxiety disorders, and (controversially) bipolar disorder. It also is a serotonin-norepinephrine reuptake inhibitor.

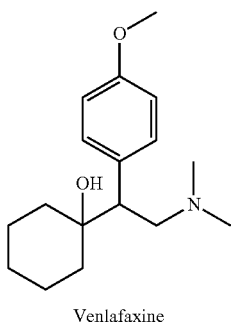 [SMILES: COc1ccc(C(CN(C)C)C2(O)CCCCC2)cc1]

Venlafaxine

Milnacipran is a serotonin and norepinephrine reuptake inhibitor, which is less potent in comparison with duloxetine and venlafaxine as an inhibitor of serotonin transporter and intermediate among the three inhibitors of norepinephrine transporter. Currently, milnacipran is not available as an antidepressant in the United States.

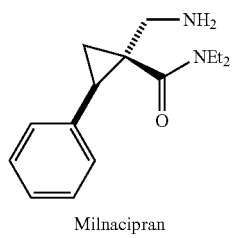

Milnacipran

Fluoxetine is an antidepressant of the selective serotonin reuptake inhibitor (SSRI) class approved in the United States in 1987.

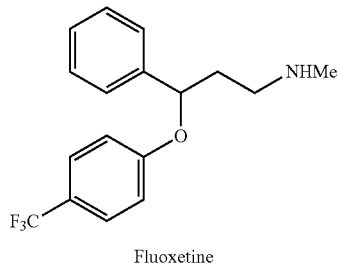 [SMILES: CNCCC(Oc1ccc(C(F)(F)F)cc1)c1ccccc1]

Fluoxetine

Sertraline hydrochloride is an orally administered antidepressant of the selective serotonin reuptake inhibitor class first approved by the FDA for use in the USA in 1991.

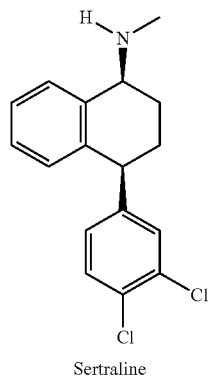 [SMILES: CN[C@H]1CC[C@@H](c2ccc(Cl)c(Cl)c2)c2ccccc21]

Sertraline

Atomoxetine hydrochloride is a non-stimulant drug approved for treating attention-deficit disorder in the United States in 2002, and is a norepinephrine reuptake inhibitor.

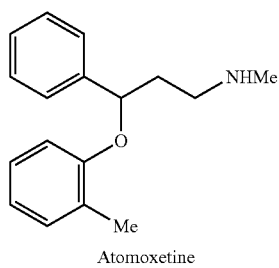 [SMILES: CNCCC(Oc1ccccc1C)c1ccccc1]

Atomoxetine

Imipramine is a tertiary amine that inhibits the reuptake of serotonin more so than most secondary amine tricyclics, as it blocks the reuptake of the neurotransmitters serotonin and noradrenaline almost equally. Imipramine also has activity at sigma opiate receptors, as well as substantial activity at D1 and D2 dopamine receptors.

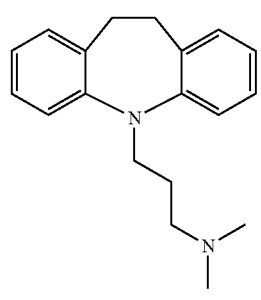

Imipramine

Desipramine is an active metabolite of imipramine. Desipramine activates, through norepinephrine reuptake inhibition, descending pathways in the spinal cord that block pain signals from the brain.

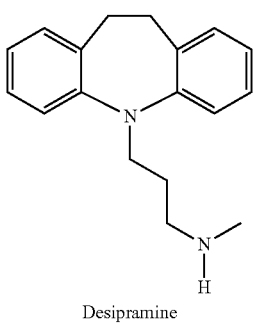 [SMILES: CNCCCN1c2ccccc2CCc2ccccc21]

Desipramine

GBR12909 (GBR) is a selective inhibitor of dopamine (DA) uptake that produces a persistent and noncompetitive blockade of DA transporters. GBR12909 substantially reduces cocaine-induced increases in extracellular DA in rats.

GBR12909

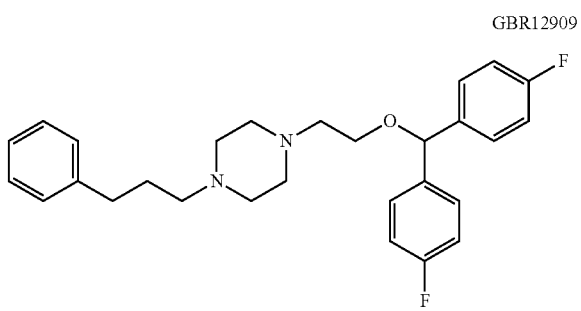 [SMILES: Fc1ccc(C(OCCN2CCN(CCCc3ccccc3)CC2)c2ccc(F)cc2)cc1]

Compounds, and compositions thereof, of the present disclosure can be used generally as neurotransmitter modulators, such as reuptake inhibitors, of neurotransmitters, including by way of example and without limitation, serotonin, norepinephrine and/or dopamine. Compounds, and compositions thereof, of the present disclosure also may be useful for treating one or more of a variety of specific maladies, including by way of example and without limitation, major depressive disorder, (MDD), generalized anxiety disorder, (GAD), obsessive compulsive disorder, panic disorder, social phobia, posttraumatic stress disorder, Huntington's chorea, Parkinson's disease, spasticity, epilepsy, schizophrenia, tardive dyskinesia, pain related to diabetic peripheral neuropathy, stress, urinary incontinence, fibromyalgia, bipolar disorder, attention deficit and disruptive behavior with or without hyperactivity disorder, enuresis, migraines, post concussive syndrome, chronic pain and/or Kleine-Levin syndrome, obesity, anorexia nervosa, bulimia, substance abuse generally, alcoholism, alcohol abuse, alcohol dependence, cocaine abuse, cocaine dependence, nicotine dependence (smoke cessation), kleptomania, trichotillomania, and premenstrual dysphoric disorder. Such compounds also may be useful for improving memory, such as with fluoxetine. See, U.S. Pat. No. 4,647,591.

VII. Administering Compounds/Compositions

Compounds of the present disclosure, and compositions containing such compounds, can be administered to provide a subject an effective amount of the active agent or agents. A person of ordinary skill in the art will appreciate how to determine an effective amount. However, solely by way of example, it currently is believed that such compounds can be administered to provide from at least as low as about 20 milligrams up to at least about 300 milligrams of active agent, and to provide a dosage effective for treating a particular malady, such as a dose of at least as low as about 40 mg/day (such as by administering 20 mg twice daily) up to a dose of about 300 mg/day; typically from about 40 mg/day to about 250 mg/day; more typically from about 40 mg/day to about 200 mg/day; even more typically from about 40 mg/day to about 150 mg/day; even more typically from about 40 mg/day to about 100 mg/day, either as a single dose or as multiple doses.

VIII. Working Examples

The following examples are provided to illustrate certain features of disclosed working embodiments. A person of ordinary skill in the art will appreciate that the scope of the invention is not limited to those features exemplified by these working examples.

A. General Methods

All reactions requiring anhydrous conditions were conducted in flame-dried glass apparatus under an argon atmosphere. Tetrahydrofuran, ether, dichloromethane, ethyl acetate and hexanes were dried by passage through an activated alumina column under argon. Dimethyl sulfoxide was distilled from calcium hydride at 15 mm Hg and stored over activated 4 Å molecular sieves. Methanol and 1,2-dimethoxyethane were freshly distilled from calcium hydride. Preparative chromatographic separations were performed on silica gel (35-75 μm). Reaction progress was followed by thin layer chromatography using silica plates with a fluorescent indicator (254 nm), which were visualized with a UV lamp or phosphomolybdic acid. All commercially available reagents were purchased and used as received unless stated otherwise. Optical rotations were measured with a polarimeter using a 1 mL capacity cell with 1 dm path length. Infrared spectra were recorded using a thin film supported between KBr discs or dispersed in a KBr pellet. $^1$H and $^{13}$C NMR spectra were recorded in Fourier transform mode at the field strength specified on either a 300 or 400 MHz spectrometer. Spectra were obtained on solutions in 5 mm diameter tubes, and chemical shifts in ppm are quoted relative to the residual signals of CHCl$_3$ ($\delta_H$ 7.26 ppm, or $\delta_C$ 77.0 ppm). Multiplicities in the $^1$H NMR spectra are described as: s=singlet, d=doublet, t=triplet, q=quartet, m=multiplet, br=broad; coupling constants are reported in Hz. Low (MS) and high (HRMS) resolution mass spectra are reported with ion mass/charge (m/z) ratios in atomic mass units.

Example 1

This example concerns synthesis protocols for 1-Naphthyl Thiophen-2-carboxylate.

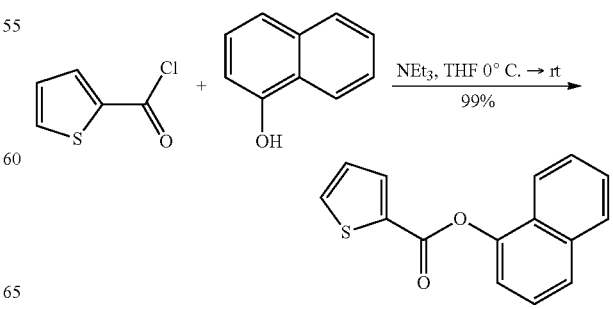

Thiophencarbonyl chloride (5.00 g, 34.1 mmol) was dissolved in THF (85 mL) and the solution was cooled in an ice-bath. A solution of 1-naphthol (9.80 g, 68.2 mmol) in THF (68 mL) was added slowly by syringe pump. After all of the solution had been added, the mixture was stirred at room temperature for 10 minutes and then $NEt_3$ (68.2 mmol, 9.5 mL) was added by syringe. A white solid precipitated immediately and the mixture was stirred for 4 hours, after which the reaction had reached completion. The reaction was quenched with HCl (5M) and the mixture was extracted with $CH_2Cl_2$. The organic phase was separated and dried with sodium sulfate. After removal of the solvent, flash chromatography of the residue on silica gel (100% hexanes) gave the product as a colorless solid (9.30 grams, 99%). mp 70-75° C.; IR (KBr) 3062, 1729, 1598, 1522, 1507 $cm^{-1}$; $^1H$ NMR (300 MHz, $CDCl_3$) δ 7.43 (dd, J=8, 1 Hz, 1H), 7.50-7.59 (m, 1H), 7.75 (dd, J=5, 1 Hz, 1H), 7.81 (d, J=8 Hz, 1H), 7.97-8.05 (M, 1H), 8.12 (dd, J=4, 1 Hz, 1H); $^{13}C$ NMR (100 MHz, $CDCl_3$) δ 118.2, 121.3, 125.4, 126.2, 126.5, 126.9, 128.0, 128.2, 132.7, 133.7, 134.7, 134.9, 146.5, 160.7; HRMS (EI) m/z 254.0395 (calcd for C15H10O2S 254.0402).

Example 2

This example concerns synthesis protocols for 2-(1-(Naphthalen-1-yloxy)vinyl)thiophene.

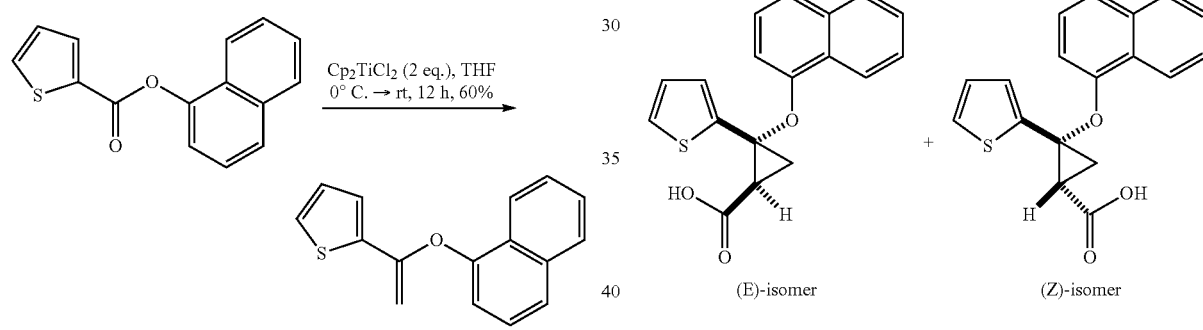

Di(cyclopentadienyl)titanium(IV) dichloride (14.0 grams, 56.4 mmol) was placed in a flask and solution of a trimethylaluminum in hexanes (112.8 mmol, 56.4 mL of 2M solution in hexanes) was syringed into the solution. The deep red slurry containing Tebbe reagent was stirred at room temperature for 3 days. 1-Naphthyl 2-thiophencarboxylate (9.30 grams, 36.6 mmol) was dissolved in THF (30 mL) and the solution was syringed into the flask containing the Tebbe reagent. The slurry was stirred overnight at room temperature and diluted with ether (30 mL). A solution of NaOH (1M) was added slowly until gas evolution ceased. To the resulting orange slurry was added anhydrous sodium sulfate to remove excess water and the mixture was filtered through a silica pad on a large coarse frit using suction. After removal of the solvent, flash chromatography of the residual oil on silica gel (5% $NEt_3$ in hexanes) gave the product as a brown oil (5.50 g, 21.8 mmol, 60%). IR (KBr) 3105, 3053, 1641, 1596, 1576, 1507, 1461, 1434, 1391, 1358, 1259, 1230, 1091, 1063, 1041, 944, 801, 744, 704 $cm^{-1}$; $^1H$ NMR (300 MHz, $CDCl_3$) δ 4.25 (d, J=3 Hz, 1H), 4.95 (d, J=3 Hz, 1H), 7.02-7.07 (m, 1H), 7.18-7.24 (m, 1H), 7.25-7.33 (m, 1H), 7.40-7.45 (m, 2H), 7.49-7.54 (m, 2H), 7.63-7.86 (m, 1H), 7.84-7.90 (m, 1H), 8.12-8.19 (m, 1H); $^{13}C$ NMR (75 MHz, $CDCl_3$) δ 90.7, 115.5, 122.2, 124.4, 124.9, 125.8, 125.9, 126.3, 126.7, 127.0, 127.7, 128.1, 135.1, 139.3, 151.5, 155.5; HRMS (EI) m/z 252.0613 (calcd for $C_{16}H_{12}OS$: 252.0609).

Example 3

This example concerns synthesis protocols for (E and Z) 2-(naphthalen-1-yloxy)-2-(thiophen-2-yl)cyclopropanecarboxylic Acids.

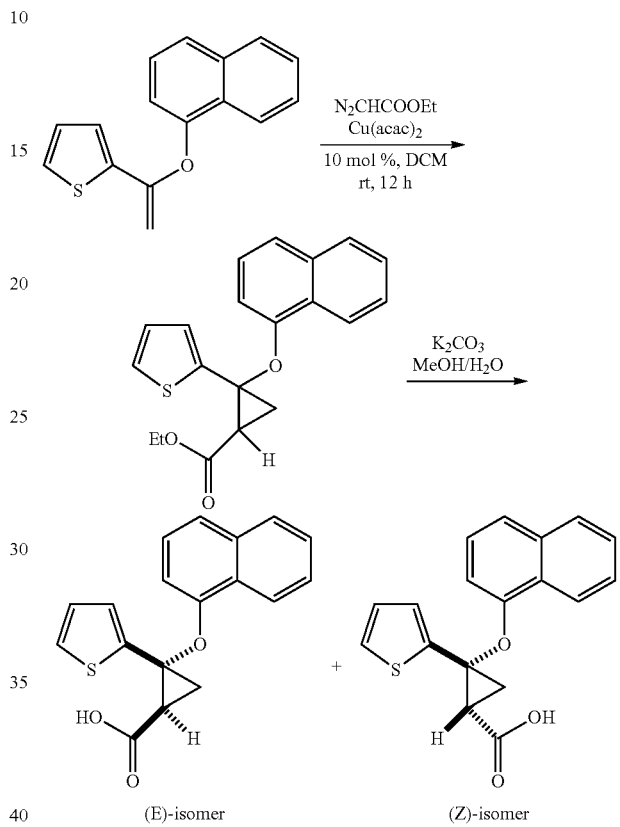

1-(Naphthalen-1-yloxy)-1-(thiophen-2-yl)ethylene (830 mg, 3.30 mmol) was dissolved in $CH_2Cl_2$ (11 mL) and $Cu(acac)_2$ (86 mg, 0.33 mmol, 10 mol %) was added to the solution. Ethyl diazoacetate (1.70 mL, 16.5 mmol) in $CH_2Cl_2$ (33 mL) was added to the mixture by syringe pump. The mixture was stirred overnight at room temperature and the reaction was quenched with saturated sodium bicarbonate solution (20 mL). The mixture was extracted with $CH_2Cl_2$ and the organic phase was dried over anhydrous sodium sulfate. The solvent was removed under reduced pressure to leave a brown oil. Flash chromatography on silica gel (2% $Et_3N$ in hexanes) gave a brown oil which was dissolved in a $MeOH/H_2O$ 2:1 (14 mL) mixture. A saturated solution of $K_2CO_3$ (5 mL) was added and the mixture was refluxed for 5 hours then was extracted with $CH_2Cl_2$. The organic phase was washed with HCl (2M) and dried with anhydrous sodium sulfate. Removal of the solvent gave the product as a 1:2 mixture of E and Z carboxylic acids, respectively (411 mg, 1.32 mmol, 40% over two steps). The acids were separated by fractional crystallization from ethyl acetate/pentane at −20° C.

(E)-isomer: mp 167-168° C. (white solid); IR (neat) 3054, 1700, 1439, 1392, 1353, 1261, 1230, 1177, 898, 789, 768, 714 $cm^{-1}$; $^1H$ NMR (400 MHz, $CDCl_3$): δ 8.23-8.25 (m, 1H), 7.76-7.78 (m, 1H), 7.49 (t, J=3.2 Hz, 1H), 7.47 (t, J=3.4 Hz, 1H), 7.42 (d, J=8.2 Hz, 1H), 7.29 (t, J=7.9 Hz, 1H), 7.20 (d, J=4.9 Hz, 1H), 7.15 (d, J=3.5 Hz, 1H), 7.11 (d, J=7.6 Hz, 1H), 6.90 (dd, J=3.8, 4.5 Hz, 1H), 2.8 (dd, J=7.6, 9.3 Hz, 1H), 2.31 (t, J=6.8 Hz, 1H), 1.96 (dd, J=6.4, 9.4 Hz, 1H); $^{13}$C NMR (100 MHz, CDCl$_3$): δ 173.2, 151.7, 138.5, 134.8, 127.7, 126.7, 126.6, 126.0, 125.7, 125.6, 122.0, 121.6, 108.7, 64.2, 31.1, 21.3. HRMS (EI) m/z 310.0674 (calcd for C$_{18}$H$_{14}$O$_3$S: 310.0664).

(Z)-isomer: mp 144-147° C. (white solid); IR (neat) 3054, 1703, 1435, 1394, 1256, 1234, 1216, 1089, 792, 770, 701 cm$^{-1}$; $^1$H NMR (400 MHz, CDCl$_3$): δ 8.22 (d, J=7.8 Hz, 1H), 7.75 (d, J=7.4 Hz, 1H), 7.39-7.49 (m, 3H), 7.25 (t, J=7.8 Hz, 1H), 7.20 (dd, J=1.1, 5.1 Hz, 1H), 7.01 (dd, J=1.1, 3.6 Hz, 1H), 6.97 (t, J=7.6 Hz, 1H), 6.93 (dd, J=3.6, 5.0 Hz, 1H), 2.51 (dd, J=7.6, 8.7 Hz, 1H), 2.28 (t, J=6.8 Hz, 1H), 2.03 (dd, J=6.6, 8.9 Hz, 1H); $^{13}$C NMR (100 MHz, CDCl$_3$): δ 173.0, 152.3, 143.8, 134.8, 127.6, 127.3, 126.6, 125.9, 125.7, 125.5, 125.2, 124.3, 122.3, 121.6, 108.6, 64.0, 32.9, 22.9. HRMS (EI) m/z 310.0674 (calcd for C$_{18}$H$_{14}$O$_3$S: 310.0664).

Example 4

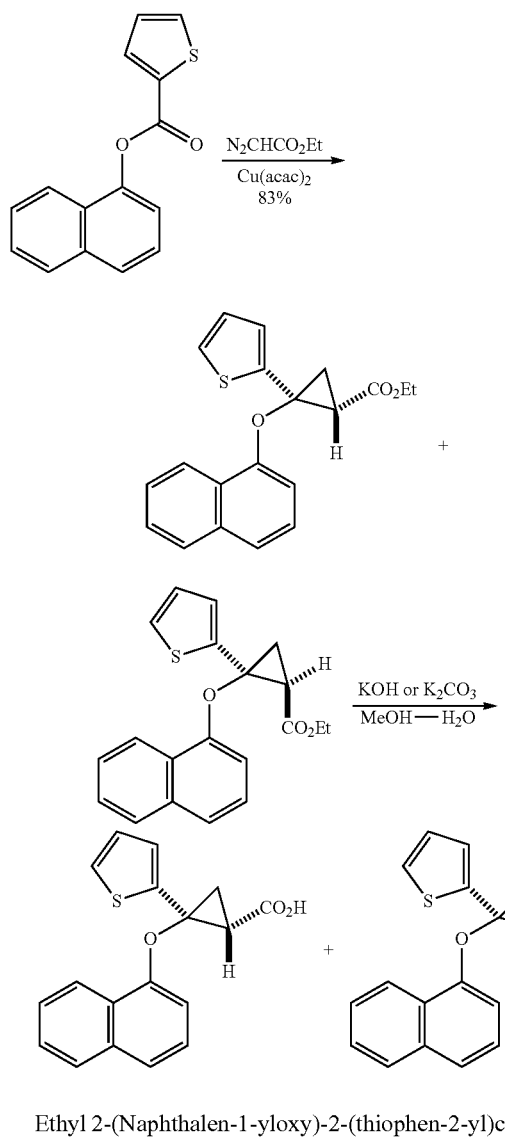

Ethyl 2-(Naphthalen-1-yloxy)-2-(thiophen-2-yl)cyclopropanecarboxylates ((±)-18 and (±)-20). To a solution of 16 (336 mg, 1.32 mmol) in dichloromethane (20 mL) was added copper(II) acetylacetonate (34.5 mg, 132 mmol). To this mixture was added a solution of ethyl diazoacetate (1.0 mL, 6.6 mmol) in dichloromethane (10 mL) over 3 h and the mixture was stirred for a further 5 hours at room temperature. The solvent was removed under vacuum and the residue was chromatographed on silica gel (0-10% ethyl acetate in hexanes) to afford a mixture of (±)-18 and (±)-20 (375 mg, E:Z 2:1):

(E)- and (Z)-2-(Naphthalen-1-yloxy)-2-(thiophen-2-yl) cyclopropanecarboxylic Acids ((±)-22 and (±)-24). To a solution of potassium hydroxide (436 mg, 7.77 mmol) in methanol (6 mL) was added a solution containing the mixture of 18 and 20 prepared above (263 mg, 0.777 mmol) in methanol (6 mL). The solution was heated at reflux for 10 hours, cooled to room temperature, poured into ice-water (60 mL) and extracted with dichloromethane (2×30 mL). The aqueous phase was adjusted to pH 1 with hydrochloric acid (2N) and was extracted with dichloromethane (3×30 mL). The combined extracts were dried (MgSO$_4$), filtered, and concentrated under reduced pressure to give a mixture of (±)-22 and (±)-24 (226 mg, 78% from 16, E:Z 2:1). The carboxylic acids were separated by fractional crystallization from ethyl acetate-pentane at −20° C. to give pure (±)-22 and (±)-24.

(±)-22: colorless solid; mp 167-168° C.; IR (neat) 3054, 1700, 1439, 1392, 1353, 1261, 1230, 1177, 898, 789, 768, 714 cm$^{-1}$; $^1$H NMR (400 MHz, CDCl$_3$) δ 1.96 (dd, J=9, 6 Hz, 1H), 2.31 (t, J=7 Hz, 1H), 2.8 (dd, J=9, 8 Hz, 1H), 6.90 (dd, J=5, 4 Hz, 1H), 7.11 (d, J=8 Hz, 1H), 7.15 (d, J=4 Hz, 1H), 7.20 (d, J=5, 1H), 7.29 (t, J=8 Hz, 1H), 7.42 (d, J=8 Hz, 1H), 7.47 (t, J=3 Hz, 1H), 7.49 (5, J=3 Hz, 1H), 7.76-7.78 (m, 1H), 8.23-8.25 (m, 1H); $^{13}$C NMR (100 MHz, CDCl$_3$) δ 21.3, 31.1, 64.2, 108.7, 121.6, 122.0, 125.6, 125.7, 126.0, 126.6, 126.7, 127.7, 134.8, 138.5, 151.7, 173.2; HRMS (EI) m/z 310.0674 (calcd for C$_{18}$H$_{14}$O$_3$S: 310.0664).

(±)-24: colorless solid; mp 144-147° C.; IR (neat) 3054, 1703, 1435, 1394, 1256, 1234, 1216, 1089, 792, 770, 701 cm$^{-1}$; $^1$H NMR (400 MHz, CDCl$_3$) δ 2.03 (dd, J=9, 7 Hz, 1H), 2.28 (t, J=7 Hz, 1H), 2.51 (dd, J=9, 8 Hz, 1H), 6.93 (dd, J=5, 4 Hz, 1H), 6.97 (t, J=8 Hz, 1H), 7.01 (dd, J=4, 1 Hz, 1H), 7.20 (dd, J=5, 1 Hz, 1H), 7.25 (t, J=8 Hz, 1H), 7.75 (d, J=7 Hz, 1H), 8.22 (d, J=8 Hz, 1H); $^{13}$C NMR (100 MHz, CDCl$_3$) δ 22.9, 32.9, 64.0, 108.6, 121.6, 122.3, 123.3, 125.2, 125.5, 125.7, 125.9, 126.6, 127.3, 127.6, 134.8, 143.8, 152.3, 173.0; HRMS (EI) m/z 310.0674 (calcd for C$_{18}$H$_{14}$O$_3$S: 310.0664).

Example 5

This example concerns synthesis protocols for (E)-N-Methyl-2-(naphthalen-1-yloxy)-2-(thiophen-2-yl)cyclopropane carboxamide.

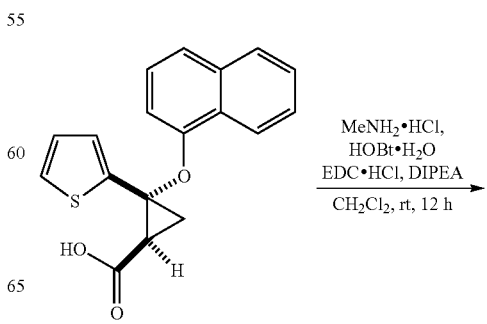

-continued

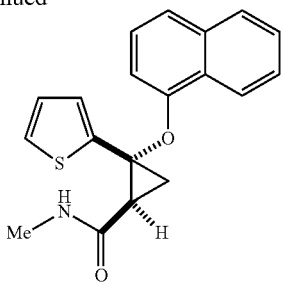

(E)-2-(Naphthalen-1-yloxy)-2-(thiophen-2-yl)cyclopropanecarboxylic acid (53.0 mg, 0.17 mmol) was dissolved in CH$_2$Cl$_2$ (0.2 mL). Methylamine hydrochloride (13.0 mg, 0.19 mmol), 1-hydroxybenzotriazole hydrate (26.0 mg, 0.19 mmol), N-(3-dimethylaminopropyl)-N'-ethylcarbodiimide hydrochloride (36 mg, 0.19 mmol) and diisopropylamine (35 μL, 0.25 mmol) were added to the solution. The solution was stirred for 12 hours at room temperature, then was diluted with CH$_2$Cl$_2$ (5 mL) and washed with NaHCO$_3$ (5 mL). The organic phase was separated and dried over anhydrous sodium sulfate. After filtration, the solvent was removed under reduced pressure to leave a white solid. Flash chromatography of this material on silica gel (30% ethyl acetate in hexanes) afforded the product as a white solid (46 mg, 0.14 mmol, 85%): mp 156-157° C.; IR (neat) 3301, 1651, 1574, 1559, 1394, 1263, 1231, 1182, 1166, 793, 772, 756, 702 cm$^{-1}$; $^1$H NMR (400 MHz, CDCl$_3$): δ 8.22-8.25 (m, 1H), 7.76-7.79 (m, 1H), 7.49 (t, J=3.3 Hz, 1H), 7.47 (t, J=3.3 Hz, 1H), 7.41 (d, J=8.2 Hz, 1H), 7.28 (t, J=7.9 Hz, 1H), 7.16 (m, 1H), 7.12 (m, 2H), 7.11 (t, J=7.8 Hz, 1H), 6.90 (dd, J=3.7, 5.0 Hz, 1H), 5.75 (d, J=3.7 Hz, 1H), 2.74 (d, J=4.8 Hz, 3H), 2.57 (dd, J=7.4, 9.8 Hz, 1H), 2.35 (t, J=6.6 Hz, 1H), 1.83 (dd, J=6.4, 9.8 Hz, 1H); $^{13}$C NMR (100 MHz, CDCl$_3$): δ 167.8, 152.0, 139.6, 124.8, 127.8, 126.7, 126.5, 125.9, 125.8, 125.5, 121.9, 121.3, 108.7, 63.3, 33.4, 26.9, 19.9. HRMS (EI) m/z 323.0986 (calcd for C$_{19}$H$_{17}$O$_2$NS: 323.0980).

Example 6

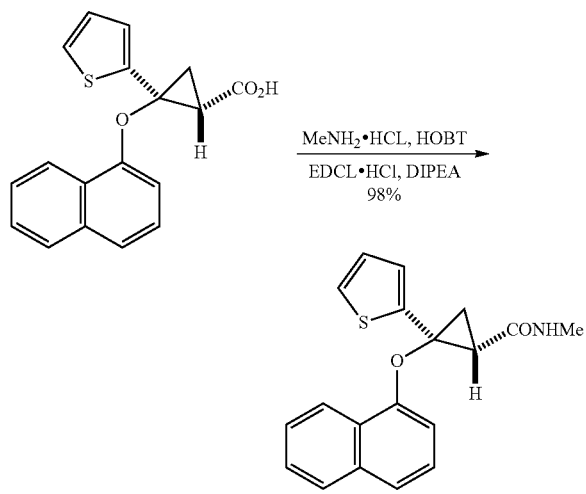

This example concerns synthesis protocols for (E)-N-Methyl-2-(naphthalen-1-yloxy)-2-(thiophen-2-yl)cyclopropane Carboxamide ((±)-26). To a solution of (±)-22 (14.0 mg, 45.1 μmol), methylamine hydrochloride (3.4 mg, 49.6 μmol), 1-hydroxybenzotriazole hydrate (6.7 mg, 46.6 μmol), and N-(3-dimethylaminopropyl)-N'-ethylcarbodiimide hydrochloride (9.5 mg, 49.6 μmol) in dichloromethane (10 mL) was added diisopropylethylamine (8.7 mg, 67 μmol). The solution was stirred for 14 hours at room temperature and then was diluted with dichloromethane (10 mL). The solution was washed with sodium bicarbonate (2×10 mL) and water (10 mL), dried (MgSO$_4$), filtered and concentrated under reduced pressure. The residue was chromatographed on silica gel (petroleum ether: ethyl acetate 1:2) to yield (±)-26 (14.3 mg, 98%) as a colorless solid: mp 156-157° C.; IR (neat) 3301, 1651, 1574, 1559, 1394, 1263, 1231, 1182, 1166, 793, 772, 756, 702 cm$^{-1}$; $^1$H NMR (400 MHz, CDCl$_3$) δ 1.83 (dd, J=10, 6 Hz, 1H), 2.35 (t, J=7 Hz, 1H), 2.57 (dd, J=10, 7 Hz, 1H), 2.74 (d, J=5 Hz, 3H), 5.75 (d, J=4 Hz, 1H), 6.90 (dd, J=5, 4 Hz, 1H), 7.11 (t, J=8 Hz, 1H), 7.12 (m, 2H), 7.16 (m, 2H), 7.16 (m, 1H), 7.28 (t, J=8 Hz, 1H), 7.41 (d, J=8 Hz, 1H), 7.47 (t, J=3 Hz, 1H), 7.49 (t, J=3 Hz, 1H), 7.76-7.79 (m, 1H), 8.22-8.25 (m, 1H); $^{13}$C NMR (100 MHz, CDCl$_3$) δ 19.9, 26.9, 33.4, 63.3, 108.7, 121.3, 121.9, 125.5, 125.8, 125.9, 126.5, 126.7, 127.8, 124.8, 139.6, 152.0, 167.8; HRMS (EI) m/z 323.0986 (calcd for C$_{19}$H$_{17}$O$_2$NS 323.0980).

Example 7

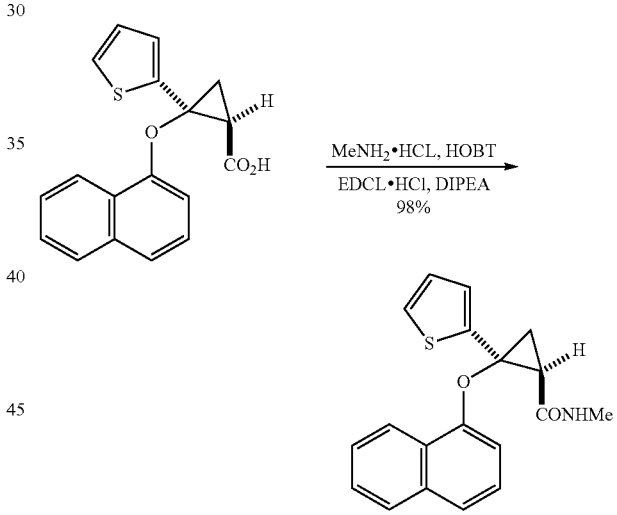

(Z)-N-Methyl-2-(naphthalene-1-yloxy)-2-(thiophen-2-yl) cyclopropane Carboxamide ((±)-28). In a manner analogous to the process described in Example 6 that was used to prepare (±)-26 from (±)-22, (±)-24 (14.0 mg, 45.1 mmol) yielded (±)-28 (14.3 mg, 98%) as a colorless solid: mp 144-145° C.; IR (neat) 3292, 1650, 1576, 1394, 1253, 1234, 1216, 792, 771, 756, 699 cm$^{-1}$; $^1$H NMR (400 MHz, CDCl$_3$) δ 2.01 (dd, J=10, 7 Hz, 1H), 2.01 (t, J=7 Hz, 1H), 2.33 (dd, J=10, 8 Hz, 1H), 2.82 (d, J=5 Hz, 1H), 6.90 (dd, J=5, 4 Hz, 1H), 6.95 (dd, J=4, 1 Hz, 1H), 7.00 (d, J=8 Hz, 1H), 7.16 (dd, J=5, 1 Hz, 1H), 7.26 (t, J=8 Hz, 1H), 7.43 (d, J=8 Hz, 1H), 7.48 (t, J=3 Hz, 1H), 7.50 (t, J=3 Hz, 1H), 7.77-7.80 (m, 1H), 8.18-8.20 (m, 1H); $^{13}$C NMR (100 MHz, CDCl$_3$) δ 21.9, 26.9, 35.1, 62.5, 108.9, 121.7, 121.8, 123.9, 124.9, 125.6, 125.9, 126.6, 127.8, 134.8, 144.3, 152.0, 168.0; HRMS (EI) m/z 323.0981 (calcd for C$_{19}$H$_{17}$O$_2$NS 323.0980).

Example 8

This example concerns synthesis protocols for (Z)-N-Methyl-2-(naphthalen-1-yloxy)-2-(thiophen-2-yl)cyclopropane carboxamide.

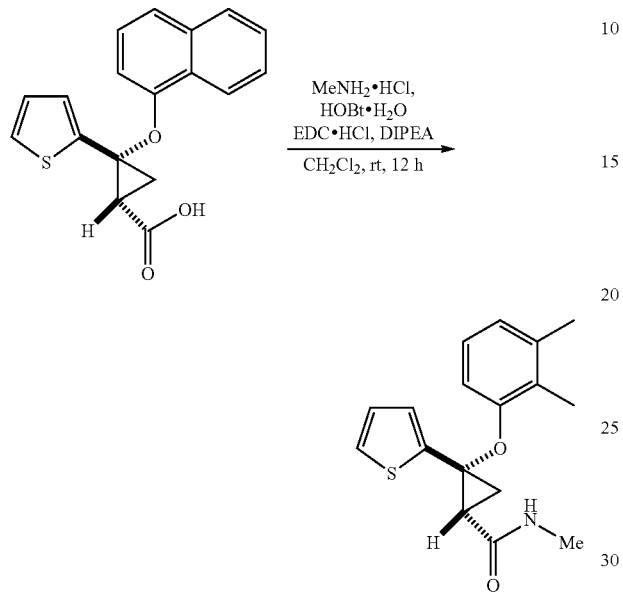

(1R,2R)-2-(Naphthalen-1-yloxy)-2-(thiophen-2-yl)cyclopropanecarboxylic acid (19.1 mg, 0.06 mmol) was dissolved in $CH_2Cl_2$ (0.1 mL). Methylamine hydrochloride (4.40 mg, 0.07 mmol), 1-hydroxybenzotriazole hydrate (9.0 mg, 0.07 mmol), N-(3-dimethylaminopropyl)-N'-ethylcarbodiimide hydrochloride (13.0 mg, 0.07 mmol) and diisopropylamine (13 μL, 0.10 mmol) were added to the solution. The solution was stirred for 12 hours at room temperature, then was diluted with $CH_2Cl_2$ (5 mL) and washed with $NaHCO_3$ (5 mL). The organic phase was separated and dried over anhydrous sodium sulfate. After filtration, the solvent was removed under reduced pressure to leave a white solid. Flash chromatography of this material on silica gel (30% ethyl acetate in hexanes) afforded the product as a white solid (17.3 mg, 0.05 mmol, 89%): mp 144-145° C.; IR (neat) 3292, 1650, 1576, 1394, 1253, 1234, 1216, 792, 771, 756, 699 $cm^{-1}$; $^1H$ NMR (400 MHz, $CDCl_3$): δ 8.18-8.20 (m, 1H), 7.77-7.80 (m, 1H), 7.50 (t, J=3.3 Hz, 1H), 7.48 (t, J=3.3 Hz, 1H), 7.43 (d, J=8.2 Hz, 1H), 7.26 (t, J=8.0 Hz, 1H), 7.16 (dd, J=1.0, 5.0 Hz, 1H), 7.00 (d, J=7.6 Hz, 1H), 6.95 (dd, J=1.0, 3.5 Hz, 1H), 6.90 (dd, J=3.6, 5.0 Hz, 1H), 2.82 (d, J=4.8 Hz, 3H), 2.33 (dd, J=7.7, 9.8 Hz, 1H), 2.10 (t, J=7.0 Hz, 1H), 2.01 (dd, J=6.8, 9.8 Hz, 1H); $^{13}C$ NMR (100 MHz, $CDCl_3$): δ 168.0, 152.0, 144.3, 134.8, 127.8, 127.3, 126.6, 125.9, 125.6, 124.9, 123.9, 121.8, 121.7, 108.9, 62.5, 35.1, 26.9, 21.9. HRMS (EI) m/z 323.0981 (calcd for $C_{19}H_{17}O_2NS$: 323.0980).

Example 9

This example concerns synthesis protocols for (E)-N-Methyl-[2-(naphthalen-1-yloxy)-2-(thiophen-2-yl)cyclopropyl]methanamine Hydrochloride.

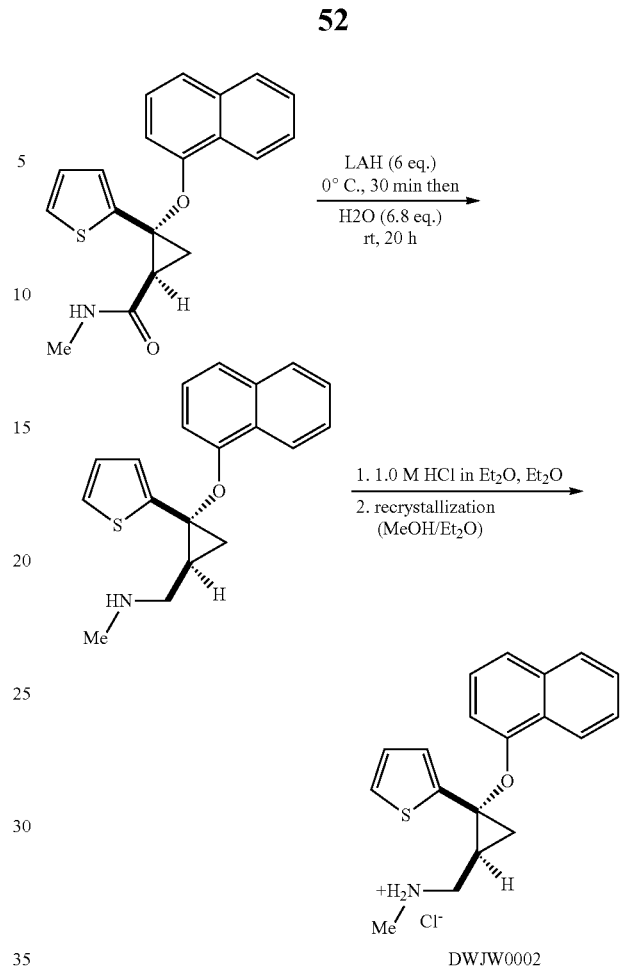

DWJW0002

To a stirred suspension of lithium aluminum hydride (281 mg, 7.42 mmol) in THF (10 mL) at 0° C. was added (E)-N-methyl-2-(naphthalen-1-yloxy)-2-(thiophen-2-yl)cyclopropanecarboxamide (400 mg, 1.24 mmol) in THF (5 mL). After 30 minutes, $H_2O$ (152 mg, 8.44 mmol) was added and gas was immediately expelled. The mixture was stirred for 4 days, after which the reaction was quenched by addition of $H_2O$ (5 mL), 15% NaOH solution (5 mL), and $H_2O$ (10 mL). After stirring for 1 hour, the mixture was filtered and the filter cake was washed with $CH_2Cl_2$ (20 mL). The organic layer was dried over anhydrous magnesium sulfate, filtered, and concentrated under reduced pressure to give the crude amine. Column chromatography (silica gel, petroleum ether:EtOAc:$Et_3N$ 1:1:0.01, followed by 5% MeOH and then 5% $NH_4OH$ solution in EtOAc to yield the amine (156 mg, 41%).

To a solution of the amine prepared above (137 mg, 0.44 mmol) in ether (10 mL) was added 1M HCl in ether (528 μL, 0.528 mmol). The precipitate was washed with ether (2×5 mL) and crystallized from MeOH/ether (−20° C.) to yield the pure amine hydrochloride DWJW0002 (95 mg) as a white solid: mp 224-225° C. (decomp); IR (neat) 2958, 2716, 2419, 1596, 1579, 1462, 1394, 1263, 1233, 1204, 1185, 793, 772, 755 $cm^{-1}$; $^1H$ NMR (400 MHz, $CDCl_3$): δ 9.76 (s, 2H), 8.21-8.24 (m, 1H), 7.73-7.76 (m, 1H), 7.47 (t, J=3.3 Hz, 1H), 7.45 (t, J=3.4 Hz, 1H), 7.37 (d, J=8.2 Hz, 1H), 7.20 (t, J=8.0 Hz, 1H), 7.12 (m, 1H), 6.98 (d, J=7.7 Hz, 1H), 6.89 (dd, J=3.8, 4.9 Hz, 1H), 3.21 (dd, J=5.6, 13.2 Hz, 1H), 2.67 (s, 3H), 2.60 (dd, J=9.7, 13.2 Hz, 1H), 2.37 (m, 1H), 2.07 (t, J=7.1 Hz, 1H), 1.76 (dd, J=7.1, 9.9 Hz, 1H); $^{13}C$ NMR (100 MHz, $CDCl_3$): δ 151.9, 140.3, 134.7, 127.7, 127.2, 126.9, 126.8, 126.6, 125.9, 125.6, 122.0, 121.4, 62.2, 48.0, 32.4, 23.3, 19.7. HRMS (EI) m/z 309.1194 (calcd for $C_{19}H_{19}ONS$ $(M-[HCl])^+$: 309.1187).

Example 10

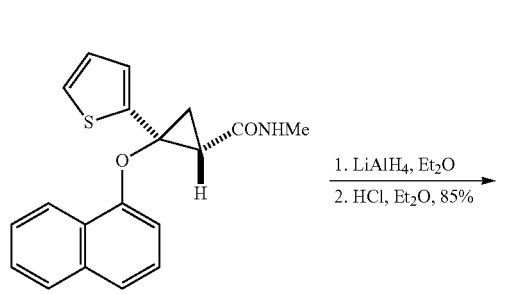

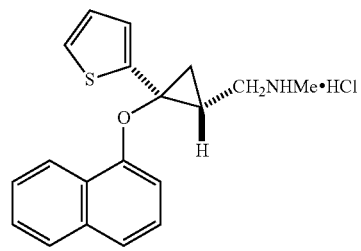

(E)-N-Methyl-2-(naphthalen-1-yloxy)-2-(thiophen-2-yl)cyclopropyl)methanamine Hydrochloride ((±)-30). To a suspension of lithium aluminum hydride (281 mg, 7.42 mmol) in ether (26 mL) was added a solution of (±)-26 (835 mg, 2.60 mmol) and the stirred slurry was heated at reflux for 2 hours. The reaction was quenched with moistened sodium sulfate and the mixture was filtered. The filter cake was washed thoroughly with ether and the filtrate was concentrated under reduced pressure to give crude amine (678 mg, 85%) which was converted immediately to its hydrochloride salt.

To a solution of the amine prepared above (137 mg, 0.44 mmol) in ether (10 mL) was added hydrochloric acid (1M) in ether (528 µL, 0.528 mmol). The resulting solid was filtered off, washed with ether (2×5 mL) and was crystallized from methanol-ether at −20° C. to give (±)-30 (95 mg, 82%) as a colorless solid: mp 224-225° C. (decomp); IR (neat) 2958, 2716, 2419, 1596, 1579, 1462, 1394, 1263, 1233, 1204, 1185, 793, 772, 755 cm$^{-1}$; $^1$H NMR (400 MHz, CDCl$_3$) δ 1.76 (dd, J=10, 7 Hz, 1H), 2.07 (t, J=7 Hz, 1H), 2.37 (m, 1H), 2.67 (dd, J=13, 10 Hz, 1H), 3.21 (dd, J=13, 6 Hz, 1H), 6.89 (dd, J=5, 4 Hz, 1H), 6.98 (d, J=8 Hz, 1H), 7.12 (m, 1H), 7.20 (t, J=8 Hz, 1H), 7.37 (d, J=8 Hz, 1H), 7.45 (t, J=3 Hz, 1H), 7.47 (t, J=3 Hz, 1H), 7.73-7.76 (m, 1H), 8.21-8.24 (m, 1H), 9.76 (s, 2H); $^{13}$C NMR (100 MHz CDCl$_3$) δ 19.7, 23.3, 32.4, 48.0, 62.2, 121.4, 122.0, 125.6, 125.9, 126.6, 126.8, 126.9, 127.2, 127.7, 134.7, 140.3, 151.9; HRMS (EI) m/z 309.1194 (calcd for C$_{19}$H$_{19}$NOS (M-[HCl]) 309.1187).

Example 11

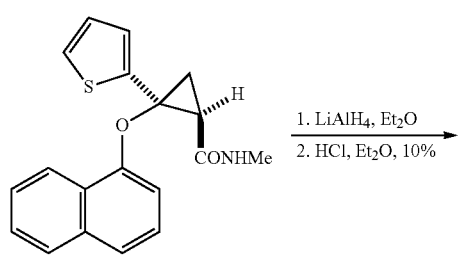

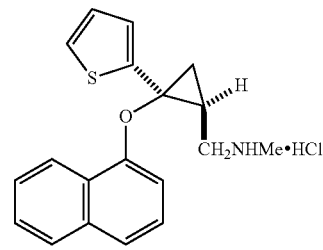

(Z)-N-Methyl-2-(naphthalen-1-yloxy)-2-(thiophen-2-yl)cyclopropyl)methanamine Hydrochloride ((±)-32). In a manner analogous to the preparation of (±)-30 from (±)-26, (±)-28 (242 mg, 0.7 mmol) gave (±)-32 (8.3 mg, 44%) as a colorless solid which was crystallized from methanol-ether at −20° C.: mp 223-224° C.; IR (neat) 3053, 2932, 2843, 2787, 1578, 1506, 1461, 1394, 1251, 1233, 1089, 792, 771, 698 cm$^{-1}$; $^1$H NMR (400 MHz, CDCl$_3$) δ 1.51 (t, J=8 Hz, 1H), 1.99 (m, 2H), 2.83 (t, J=3 Hz, 3H), 3.37 (m, 2H), 6.87 (dd, J=7, 5 Hz, 1H), 6.95 (dd, J=5, 2 Hz, 1H), 6.99 (d, J=10 Hz, 1H), 7.12 (dd, J=2, 7 Hz, 1H), 7.25 (t, J=11 Hz, 1H), 7.43 (d, J=11 Hz, 1H), 7.47-7.60 (m, 2H), 7.77-7.81 (m, 1H), 8.18-8.22 (m, 1H), 9.90 (s, 2H); $^{13}$C NMR (100 MHz, CDCl$_3$) δ 21.3, 25.9, 32.4, 47.5, 61.3, 108.8, 121.5, 121.8, 124.0, 125.0, 125.7, 126.1, 126.8, 127.3, 128.0, 134.8, 142.7, 151.9; HRMS (EI) m/z 309.1180 (calcd for C$_{19}$H$_{19}$NOS (M-[HCl]) 309.1187).

Example 12

This example concerns synthesis protocols for (Z)-N-Methyl-[2-(naphthalen-1-yloxy)-2-(thiophen-2-yl)cyclopropyl]methanamine Hydrochloride.

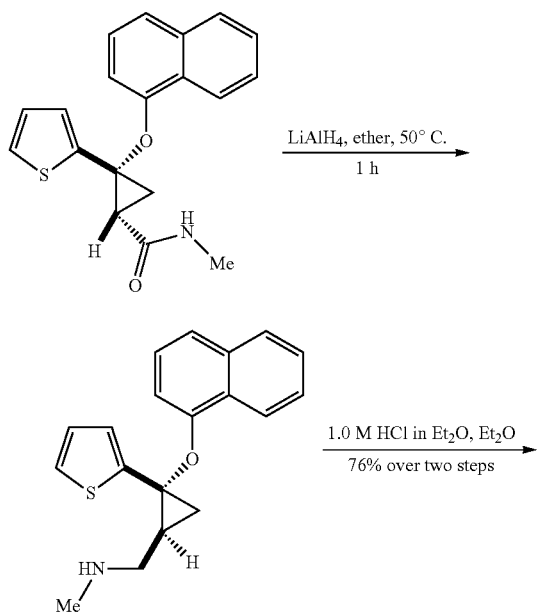

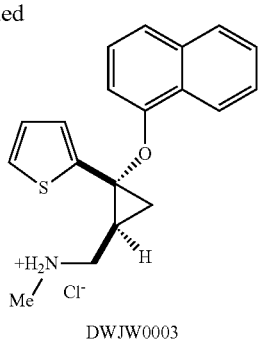

DWJW0003

(Z)-N-Methyl-2-(naphthalen-1-yloxy)-2-(thiophen-2-yl)cyclopropanecarboxamide (11.2 mg, 0.035 mmol) and lithium aluminum hydride (5.30 mg, 0.14 mmol) were placed in a flask. Ether (0.35 mL) was added, the flask was sealed, and the suspension was heated carefully at 50° C. The reaction was complete after 1 hour. Excess lithium aluminum hydride was carefully quenched with damp sodium sulfate and the mixture was filtered. Ether was removed under reduced pressure to leave the crude amine. The amine was dissolved in ether (1 mL) and HCl (1.0 M solution in ether, 60 μL, 0.06 mmol) was added. A white solid precipitated. The amine hydrochloride was filtered and washed with ether to give DWJW0003 (9.2 mg, 0.03 mmol, 76%). IR (neat) 3053, 2932, 2843, 2787, 1578, 1506, 1461, 1394, 1251, 1233, 1089, 792, 771, 698 cm$^{-1}$; $^1$H NMR (400 MHz, CDCl$_3$): δ 9.90 (s, 2H), 8.18-8.22 (m, 1H), 7.77-7.81 (m, 1H), 7.47-7.60 (m, 2H), 7.43 (d, J=11.4 Hz, 1H), 7.25 (t, J=10.8 Hz, 1H), 7.12 (dd, J=1.6, 6.7 Hz, 1H), 6.99 (d, J=10.3 Hz, 1H), 6.95 (dd, J=1.6, 4.8 Hz, 1H), 6.87 (dd, J=4.8, 6.7 Hz, 1H), 3.37 (m, 2H), 2.83 (t, J=3.1 Hz, 3H), 1.99 (m, 2H), 1.51 (t, J=8.2 Hz, 1H); $^{13}$C NMR (100 MHz, CDCl$_3$): δ 151.9, 142.7, 134.8, 128.0, 127.3, 126.8, 126.1, 125.7, 125.0, 124.0, 121.8, 121.5, 108.8, 61.3, 47.5, 32.4, 25.9, 21.3. HRMS (EI) m/z 309.1180 (calcd for C$_{19}$H$_{19}$ONS (M-[HCl])$^+$: 309.1187).

Example 13

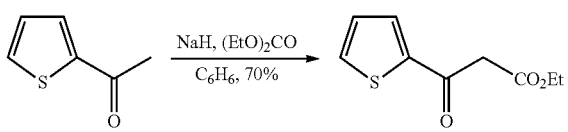

Ethyl 3-Oxo-3-(thiophen-2-yl)propanoate (36). To a suspension of sodium hydride (7.13 g, 178 mmol, 60% in mineral oil) in benzene (100 mL) was added diethyl carbonate (14.0 g, 118 mmol). The mixture was heated to reflux and a solution of 2-acetylthiophene (7.48 g, 59.4 mmol) in benzene (20 mL) was added dropwise over 1 hour. When addition was complete, the mixture was refluxed for a further 3 hours, after which hydrogen evolution had ceased. The reaction was quenched with acetic acid (15 mL) and then with ice-cold water (45 mL). The organic phase was separated, the aqueous layer was extracted with benzene and the combined extracts were washed with cold water, dried (Na$_2$SO$_4$) and concentrated under reduced pressure. The residue was distilled under high vacuum to give 36 (8.15 g, 69%) as a colorless oil: by 130° C. (0.3 torr): IR (neat) 2925, 2848, 1742, 1669, 1459, 1373, 1030, 851, 723 cm$^{-1}$; $^1$H NMR (400 MHz, CHCl$_3$) δ 1.28 (t, 3H, J=7 Hz), 3.93 (s, 2H), 4.25 (q, J=Hz, 2H), 7.16 (m, 1H), 7.71-7.76 (m, 2H); $^{13}$C NMR (300 MHz, CDCl$_3$) δ 14.1, 46.5, 61.6, 128.3, 133.2, 134.9, 142.4, 167.0, 185.2: HRMS (EI) m/z 198.0349 (calcd for C$_9$H$_{10}$O$_3$S 198.0351).

Example 14

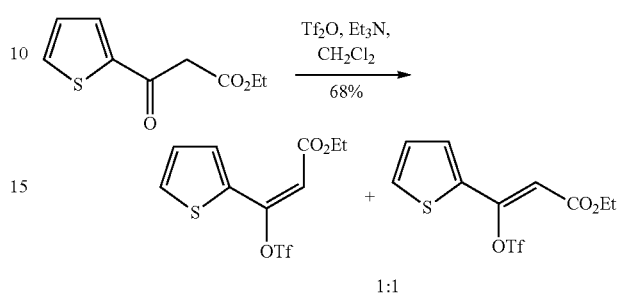

(E)- and (Z)-Ethyl 3-(Thiophen-2-yl)-3-(trifluoromethylsulfonyloxy)-acrylates (38 and 40). To a solution of 36 (1.98 g, 10.0 mmol) and triethylamine (1.8 mL, 13 mmol) in dichloromethane (80 mL) at −78° C. was added trifluoromethanesulfonic anhydride (1.85 mL, 11.0 mmol) dropwise. The resulting solution was allowed to warm to −10° C. and was stirred at this temperature for 0.5 hour. The reaction was quenched with aqueous sodium bicarbonate and the aqueous phase was extracted with dichloromethane. The combined extracts were washed with brine, dried (Na$_2$SO$_4$) and concentrated under reduced pressure. The residue was dried overnight under high vacuum to give a 1:1 mixture of 38 and 40 as a pale yellow solid: $^1$H NMR (400 MHz, CDCl$_3$) δ 1.30 (t, J=7 Hz, 3H), 4.31 (q, J=7 Hz, 2H), 6.23 (s, 1H), 7.16 (m, 1H), 7.46-7.73 (m, 2H); $^{13}$C NMR (100 MHz, CDCl$_3$) δ 13.2, 60.9, 108.6, 107.9, 132.6, 148.1, 161.3. The mixture was used immediately in the next reaction.

Example 15

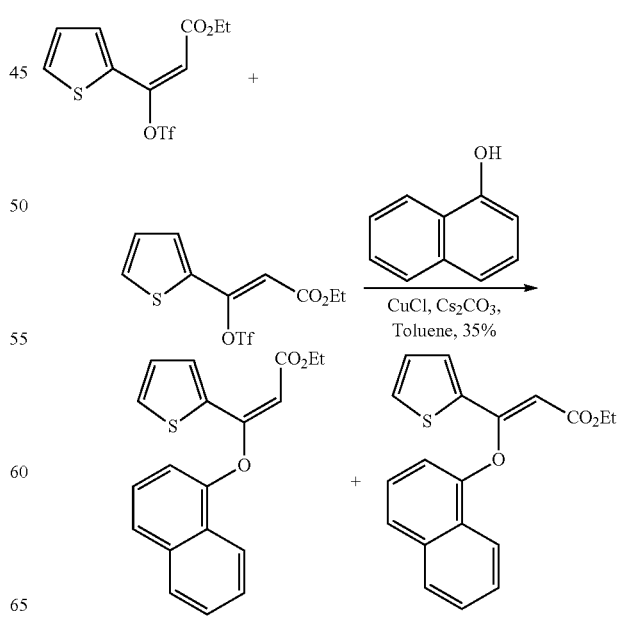

(E)- and (Z)-Ethyl 3-(Naphthalene-1-yloxy)-3-thiophen-2-ylacrylates (42 and 44). A solution containing a mixture of 38 and 40 (50.0 g, 15.0 mmol), α-naphthol (3.24 g, 22.5 mmol), copper(I) chloride (368 mg, 3.72 mmol) and cesium carbonate (9.78, 30 mmol) in toluene (75 mL) was refluxed for 4 hours. The cooled mixture was filtered through a short pad of Celite and the filtrate was washed with aqueous ammonium hydroxide, dried ($K_2CO_3$) and concentrated under reduced pressure. The residue was purified by chromatography on silica gel (hexane:ethyl acetate 40:1) to give less polar 42 (1.69 g, 35%) and more polar 44 (1.84 g, 38%), each as a pale yellow solid.

42: mp 90-92° C.; IR (KBr) 3060, 2980, 2923, 2854, 1712, 1602, 1571, 1427, 1393, 1386, 1335, 1242, 1232, 1205, 1139, 1088, 1046, 858, 807 cm$^{-1}$; $^1$H NMR (400 MHz, CDCl$_3$) δ 0.88 (t, J=7 Hz, 3H), 4.08 (q, J=7 Hz, 2H), 5.16 (s, 1H), 7.19 (m, 1H), 7.25 (m, 1H), 7.49-7.61 (m, 4H), 7.77 (m, 1H), 7.95 (m, 1H), 8.02 (m, 2H), 8.30 (m, 1H); $^{13}$C NMR (100 MHz, CDCl$_3$) δ 14.2, 60.0, 97.4, 117, 4, 121.7, 125.7, 125.8, 126.69, 126.7, 126.8, 127.2, 128.1, 129.8, 132.5, 134.9, 135.0, 149.7, 162.3, 166.3; HRMS (EI) m/z 324.0851 (calcd for $C_{19}H_{16}O_3S$ 324.0820).

44: mp 85-86° C.; IR (KBr) 3052, 2956, 2920, 2845, 1714, 1692, 1618, 1507, 1457, 1393, 1368, 1325, 1258, 1225, 1150, 1090, 1039, 790, 769, 708 cm$^{-1}$; $^1$H NMR (400 MHz, CDCl$_3$) δ 0.97 (t, J=7 HZ, 3H), 4.01 (q, J=7 Hz, 2H), 6.26 (s, 1H), 6.78 (m, 1H), 6.97 (m, 1H), 7.25 (m, 1H), 7.36 (m, 2H), 7.44-7.59 (m, 3H), 7.86 (m, 1H), 8.48 (m, 1H); $^{13}$C NMR (100 MHz, CDCl$_3$) δ 13.9, 60.2, 105.3, 107.8, 122.0, 122.2, 125.2, 125.6, 125.9, 126.6, 125.9, 126.6, 127.6, 128.2, 128.7, 128.9, 134.7, 138.1, 153.3, 156.4, 164.2; HRMS (EI) m/z 324.0827 (calcd for $C_{19}H_{16}O_3S$ 324.0820).

Example 16

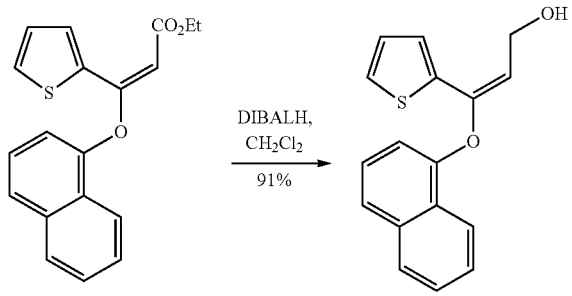 [SMILES: CCOC(=O)/C=C(/Oc1cccc2ccccc12)c1cccs1 ; OC/C=C(/Oc1cccc2ccccc12)c1cccs1]

(E)-3-(Naphthalen-1-yloxy)-3-thiophen-2-ylprop-2-en-1-ol (46). To a solution of 42 (1.69 g, 5.22 mmol) in dichloromethane (50 mL) at 0° C. was added diisobutylaluminum hydride (1.0M solution in dichloromethane, 10.5 mL, 10.4 mmol). The mixture was stirred for 30 minutes at 0° C., then was diluted with dichloromethane (50 mL) and the reaction was quenched carefully with saturated aqueous sodium potassium tartrate (70 mL). The mixture was stirred for 1 hour at room temperature and the aqueous phase was separated and extracted with dichloromethane. The combined extracts were dried (Na$_2$SO$_4$), the solvent was evaporated under reduced pressure and the residue was purified by chromatography on silica gel (hexane-ethyl acetate, 5:1) to give 46 (1.21 g, 82%) as a pale yellow oil: IR (near) 3336, 3101, 3050, 2924, 1641, 1597, 1573, 1505, 1457, 1420, 1389, 1362, 1259, 1226, 1174, 1157, 090, 1018, 991, 793, 770, 705 cm$^{-1}$;

$^1$H NMR (400 MHz, CDCl$_3$) δ 1.44 (t, J=6 Hz, 1H), 4.45 (dd, J=8, 6 Hz, 2H), 5.36 (t, J=8 Hz, 1H), 7.06-7.13 (m, 2H), 7.34-7.42 (m, 3H), 7.54 (m, 2H), 7.60 (d, J=8 Hz, 1H), 7.88 (m, 1H), 8.23 (m, 1H); $^{13}$C NMR (400 MHz, CDCl$_3$) δ 58.9, 110.3, 113.9, 121.9, 123.7, 125.8, 126.0, 126.6, 127.0, 127.2, 128.2, 134.9, 150.5, 151.6; HRMS (EI) m/z 282.0711 (calcd for $C_{17}H_{14}O_2S$ 282.0715).

Example 17

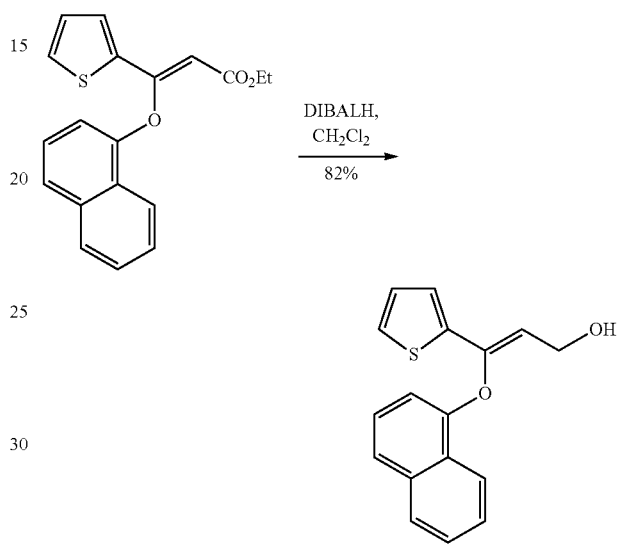

(Z)-3-(Naphthalen-1-yloxy)-3-thiophen-2-ylprop-2-en-1-ol (48). In a manner analogous to the conversion of 42 to 46, 44 (763 mg, 2.36 mmol) was reduced with diisobutylaluminum hydride to give 48 (608 mg, 91%) as a colorless oil: IR (neat) 3323, 3054, 2926, 2871, 1653, 1598, 1575, 1509, 1459, 1427, 1392, 1256, 1229, 1085, 1054, 1015, 796, 769, 700 cm$^{-1}$; $^1$H NMR (400 MHz, CDCl$_3$) δ 1.48 (t, J=6 Hz, 1H), 4.34 (t, J=7 Hz, 2H), 6.13 (t, J=7 Hz, 1H), 6.88 (m, 2H), 7.10 (d, J=4 Hz, 1H), 7.20 (d, J=5 Hz, 1H), 7.29 (m, 1H), 7.53 (d, J=8 Hz, 1H), 7.60 (m, 2H), 7.87 (m, 1H), 8.47 (m, 1H); $^{13}$C NMR (100 MHz, CDCl$_3$) δ 57.5, 107.5, 115.3, 121.7, 122.0, 125.4, 125.8 (×2), 126.7, 127.6, 127.7, 134.8, 138.4, 146.4, 152.9.

Example 18

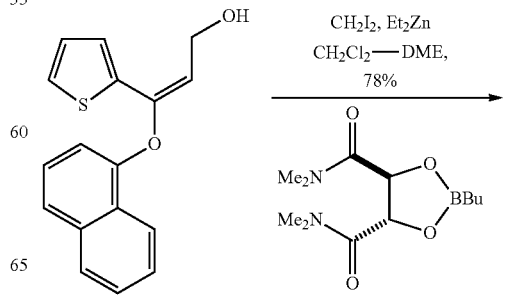

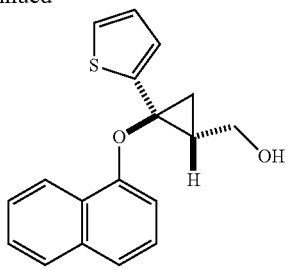

(−)-(1R,2S)-[2-(Naphthalen-1-yloxy)-2-thiophen-2-ylcyclopropyl]methanol (52). To a mixture of dichloromethane (20 mL) and 1,2-dimethoxyethane (0.5 mL) was added diethylzinc (0.53 mL, 5 mmol). To this stirred solution was added diiodomethane (0.8 mL, 10 mmol) over 15-20 minutes and the resulting clear solution was stirred for 10 min at −15° C. To this mixture was added a solution of (±)-50 (0.47 mL, 1.9 mmol) in dichloromethane (8 mL). The cooling bath was removed and the mixture was allowed to warm to room temperature and was stirred for 14 hours. Saturated aqueous ammonium chloride (30 mL) was added to quench the reaction, the aqueous phase was extracted with dichloromethane and the combined extracts were dried (NaSO$_4$). The solvent was evaporated under reduced pressure and the residue was purified by chromatography on silica gel (pentane:ethyl acetate 9:1) to give 52 (372 mg, 78%) as a colorless oil: $[\alpha]_D^{25}$ −126 (c 0.53 CHCl$_3$); IR (neat) 3050, 2954, 2922, 2849, 1596, 1577, 1503, 1462, 1392, 1363, 1315, 1264, 1235, 1181, 1095, 1050, 1015, 792, 773, 703 cm$^{-1}$; $^1$H NMR (400 MHz, CDCl$_3$) δ 1.55 (t, J=7 Hz, 1H), 2.33 (m, 1H), 3.44 (t, J=12 Hz, 1H), 3.79 (m, 1H), 6.98 (dd, J=5, 4 Hz, 1H), 7.17 (m, 1H), 7.31 (m, 3H), 7.42 (M, 1H), 7.51 (m, 2H), 7.80 (m, 1H), 8.32 (m, 1H); $^{13}$C NMR (400 MHz, CDCl$_3$) δ 18.1, 29.7, 61.6, 62.2, 108.2, 120.6, 120.8, 122.0, 125.2, 125.3, 125.5, 125.9, 126.0, 126.2, 126.3, 126.8, 127.4, 127.5, 134.5, 141.4, 152.1; HRMS (EI) m/z 296.0861 (calcd for C$_{18}$H$_{16}$O$_2$S 296.0871).

Example 19

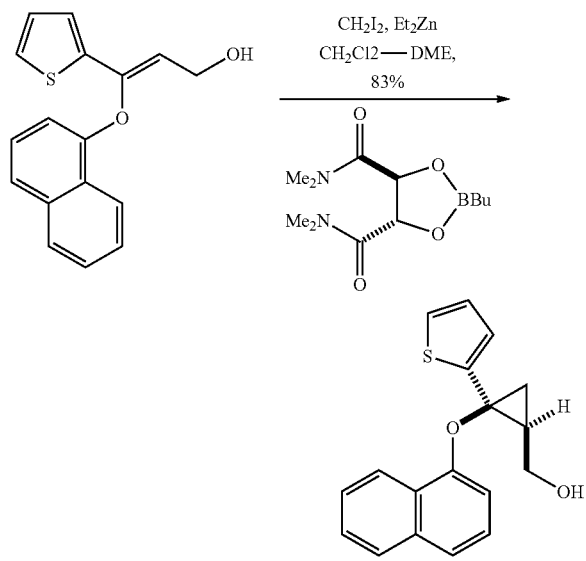

(+)-(1S,2S)-[2-(Naphthalen-1-yloxy)-2-thiophen-2-ylcyclopropyl]methanol (54). In a manner analogous to the cyclopropanation of 46 to give (−)-52, 48 (390 mg, 1.38 mmol) was reacted with 50 (407 mg, 1.52 mmol) to afford (+)-54 (340 mg, 83%): $[\alpha]_D$+7.6 (c 0.97, CHCl$_3$); $^1$H NMR (400 MHz, CDCl$_3$) δ 1.43 (t, J=7 Hz, 1H), 1.76 (dd, J=9, 6 Hz, 2H), 1.99 (m, 1H), 3.87 (dd, J=12, 8 Hz, 1H), 4.08 (m, 1H), 6.93 (m, 2H), 7.08 (d, J=8 Hz, 1H), 7.17 (dd, J=5, 1 Hz, 1H), 7.28 (m, 2H), 7.47 (d, J=8 Hz, 1H), 7.54 (dd, J=6, 3 Hz, 2H), 7.84 (dd, J=6, 3 Hs, 1H), 8.27 (dd, J=6, 3 Hz, 1H); $^{13}$C NMR (100 MHz, CDCl$_3$) δ 20.9, 32.6, 62.1, 62.3, 108.6, 121.2, 121.4, 123.0, 124.1, 125.5, 125.6, 126.5, 126.9, 127.7, 134.6, 145.6, 152.4; HRMS (EI) m/z 296.0876 (calcd for C$_{18}$H$_{16}$O$_2$S 296.0871).

Example 20

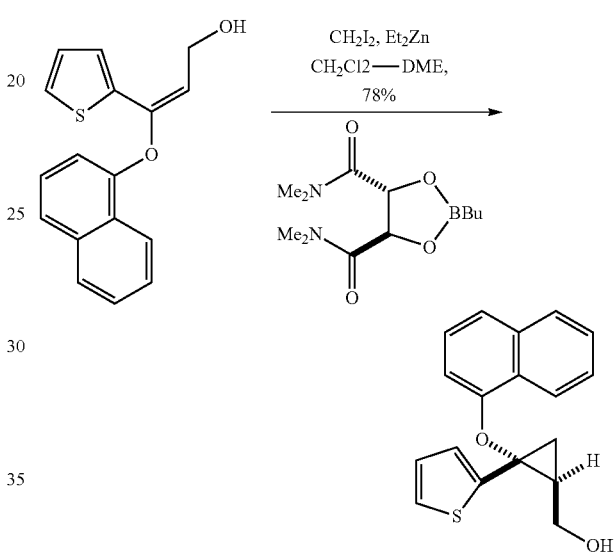

(+)-(1S,2R[2-(Naphthalen-1-yloxy)-2-thiophen-2-ylcyclopropyl]methanol (58). To a mixture of dichloromethane (20 mL) and 1,2-dimethoxyethane (0.5 mL) at −15° C. was added diethylzinc (0.53 mL, 5 mmol). To this stirred solution was added diiodomethane (0.8 mL, 10 mmol) over 15-20 minutes and the resulting clear solution was stirred for 10 minutes at −15° C. To this mixture was added a solution of 56 (0.52 mL, 2.12 mmol) in dichloromethane (4 mL) followed by a solution of 46 (500 mg, 1.77 mmol) in dichloromethane (8 mL). The cooling bath was removed and the mixture was allowed to warm to room temperature and was stirred for 14 hours. Saturated aqueous ammonium chloride (30 mL) was added to quench the reaction, the aqueous phase was extracted with dichloromethane and the combined extracts were dried (Na$_2$SO$_4$). The solvent was evaporated under reduced pressure and the residue was purified by chromatography on silica gel (pentane-ethyl acetate 9:1) to give (+)-58 (490 mg, 93%) as a colorless oil: $[\alpha]_D^{20}$+138 (c 0.19, CHCl$_3$); IR (neat) 3050, 2957, 2922, 2852, 1579, 1505, 1459, 1392, 1365, 1315, 1291, 1264, 1232, 1182, 1093, 1011, 793, 773, 700 cm$^{-1}$; $^1$H NMR (400 MHz, CDCl$_3$) δ 1.53 (t, J=7 Hz, 1H), 1.61 (dd, J=10, 7 Hz, 1H), 2.24 (m, 1H), 3.42 (dd, J=12, 9 Hz, 1H), 3.77 (dd, J=12, 6 Hz, 1H), 6.96 (k, J=4 Hz, 1H), 7.14 (d, J=3 Hz, 1H), 7.25 (d, J=8 Hz, 1H), 7.29 (d, J=3 Hz 1H), 7.32 (m, 1H), 7.32 (m, 1H), 7.44 (d, J=8 Hz, 1H) 7.52, 8.34 (m, 1H); $^{13}$C NMR (100 MHz, CDCl$_3$) δ 18.1, 29.7, 61.6, 62.2, 108.2, 120.6, 120.8, 122.0, 125.2, 125.3, 125.5, 125.9, 126.0, 126.2, 126.3, 126.8, 127.4, 127.5, 134.5, 141.4, 152.1; HRMS (EI) m/z 296.0867 (calcd for C$_{18}$H$_{16}$O$_2$S 296.0871).

Example 21

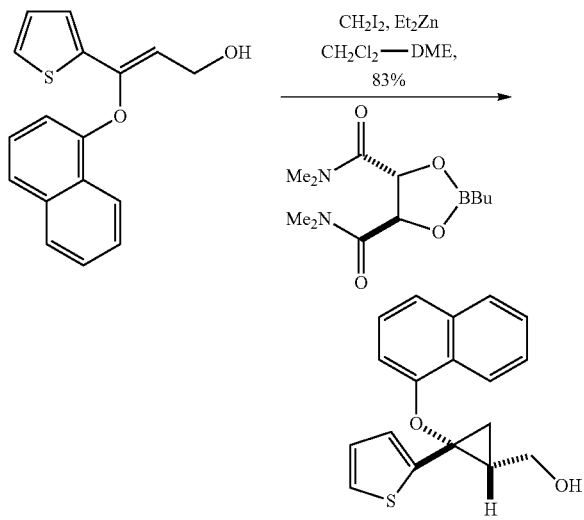

(−)-(1R,2R)-[2-Naphthalen-1-yloxy)-2-thiophen-2-ylcyclopropyl]methanol (60). In a manner analogous to the cyclopropanation of 46 to give (+)-58, alcohol 48 (410 mg, 1.45 mmol) was reacted with 56 (429 mg, 1.60 mmol) to yield (−)-60 (381 mg, 89%): $[\alpha]_D^{25}$−35 (c 0.75 CHCl$_3$); IR (neat) 3389, 3049, 2954, 2920, 1596, 1576, 1505, 1461, 1390, 1370, 1313, 1249, 1232, 1212, 1087, 1057, 1019, 905, 790, 774, 733, 700 cm$^{-1}$; $^1$H NMR (400 MHz, CDCl$_3$) δ 1.41 (t, J=7 Hz, 1H), 1.77 (dd, J=9, 6 Hz, 1H) 1.99 (m, 1H), 3.88 (dd, J=13, 8 Hz, 1H), 4.06 (dd, J=12, 6 Hz, 1H), 6.05 (br m, 2H), 7.09 (d, J=8 Hz, 1H), 7.17 (d, J=5 Hz, 1H), 7.29 (m, 1H) 7.47 (d, J=8 Hz, 1H), 7.53 (dd, J=6, 4 Hz, 2H), 7.83 (dd, J=6, 3 Hz, 1H), 8.28 (dd, J=6, 3 Hz, 1H); $^{13}$C NMR (100 MHz, CDCl$_3$) δ 21.6, 26.6, 34.9, 62.3, 108.7, 121.4, 121.6, 123.7, 124.6, 125.4, 125.6, 125.7, 126.4, 127.1, 127.6, 134.6, 144.3, 151.9, 167.7; HRMS (CI) m/z 297.0936 (calcd for C$_{18}$H$_{17}$O$_2$S 297.0949).

Example 22

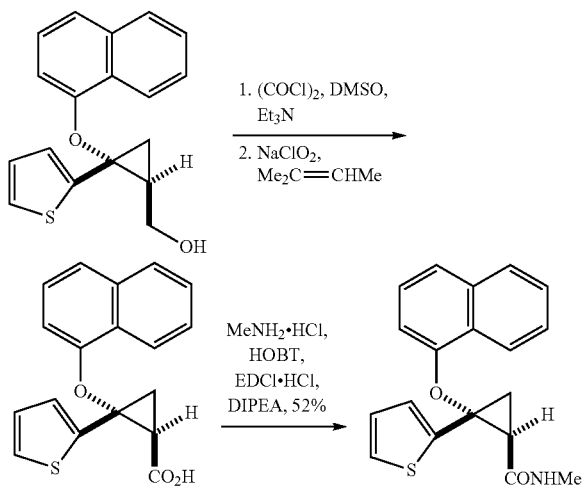

(+)-(1R,2R)-26. To a mixture of dimethyl sulfoxide (0.18 mL, 2.58 mmol) and dichloromethane (10 mL) at −78° C. was added oxallyl chloride (0.11 mL, 1.3 mmol) and the mixture was stirred at this temperature for 30 minutes. A solution of (+)-58 (296 mg, 0.86 mmol) in dichloromethane (4 mL) was added dropwise and the resulting mixture was stirred for 30 min at −78° C. Triethylamine (0.36 mL, 2.58 mmol) was added, the mixture was allowed to warm to room temperature and the reaction was quenched with ice-cold water. The mixture was extracted with dichloromethane and the combined extracts were dried (Na$_2$SO$_4$) and concentrated under reduced pressure at 35° C. The crude aldehyde obtained was used directly in the next step.

To a solution of the crude aldehyde in tert-butanol (23 mL) and tetrahydrofuran (7 mL) was added 2-methyl-2-butene. A solution of sodium dihydrogen phosphate (1.8 g, 12.5 mol) and sodium chloride (1.2 g, 13 mmol) in water (40 mL) was added and the biphasic mixture was stirred overnight at room temp. Brine was added and the mixture was extracted with dichloromethane. The combined extracts were dried (Na$_2$SO$_4$) and concentrated under reduced pressure to leave crude (−)-22 which was used directly in the next step.

To a solution of the crude carboxylic acid in dichloromethane was added methylamine hydrochloride (100 mg, 1.5 mmol), N-(3-dimethylaminopropyl-N'-ethylcarbodiimide hydrochloride (135 mg, 1.0 mmol), 1-hydroxybenzotriazole hydrate (155 mg, 1.0 mmol) and diisopropylethylamine (0.26 mL, 1.9 mmol). The mixture was stirred overnight at room temperature and the reaction was quenched with saturated aqueous sodium bicarbonate. The mixture was extracted with dichloromethane, the combined extracts were dried (Na$_2$SO$_4$), and the residue after evaporation of the solvent was chromatographed on silica gel (pentane:ethyl acetate 9:1) to give (+)-26 (145 mg, 52%) as a colorless oil: $[\alpha]_D^{25}$+138 (c 0.19, CHCl$_3$); IR (neat) 3300, 3048, 2921, 2848, 1650, 1577, 1556, 1503, 1457, 1391, 1261, 1230, 1184, 1163, 1093, 1047, 1016, 904, 794, 770, 732, 707 cm$^{-1}$; $^1$H NMR (300 MHz, CDCl$_3$) δ 1.85 (dd, J=10, 6 Hz, 1H), 2.38 (dd, J=9, 6 Hz, 1H), 2.57 (dd, J=10, 7 Hz, 1H), 2.88 (d, J=5 Hz, 3H), 5.73 (s, 1H), 6.92 (m, 1H), 7.14 (m, 2H), 7.19 (m, 1H), 7.29 (m, 1H), 7.45 (m, 1H), 7.50 (m, 2H), 7.79 (m, 2H), 8.26 (m, 1H); $^{13}$C NMR (75 MHz, CDCl$_3$) δ 19.7, 26.7, 33.2, 63.1, 108.5, 121.2, 121.5, 121.7, 124.7, 125.3, 126.6, 125.66, 125.7, 126.3, 126.5, 126.53, 127.1, 127.6, 134.6, 139.4, 151.8, 167.5; HRMS (EI) m/z 323.0981 (calcd for C$_{19}$H$_{17}$NO$_2$S 323.0980)

Example 23

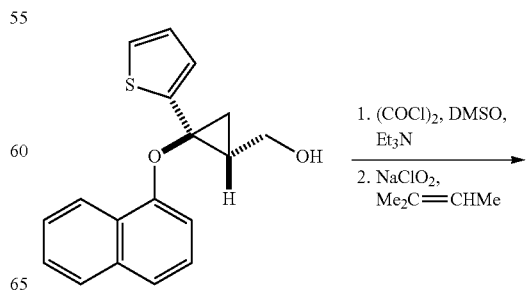

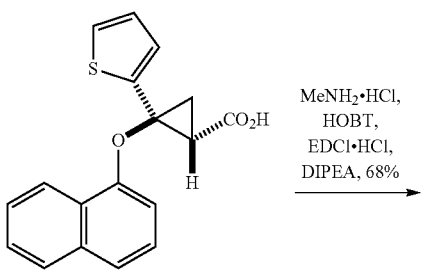

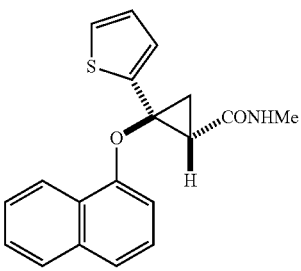

(−)-(1S,2S)-26. In a manner analogous to the conversion of 58 to (+)-26, alcohol (−)-52 (350 mg, 1.18 mmol) was oxidized to carboxylic acid (+)-22, which was reacted with methylamine hydrochloride to afford (−)-26 (140 mg, 37%): $[\alpha]_D^{25}$ −187 (0.36 CHCl$_3$).

Example 24

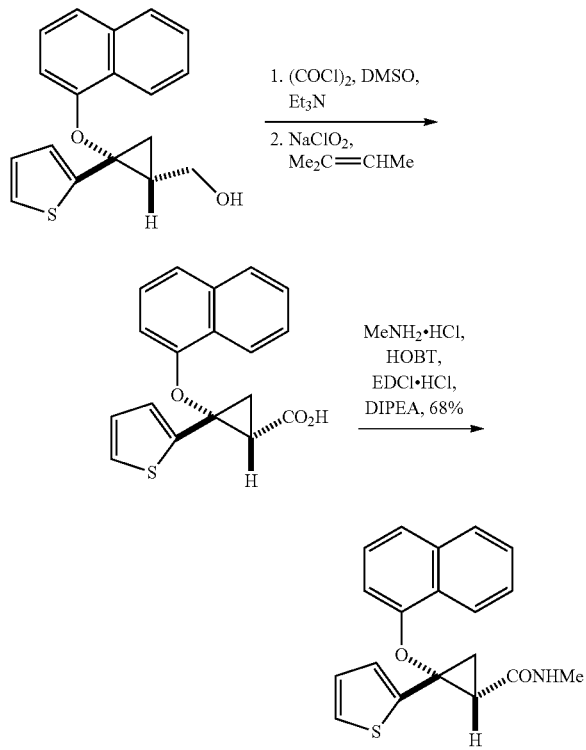

(+)-(1S,2R)-28. In a manner analogous to the conversion of (+)-58 to (+)-26, alcohol (−)-60 (70 mg, 0.24 mmol) was oxidized to carboxylic acid (−)-24 which was reacted with methylamine hydrochloride to give (+)-28 (40 mg, 54%): $[\alpha]_D^{25}$ +59.4 (c 0.36, CHCl$_3$); IR (neat) 3295, 2919, 2845, 1651, 1576, 1556, 1394, 1255, 1231, 1096, 1052, 1015, 788, 771, 700 cm$^{-1}$; $^1$H NMR (400 MHz, CDCl$_3$) δ 2.01 (dd, J=10, 7 Hz, 1H), 2.12 (t, J=7 Hz, 1H), 2.34 (dd, J=11, 8 Hz, 1H), 2.83 (d, J=6 Hz, 3H), 6.88-7.05 (m, 3H), 7.24-7.32 (m, 2H), 7.42-7.53 (m, 3H), 7.77-7.83 (m, 3H), 7.24-7.32 (m, 2H), 8.18-8.23 (m, 1H); $^{13}$C NMR (100 MHz, CDCl$_3$) δ 21.5, 26.2, 34.8, 62.5, 108.7, 121.4, 121.6, 123.7, 124.6, 125.4, 125.6, 126.4, 127.0, 127.8, 134.6, 144.4, 151.9, 167.9; HRMS (EI) m/z 323.0983 (calcd for C$_{19}$H$_{17}$NO$_2$S 323.0980).

Example 25

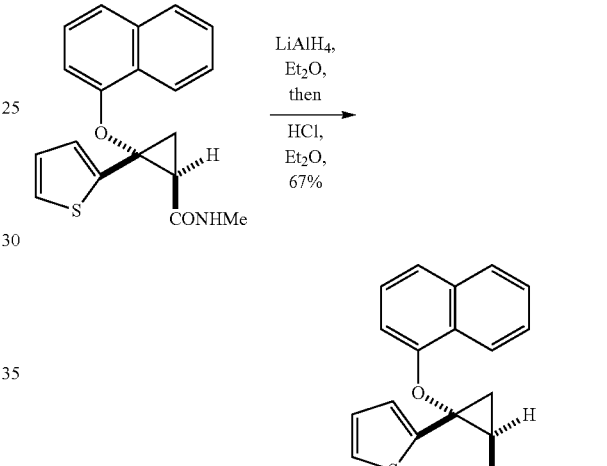

(+)-(1S,2R)-30. A slurry containing (+)-26 (145 mg, 0.445 mmol) and lithium aluminum hydride (304 mg, 8 mmol) in ether (22 mL) was heated at reflux for 5 hours. The mixture was cooled to 0° C. and the reaction was quenched with damp sodium sulfate. The mixture was filtered, the collected solid was washed with ether (30 mL) and the filtrate was evaporated under reduced pressure. The resulting oil was taken up into ether (20 mL) and hydrochloric acid (1M solution in ether, 1 mL) was added. The colorless solid that precipitated was filtered, washed with ether (3×20 mL) and was crystallized from ether (5 mL) containing methanol (0.4 mL) to afford (+)-30 (103 mg, 67%): $[\alpha]_D^{20}$ +207 (c 0.26, CHCl$_3$); IR (neat) 3369, 2957, 2922, 2848, 1599, 1579, 1505, 1459, 1392, 1260, 1233, 1186, 1089, 793, 774, 705 cm$^{-1}$; $^1$H NMR (400 MHz, CDCl$_3$) δ 1.82 (dd, J=10, 7 Hz, 1H), 2.08 (t, J=7 Hz. 1H), 2.40 (m, 1H), 2.61 (m, 1H), 2.69 (s, 3H), 3.28 (m, 1H), 6.92 (dd, J=5, 4 Hz, 1H), 7.00 (d, J=8 Hz, 1H), 7.14-7.24 (m, 3H), 7.39 (d, J=8 Hz, 1H), 7.48 (dd, J=6, 3 Hz, 1H), 7.76 (dd, J=6, 3 Hz, 1H), 8.24 (dd, J=6, 4 Hz, 1H), 9.78 (br, s, 2H); $^{13}$C NMR (100 MHz, CDCl$_3$) δ 19.5, 23.2, 32.2, 47.9, 62.0, 108.2, 121.2, 121.8, 125.4, 125.44, 125.7, 126.4, 126.6, 126.7, 127.0, 127.5, 134.5, 140.1, 151.6; HRMS (EI) m/z 309.1181 (calcd for C$_{19}$H$_{19}$NOS 309.1187).

Example 26

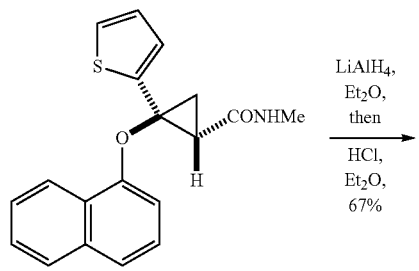

(−)-(1R,2S)-30. In a manner analogous to the conversion of (+)-26 to (+)-30, amide (−)-26 (140 mg, 0.433 mmol) was reduced to an amine which was acidified with hydrochloric acid to give (−)-30 (108 mg, 72%): $[\alpha]_D^{20}$ −189 (c 0.43, CHCl$_3$); HRMS (EI) m/z 309.1171 (calcd for C$_{19}$H$_{19}$NOS 309.1187).

Example 27

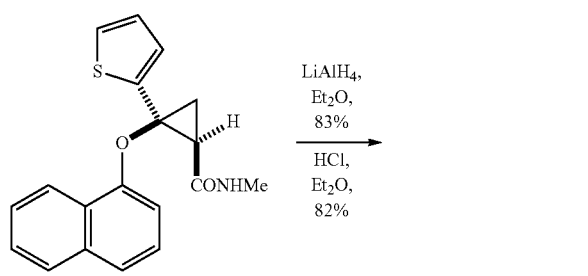

(+)-(1S,2S)-32. In a manner analogous to the conversion of (+)-26 to (+)-30, amide (−)-28 (140 mg, 0.43 mmol) was reduced with lithium aluminum hydride and the resulting amine was acidified with hydrochloric acid to give (+)-32 (120 mg, 84%) as a colorless solid: mp 252° C. (decomp); $[\alpha]_D^{20}$ +51.4 (c 0.07, CHCl$_3$); NMR (400 MHz, CDCl$_3$) δ 1.56 (br, s, 1H), 1.98-2.14 (m, 2H), 2.80-=2.97 (m, 3H), 3.36-3.46 (m, 2H), 6.87-6.92 (m, 1H), 6.95-7.05 (m, 2H), 7.15 (d, J=5 Hz, 1H), 7.25 (m, 1H), 7.45 (d, J=8 Hz, 1H), 7.53 (m, 2H) 7.81 (d, J=8 Hz, 1H), 8.26 (m, 1H), 9.86 (br, s, 2H); $^{13}$C NMR (100 MHz, CDCl$_3$) δ 22.0, 26.4, 48.3, 61.4, 83.5, 108.7, 121.6, 121.8, 124.3, 125.0, 125.48, 125.52, 126.1, 126.6, 127.3, 127.8, 134.6, 143.6, 151.7.

Example 28

(−)-(1R,2R)-32. In a manner analogous to the conversion of (+)-26 to (+)-30, amide (+)-28 (52 mg, 0.17 mmol) was reduced with lithium aluminum hydride and the resulting amine was acidified with hydrochloric acid to give (−)-32 as a colorless solid: mp 240° C. (decomp); $[\alpha]_D^{25}$ −65.6 (c 0.32, CHCl$_3$).

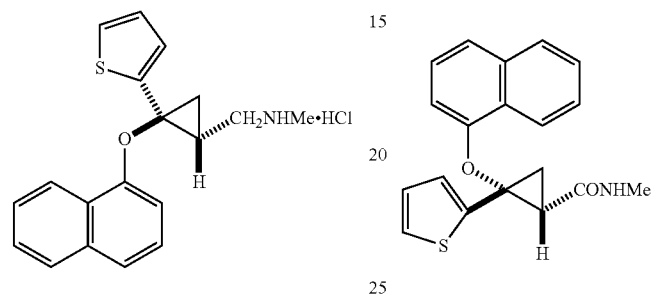

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a formula

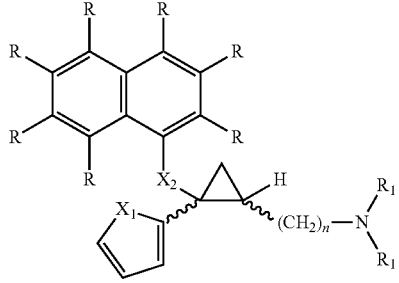

or a pharmaceutically acceptable salt thereof, where n is from 1 to 10, R groups independently are aliphatic, substituted aliphatic, aryl, substituted aryl, -cyclic, substituted cyclic, halide, heteroaryl, substituted heteroaryl, heterocyclic, substituted heterocyclic, hydrogen or hydroxyl, R$_1$ substituents independently are aliphatic, substituted aliphatic, cyclic, substituted cyclic, heterocyclic, substituted heterocyclic, or hydrogen, X$_1$ is carbon, oxygen, nitrogen or sulfur, and X$_2$ is a bond to the 3-membered ring, or is selected from a carbon, oxygen, nitrogen or sulfur atom.

2. The compound according to claim 1 where $X_2$ is selected from a carbon atom, nitrogen atom, oxygen atom or sulfur atom.

3. The compound according to claim 1 having a formula

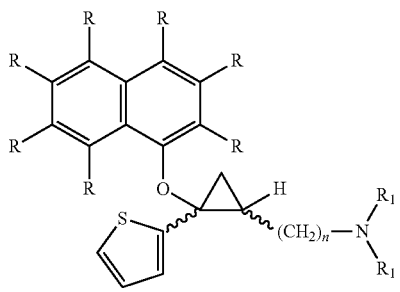

or a pharmaceutically acceptable salt thereof, where n is from 1 to 10, R independently are aliphatic, substituted aliphatic, amine, cyclic, substituted cyclic, halide, heterocyclic, substituted heterocyclic, hydrogen or hydroxyl, and $R_1$ substituents independently are aliphatic, substituted aliphatic, cyclic, substituted cyclic, heterocyclic, substituted heterocyclic, or hydrogen.

4. A compound, or a biological active salt thereof, having a formula

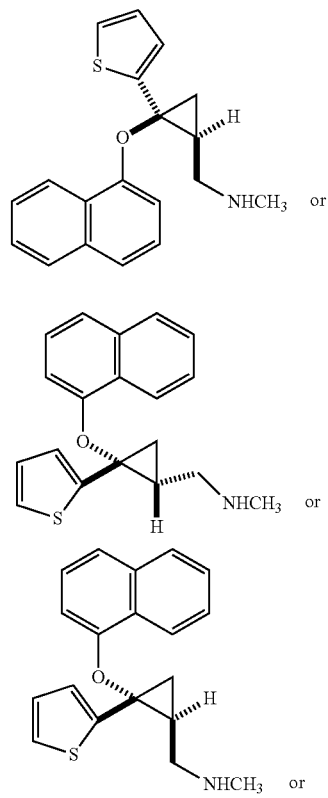

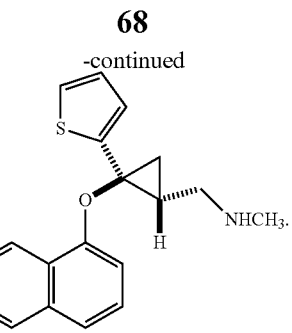

5. A composition, comprising:
a compound or pharmaceutically acceptable salt thereof, having a formula

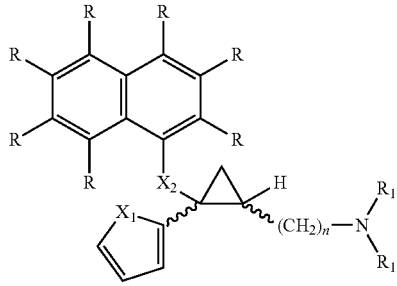

where n is from 1 to 10, R groups independently are aliphatic, substituted aliphatic, cyclic, substituted cyclic, halide, heterocyclic, substituted heterocyclic, hydrogen or hydroxyl, $R_1$ substituents independently are aliphatic, substituted aliphatic, cyclic, substituted cyclic, heterocyclic, substituted heterocyclic, or hydrogen, $X_1$ is carbon, oxygen, nitrogen or sulfur, and $X_2$ is a bond to the 3-membered ring, or is selected from a carbon, oxygen, nitrogen or sulfur atom; and
at least one additional material useful for making a pharmaceutically acceptable composition.

6. A method for making a compound having a formula

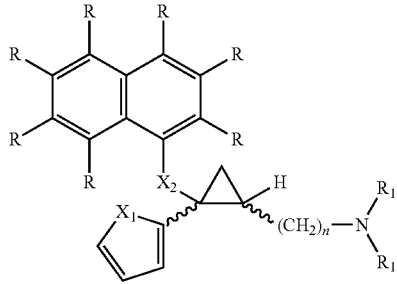

where n is from 1 to 10, R groups independently are aliphatic, substituted aliphatic, cyclic, substituted cyclic, halide, heterocyclic, substituted heterocyclic, hydrogen or hydroxyl, $R_1$ substituents independently are aliphatic, substituted aliphatic, cyclic, substituted cyclic, heterocyclic, substituted heterocyclic, or hydrogen, and $X_1$ is carbon, oxygen, nitrogen or sulfur, the method comprising:

forming an ester by reacting a carboxylic acid with an aryl alcohol, wherein the carboxylic acid has a formula

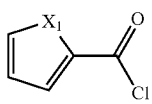

and the aryl alcohol has a formula

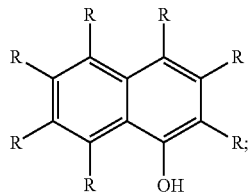

performing a Tebbe or Wittig methylenation reaction on the ester to provide an olefin; and forming a 3-membered ring from the olefin using a diazo compound.

7. An in vitro method, comprising contacting a neurotransmitter transporter with an amount of a compound effective to inhibit an activity of the neurotransmitter transporter, the compound having a formula

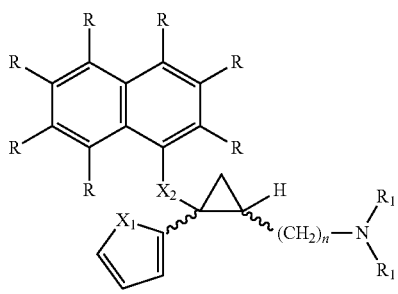

or a pharmaceutically acceptable salt thereof, where n is from 1 to 10, R groups independently are aliphatic, substituted aliphatic, cyclic, substituted cyclic, halide, heterocyclic, substituted heterocyclic, hydrogen or hydroxyl, $R_1$ substituents independently are aliphatic, substituted aliphatic, cyclic, substituted cyclic, heterocyclic, substituted heterocyclic, or hydrogen, $X_1$ is carbon, oxygen, nitrogen or sulfur, and $X_2$ is a bond to the 3-membered ring, or is selected from a carbon, oxygen, nitrogen or sulfur atom.

8. A method of treating a subject, comprising:
administering to the subject a compound having a formula

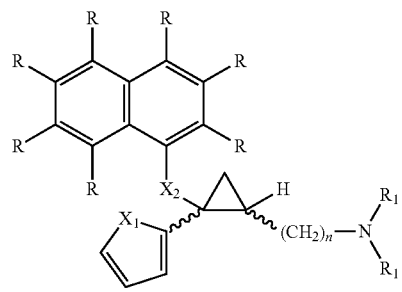

or a pharmaceutically acceptable salt thereof, where n is from 1 to 10, R groups independently are aliphatic, substituted aliphatic, cyclic, substituted cyclic, halide, heterocyclic, substituted heterocyclic, hydrogen or hydroxyl, $R_1$ substituents independently are aliphatic, substituted aliphatic, cyclic, substituted cyclic, heterocyclic, substituted heterocyclic, or hydrogen, $X_1$ is carbon, oxygen, nitrogen or sulfur, and $X_2$ is a bond to the 3-membered ring, or is selected from a carbon, oxygen, nitrogen, or sulfur atom; and wherein the subject is suffering from a disease, or a symptom thereof, selected from diabetic peripheral neuropathy, major depressive disorder (MDD), generalized anxiety disorder (GAD), or posttraumatic stress disorder.

9. The method according to claim 7 where the compound has a binding affinity from greater than 0 nM to about 40 nM for the serotonin transporter.

10. The method according to claim 9 where the compound has a binding affinity from about 1 nM to about 10 nM.

11. The method according to claim 7 where the compound has a binding affinity of greater than 0 nM to about 500 nM for the norepinephrine transporter.

12. The method according to claim 11 where the compound has a binding affinity of 1 nM to about 200 nM.

* * * * *